US007838549B2

(12) United States Patent
Suda et al.

(10) Patent No.: US 7,838,549 B2
(45) Date of Patent: Nov. 23, 2010

(54) LINKER COMPOUND, LIGAND CONJUGATE, AND PRODUCTION METHODS THEREOF

(75) Inventors: Yasuo Suda, Kagoshima (JP); Akio Arano, Nagoya (JP); Shoichi Kusumoto, Osaka (JP); Michael Sobel, Seattle, WA (US); Masahiro Wakao, Kagoshima (JP)

(73) Assignees: Japan Science and Technology Agency, Saitama (JP); National University Corporation Kagoshima University, Kagoshima (JP)

( * ) Notice: Subject to any disclaimer, the term of this patent is extended or adjusted under 35 U.S.C. 154(b) by 841 days.

(21) Appl. No.: 10/588,612

(22) PCT Filed: Feb. 4, 2005

(86) PCT No.: PCT/JP2005/001726

§ 371 (c)(1),
(2), (4) Date: Mar. 15, 2007

(87) PCT Pub. No.: WO2005/075453

PCT Pub. Date: Aug. 18, 2005

(65) Prior Publication Data

US 2007/0213523 A1 Sep. 13, 2007

(30) Foreign Application Priority Data

Feb. 5, 2004 (JP) .............................. 2004-029562

(51) Int. Cl.
*A61K 31/385* (2006.01)
*C07D 409/14* (2006.01)
(52) U.S. Cl. ........................................ 514/440; 549/39
(58) Field of Classification Search .................. 549/39; 514/440
See application file for complete search history.

(56) References Cited

U.S. PATENT DOCUMENTS

| 6,821,529 | B2 | 11/2004 | Nelson |
| 2006/0030699 | A1 | 2/2006 | Suda |

FOREIGN PATENT DOCUMENTS

| EP | 1538156 | 6/2005 |
| JP | 2002080488 | 3/2002 |
| JP | 2003-083969 | 3/2003 |
| JP | 2004157108 | 6/2004 |
| WO | WO-2004/022583 | 3/2004 |

OTHER PUBLICATIONS

Plant, A.L. et al. (1995). "Phospholipid/Alkanethiol Bilayers for Cell-Surface Receptor Studies by Surface Plasmon Resonance," Analytical Biochemistry, 226:342-348.

Liedberg, B. et al. (1995). "Biosensing with surface plasmon resonance-how it all started," Biosensors & Bioelectronics 10:i-ix.

Horan, N. et al. (1999). "Nonstatistical binding of a protein to clustered carbohydrates," PNAS, 96(21):11782-11786.

Arano, Akio et al. (2001). "Synthesis of a conjugate having heparin partial structure and a distal disulfide group and its application to chip technology," Chemical Society of Japan, Tentative Lecture Proceedings II in the 79th Spring Meeting, Mar. 15, 2001, 3 pages (4G305).

Hayashi et al. (2001). "Assembly of saccharide by multi-functional linker and application to surface plasmon resonance analysis and affinity chromatography," Tentative Lecture Proceedings, Chemical Society of Japan, vol. 83, 3 pages.

Fazio, F. et al. (2002). "Synthesis of Sugar Arrays in Microtiter Plate," J. Am. Chem. Soc., 124:14397-14402.

Fukui, S. et al. (2002). "Oligosaccharide microarrays for high-throughput detection and specificity assignments of carbohydrate-protein interactionś," Nature Biotechnology, 20:1011-1017.

Houseman, B. et al. (2002). "Carbohydrate Arrays for the Evaluation of Protein Binding and Enzymatic Modification," Chemistry & Biology, 9:443-454.

Wang, D. et al. (2002). "Carbohydrate microarrays for the recognition of cross-reactive molecular markers of microbes and host cells," Nature Biotechnology, 20:275-281.

Hayashi et al. (2003). "Synthesis, designed assembly and biotinylation of sulfated oligosaccharide and its application to surface plasmon resonance," Tentative Lecture Proceedings, Chemical Society of Japan, 3 pages.

Park, S. et al. (2004). "Carbohydrate Chips for Studying High-Throughput Carbohydrate-Protein Interactions," J. Am. Chem. Soc., 126:4812-4819.

(Continued)

*Primary Examiner*—Taofiq A Solola
(74) *Attorney, Agent, or Firm*—Morrison & Foerster LLP

(57) ABSTRACT

The present invention provides a novel linker compound which minimizes any nonspecific hydrophobic interactions and is capable of easily adjusting the length to a disulfide group subjected to metal bond to thereby enable effective formation of a metal-sulfur bond; novel ligand conjugate and ligand carrier, and a process for producing them. The linker compound is of a structure represented by the following general formula (1)

(1)

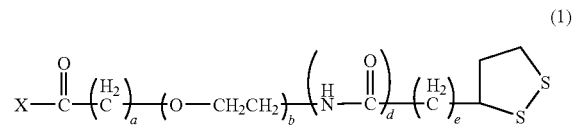

where a, b, d, e are independently an integer of 0 to 6. X has a structure serving as a multi-branched structure moiety including three or more hydrocarbon derivative chains, wherein the hydrocarbon derivative chains each include an aromatic amino group at an end thereof, and may or may not include a carbon-nitrogen bond in a main chain thereof. The ligand conjugate includes the linker compound having a sugar molecule introduced therein.

10 Claims, 16 Drawing Sheets

OTHER PUBLICATIONS

Kato, M. et al. (2004). "Using Model Substrates to Study the Dependence of Focal Adhesion Formation on the Affinity of Integrin-Ligand Complexes," Biochemistry, 43:2699-2707.

Suda, Y. (2004). "Sugar Chip: Novel Bio Device for Finding Out Biofunction of Oligosaccharides," Polymer Preprints, Japan, vol. 52, 11 pages.

Ratner, D.M. et al. (2004). "Probing Protein—Carbohydrate Interactions with Microarrays of Synthetic Oligosaccharides," ChemBioChem, 5:379-383.

Feizi, T. et al. (2004). "Oligosaccharide microarrays to decipher the glycol code," Nature, 5:582-588.

Karamanska, R. et al. (2005). "Thioctic acid amides: convenient tethers for achieving low nonspecific protein binding to carbohydrates presented on gold surfaces," Chem. Commun., pp. 3334-3336.

Arano, Akio et al. (2002) "Preparation of novel clustered oligosaccharide-ligand containing multi-units of heparin partial structure and its application for chip technology," The Chemical Society of Japan Koen Yokoshu, 82: 137.

Arano, Akio et al. (2003) "Preparation of Sugar Chips Immobilized with Clustered Sulfated Oligosaccharides and their Application of Surface Plammon Resonnance," The Japanese Society of Carbohydrate Research Nenkai Yoshishu, 24: 127.

Suda, Yasuo et al. (2003) "Development of Analytical System for the Function of Oligosaccharides at Nanometer Scale," The Japanese Society of Carbohydrate Research Nenkai Yoshishu, 24: 36.

International Search Report mailed Mar. 15, 2005, for international application No. PCT/JP2005/001726, filed Feb. 4, 2005, 2 pages.

Supplementary European Search Report for EP 05709791.7, mailed Aug. 27, 2007, 3 pages.

Mono; Mono-GlcNS6S-IdoA2S-Glc, Tri; Tri-GlcNS6S-IdoA2S-Glc,
Tetra; Tetra-GlcNS6S-IdoA2S-Glc

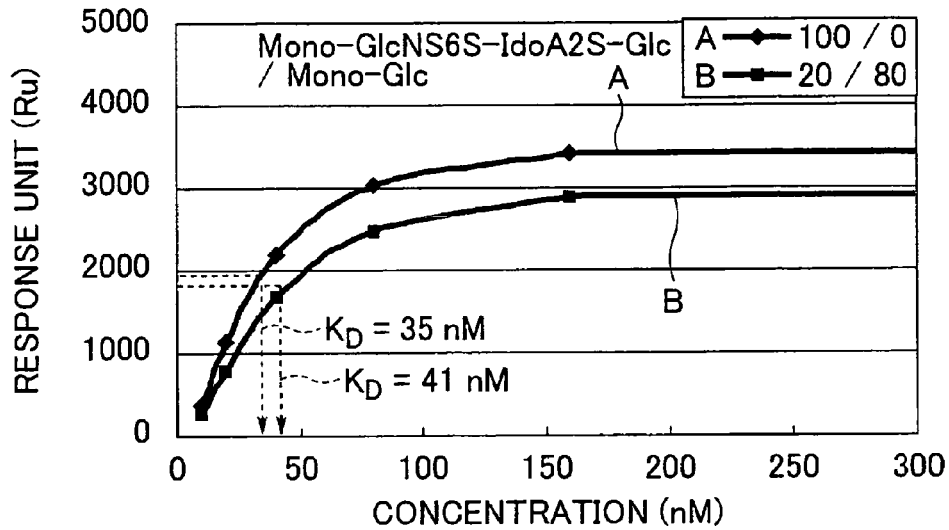
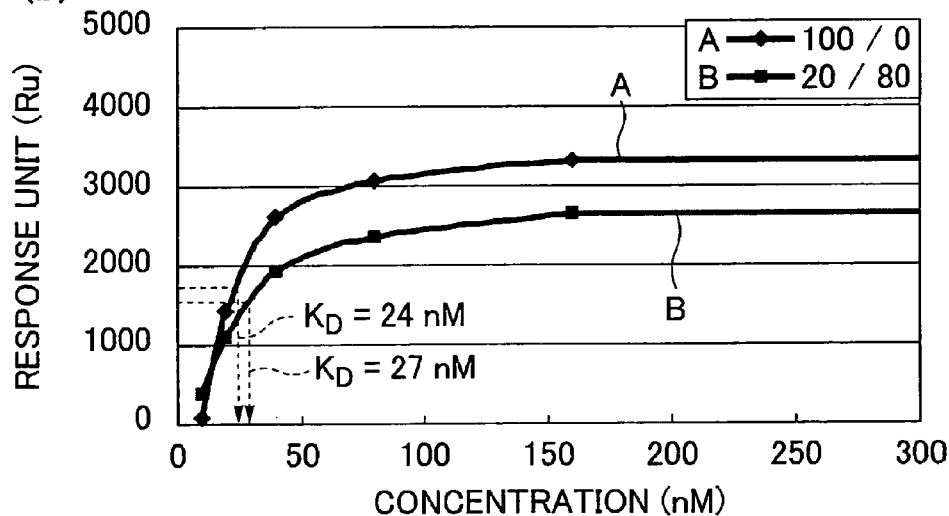
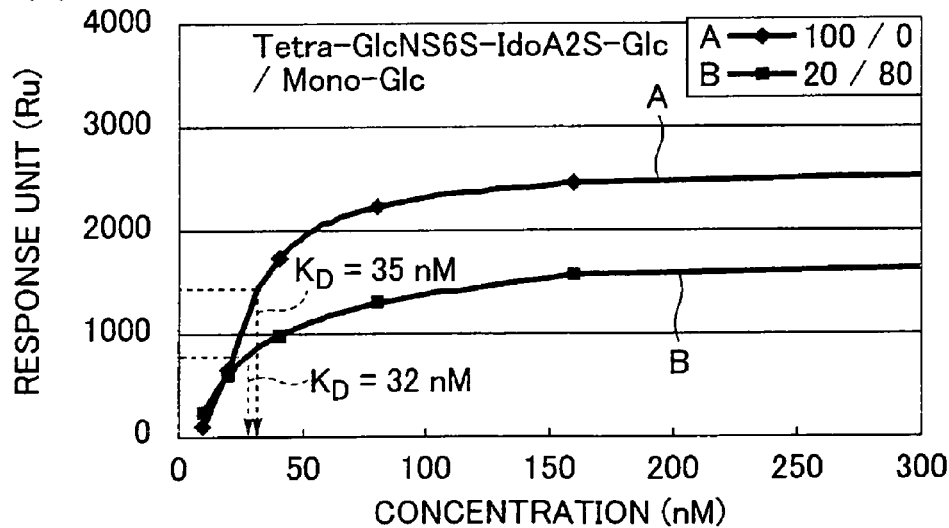

US 7,838,549 B2

LINKER COMPOUND, LIGAND CONJUGATE, AND PRODUCTION METHODS THEREOF

CROSS REFERENCE TO RELATED APPLICATIONS

This application is a 35 U.S.C. §371 National Stage filing of International Patent Application No. PCT/JP2005/001726, titled LINKER COMPOUND, LIGAND CONJUGATE, AND PRODUCTION METHODS THEREOF, filed Feb. 4, 2005; which claims priority to Japanese Application No. 29562/2004, titled LINKER COMPOUND, LIGAND CONJUGATE, AND PRODUCTION METHODS THEREOF, filed Feb. 5, 2004; both of which are incorporated herein by reference in their entireties.

TECHNICAL FIELD

The present invention relates to a linker compound capable of immobilization of sugar chains of oligosaccharide or the like on a protein-analyzing supporter such as a sensor chip of a surface plasmon resonance, a ligand conjugate including the linker compound having a sugar chain introduced therein, a ligand carrier, and production methods thereof.

BACKGROUND ART

Various intravital sugar chains play an important role in a mechanism for sustaining activities and lives of living organisms. In order to specifically reveal the functions of such sugar chains, it is necessary to analyze the functions of the sugar chains based on a complex structure thereof. Functional analysis of the sugar chains is carried out by the following technique. The structure of a sugar chain is reproduced part by part by analyzing the function of oligosaccharide whose structure is elucidated, so as to clarify the relation between the structure of a whole sugar chain and its functions.

As the technique of the functional analysis of sugar chains, the surface plasmon resonance (hereinafter referenced to as SPR) method is known, for example. That is, the ligand conjugate containing the oligosaccharide which imitates a part of sugar chain is immobilized on the sensor chip surface. By using the sensor chip having oligosaccharide immobilized thereon, substance, such as protein, which specifically interacts with oligosaccharide are identified. This makes it possible to properly evaluate a biological activity based on the structure of oligosaccharide.

Meanwhile, a single oligosaccharic molecule is not active enough. Therefore, it is necessary to collect sugar chains of oligosaccharide onto the sensor chip when evaluating a biological activity of an oligosaccharide. In other words, the use of collected sugar chains of oligosaccharide for analysis of interaction with a protein allows for evaluation of biological activity of sugar chains of oligosaccharide.

In view of this, the inventors of the present invention have so far found a linker compound including molecules having therein (i) moiety capable of being immobilizable onto the surface of the sensor chip and (ii) moiety capable of taking in sugar chains of oligosaccharide. Also, the inventors have so far found a ligand conjugate which includes the linker compound having one or two units of sugar chains of oligosaccharide introduced thereinto. Then, the inventors found that the use of such a ligand conjugate makes it possible to collect and introduce sugar chains of oligosaccharide onto the sensor chip (for example, see Patent document 1, Non-patent document 1).

[Patent Document 1]
Japanese Unexamined Patent Publication No. 836969/2003 (Tokukai 2003-836969; published on Mar. 19, 2003)
[Non-Patent Document 1]
Tentative Lecture Proceedings II in the 79th Spring Meeting, Chemical Society of Japan, Mar. 15, 2001, p. 1042

The use of the ligand conjugates disclosed in Patent document 1 and Non-patent document 1 makes it possible to arrange sugar chains of an oligosaccharide two-dimensionally on a surface of a sensor chip. However, there is a technical problem left in that it is difficult to arrange the sugar chains with high reproducibility.

That is, in order to analyze a biological activity of sugar chains of an oligosaccharide by using sugar chains of oligosaccharide molecules collected onto a surface of a sensor chip as described above, it is necessary to observe with high reproducibility an interaction between the sugar chains of the oligosaccharide and a protein, with the sugar chains of the oligosaccharide collected uniformly. Especially, in order to observe a biological activity of sugar chains of an oligosaccharide, it is important to evaluate a biological activity of sugar chains of oligosaccharide with high reproducibility by collecting sugar chains of three or more units of oligosaccharide onto a surface of a sensor chip so as to arrange the sugar chains two-dimensionally on the sensor chip with high reproducibility.

In the ligand conjugate disclosed in Non-patent document 1, one ligand conjugate has sugar chains of one or two units of oligosaccharides. In other words, the ligand conjugate consists of one linker compound and sugar chains of one or two oligosaccharides bonded to the linker compound. Therefore, in order to observe a biological activity of sugar chains of an oligosaccharide, it is necessary to collect sugar chains of three or more units of oligosaccharides onto a surface of a sensor chip by increasing a concentration of a ligand conjugate to collect the sugar chains, which are a ligand, in arranging the ligand conjugate onto the surface of the sensor chip.

The use of such techniques for collection of sugar chains of oligosaccharides makes it difficult to obtain with high reproducibility an arrangement of oligosaccharides wherein an interval between sugar chains of oligosaccharides is controlled so as to be a predetermined interval. Therefore, the functional analysis of oligosaccharide by using the conventional ligand conjugate makes it impossible to observe biological activities of oligosaccharides with high reproducibility. This might make it difficult to reveal a structure of sugar and to evaluate biological activities of oligosaccharides.

The present invention was made to solve the above problems. It is an object of the present invention to provide a novel linker compound with which oligosaccharides can be two-dimensionally arranged with high reproducibility while an interval between their sugar chains on a surface of a sensor chip is controlled. The present invention also provides a novel ligand conjugate which includes the linker compound and a sugar molecule introduced into the linker compound, a ligand carrier, and a process for producing the same.

DISCLOSURE OF INVENTION

The inventors diligently studied to solve the above problems. As a result, the inventors found a novel linker compound which has a moiety capable of taking in three or more units of sugar molecules. The novel linker compound also has a moiety capable of forming a bond with a protein-analyzing supporter such as a sensor chip of surface plasmon resonance (SPR) and a carrier of an affinity chromatography. The inventors also found that the novel linker compound can be used to arrange three or more units of sugar molecules two-dimensionally on the supporter with high reproducibility.

The inventors disclose another linker compound found to solve the above problems in their previously filed patent application (Japanese Patent Application No. 190568/2003 (Tokukai 2003-190568), Japanese Unexamined Patent Publication No. 157108/2004 (Tokukai 2004-157108; published on Jun. 3, 2004) which was not published as of a priority date of the present application (Feb. 5, 2004)). However, such another linker compound has the problem that in analyzing a protein with extremely high hydrophobic property, the linker compound makes non-specific binding interaction with the protein at an alkyl group of a linker section thereof. Further, the another linker compound has an insufficient length of the alkyl group which makes up the linker section, and therefore has the problem that when a sugar chain of oligosaccharide to be immobilized is large, the linker compound does not effectively make metal-sulfur bond due to steric hindrance of sugar chains of oligosaccharide.

In view of this, the inventors of the present application found that introduction of oligoethylene oxide group into the linker section makes it possible for the linker compound to minimize non-specific hydrophobic interaction and to easily adjust a length to a disulfide group subjected to metal bond so as to effectively form a metal-sulfur bond, thereby completing the present invention.

That is, in order to solve the above problems, a linker compound of the present invention has a structure represented by following general formula (1), where a, b, d, e are independently an integer of 0 to 6, and X has a structure serving as a multi-branched structure moiety including three or more hydrocarbon derivative chains, wherein the hydrocarbon derivative chains each include an aromatic amino group at an end thereof, and may or may not include a carbon-nitrogen bond in a main chain thereof.

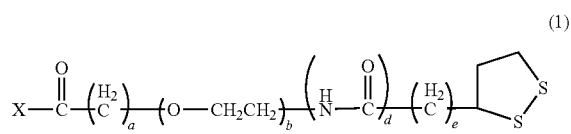

(1)

Further, a linker compound of the present invention may have a structure represented by following general formula (2), where n is an integer of 1 to 6, and X has a structure serving as a multi-branched structure moiety including three or more hydrocarbon derivative chains, wherein the hydrocarbon derivative chains each include an aromatic amino group at an end thereof, and may or may not include a carbon-nitrogen bond in a main chain thereof.

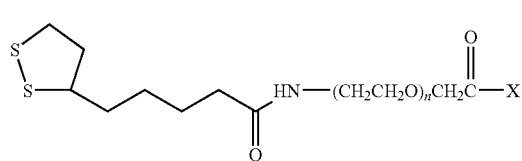

(2)

Each of the hydrocarbon derivative chains is a hydrocarbon chain, consisting of carbon and hydrogen, part of whose carbon and hydrogen may be replaced with another atom and a substituent. That is, the hydrocarbon derivative chain is a hydrocarbon chain, having an aromatic amino group at an end thereof, part of whose carbon-carbon bond (C—C bond), serving as a main chain structure of the hydrocarbon chain, may be replaced with a carbon-nitrogen bond (C—N bond), a carbon-oxygen bond (C—O bond), and an amide bond (CO—NH bond).

According to the above arrangement, the linker compound has an aromatic amino group serving as a moiety capable of easily taking in sugar molecules. Since the aromatic amino group is included in each hydrocarbon derivative chain, three or more units of sugar molecules can be introduced into the linker compound. Further, the linker compound has a S—S bond serving as a moiety immobilizable onto the protein-analyzing supporter.

Thus, the use of the linker compound makes it possible to collect and introduce three or more units of sugar molecules onto the supporter. Since three or more units of sugar molecules are introduced into one linker compound, it is possible to arrange three or more units of sugar molecules on the surface of the supporter with high reproducibility. This makes it possible to observe an interaction between a sugar molecule and a protein on the surface of the supporter, and to evaluate a biological activity of a sugar molecule with high reproducibility.

Further, the linker compound has an oligoethylene dioxide group in a linker thereof. This linker compound makes it possible to significantly reduce the possibility of causing a non-specific interaction with a target to be analyzed with high hydrophobicity, as compared with a linker compound having alkyl group in a linker thereof. Moreover, the linker section being made up of oligoethylene dioxide makes it possible to easily adjust a length from a disulfide group subjected to metal bond to a sugar chain of oligosaccharide bound to an amino group end. This makes it possible to effectively form a metal-sulfur bond without the disulfide group affected by chains of oligosaccharide.

In the linker compound having the structure represented by the general formula (1) or (2), it is preferable that X has a structure represented by following general formula (3), wherein $m^1$, $m^2$, $m^3$, $m^4$, $p^1$, and $p^2$ are independently an integer of 1 to 6.

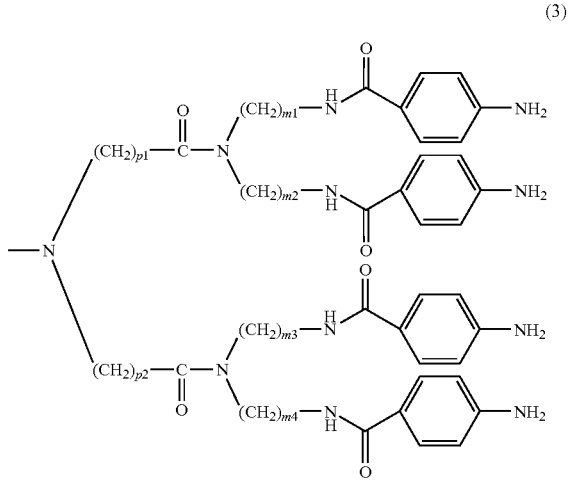

(3)

Further, in the linker compound having the structure represented by the general formula (1) or (2), it is preferable that X has a structure represented by following general formula (4), wherein $q^1$, $q^2$, $q^3$, $r^1$, $r^2$, $r^3$, $t^1$, $t^2$, $t^3$, $u^1$, $u^2$, and $u^3$ are independently an integer of 0 to 6.

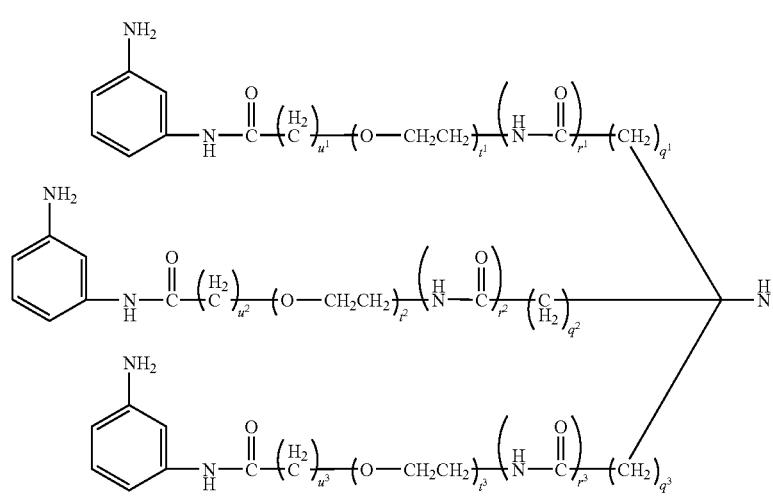

(4)

Since X of the linker compound has the three or more hydrocarbon derivative chains, the linker compound makes it possible to introduce three or more units of sugar molecules onto the supporter. Therefore, the use of the linker compound makes it possible to control an interval between three or more sugar molecules introduced on the surface of the supporter, thereby making it possible to obtain an arrangement of the sugar molecules with high reproducibility. This allows for evaluation of a biological activity of a sugar molecule with high reproducibility.

Further, in order to solve the above problems, a ligand conjugate of the present invention comprises the aromatic amino group of any of the foregoing linker compounds and a sugar molecule introduced into the aromatic amino group.

More specifically, it is preferable that the ligand conjugate has a structure represented by following general formula (5),

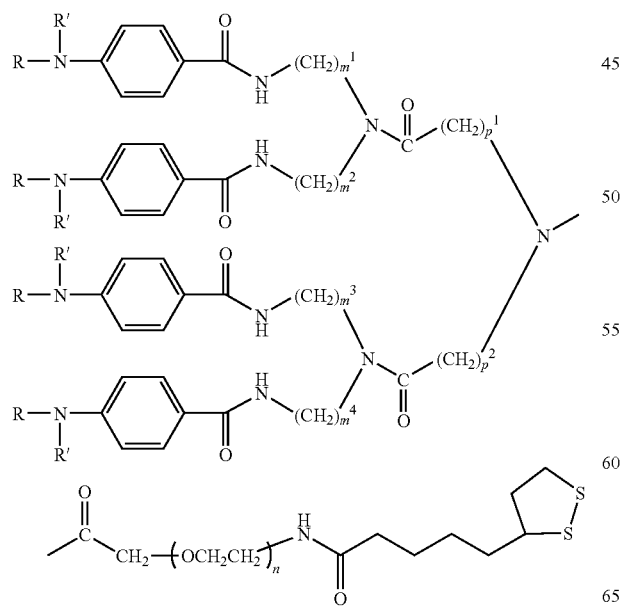

(5)

where $m^1$, $m^2$, $m^3$, $m^4$, n, $p^1$, and $p^2$ are independently an integer of 1 to 6, R' is hydrogen (H) or R, and R is an oligosaccharide-derived compound selected from among the following formulae (6-1) through (6-6).

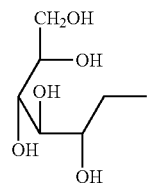

(6-1)

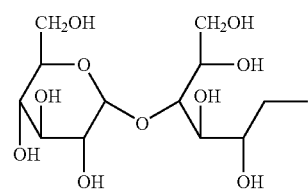

(6-2)

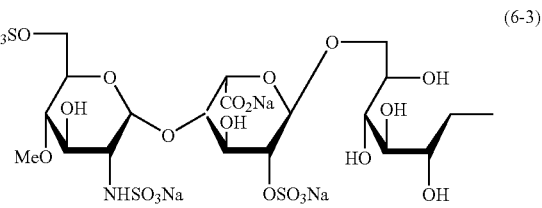

(6-3)

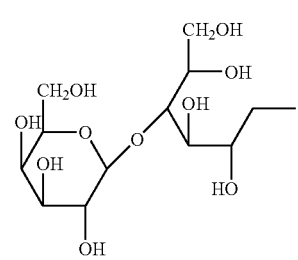

(6-4)

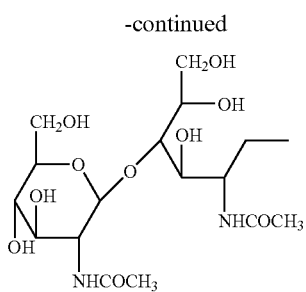

(6-5)

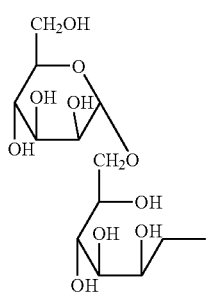

(6-6)

More specifically, it is preferable that the ligand conjugate has a structure represented by following general formula (7), where a, b, d, e, $q^1$, $q^2$, $q^3$, $r^1$, $r^2$, $r^3$, $t^1$, $t^2$, $t^3$, $u^1$, $u^2$, and $u^3$ are independently an integer of 0 to 6, $t^1$, $t^2$, and $t^3$ are not 0 when b is 0, b is not 0 when $t^1$, $t^2$, and $t^3$ are 0, R' is hydrogen (H) or R, and R is an oligosaccharide-derived compound selected from among the above formulae (6-1) through (6-6).

The use of any one of the ligand conjugates makes it possible to collect and immobilize three or more or four or more (in case of a ligand conjugate having a structure represented by general formula (5) or (7)) units of sugar molecules onto the surface of the protein-analyzing supporter. Also, since one ligand conjugate has three or more units of sugar molecules, it is not necessary to collect the ligand conjugates onto the surface of the supporter. The use of one ligand conjugate makes it possible to collect three or more units of sugar molecules. This makes it possible to measure a biological activity of a sugar molecule with high reproducibility. Moreover, it is possible to arrange a plurality of sugar molecules two-dimensionally on the surface of the supporter with high reproducibility. Thus, the use of the protein-analyzing supporter including a ligand conjugate of the present invention immobilized thereon makes it possible to evaluate a biological activity of a sugar molecule with high reproducibility.

Further, in order to solve the above problems, a producing method of a linker compound of the present invention, includes the steps of: carrying out a condensation reaction between thioctic acid and an amine compound including three or more branched chains each having an aromatic amino group end protected by a protecting group; and deprotecting the protecting group at the aromatic amino group end.

According to the above method, it is possible to obtain a linker compound of the present invention including an S—S bond serving as a moiety capable of being immobilizable on the protein-analyzing supporter and a aromatic amino group serving as a moiety capable of easily taking in sugar molecules.

In order to solve the above problems, a producing method of a ligand conjugate of the present invention, includes the step of carrying out a reductive amination reaction by using the foregoing linker compound and a sugar molecule.

According to the above method, it is possible to obtain a ligand conjugate of the present invention by easily introducing a sugar molecule into a linker compound by reductive amination reaction.

(7)

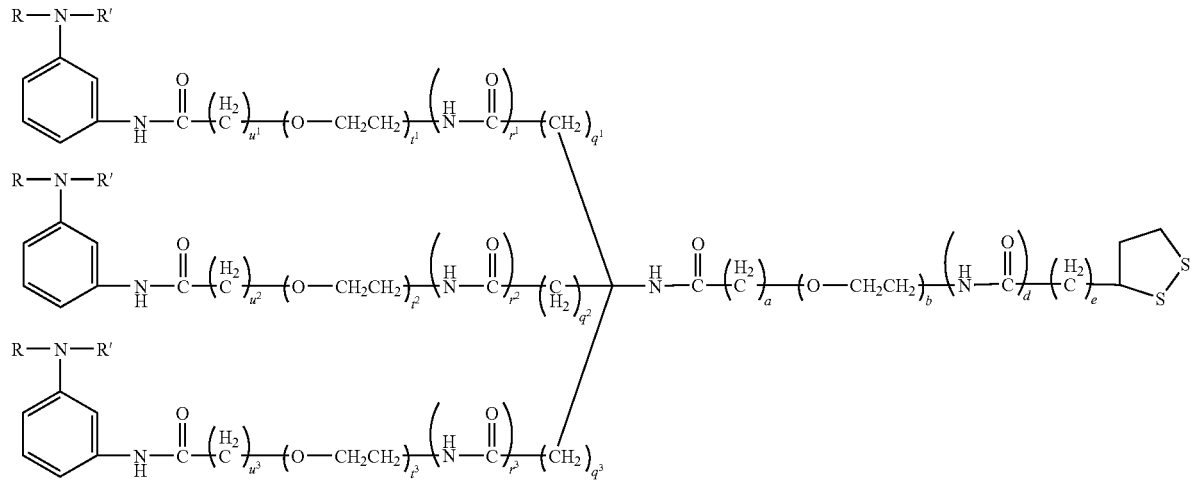

Note that the sugar molecule can be various kinds of sugar molecules having a reducing end.

More specifically, it is preferable that the sugar molecule is a sulfated oligosaccharide having a heparin partial disaccharide structure represented by the following general formula (8).

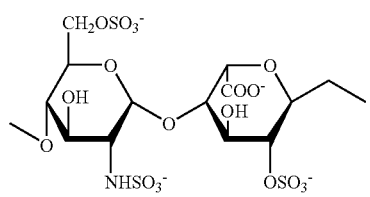

(8)

Further, it is preferable that the sugar molecule is at least one oligosaccharide selected from the group (9).

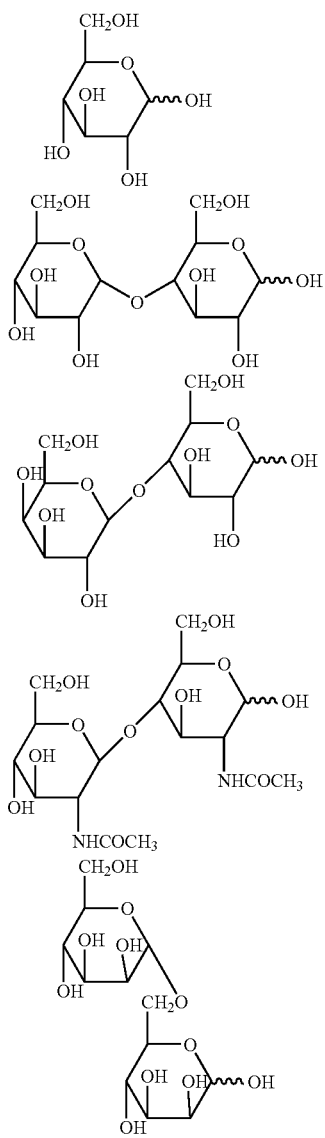

(9)

In order to solve the above problems, a sugar molecule introducing method includes the step of: causing a solution containing the foregoing ligand conjugate to come into contact with a supporter including metal on a surface thereof.

According to the above method, the S—S bond of the linker compound included in the ligand conjugate is converted into a bond with metal on the surface of the supporter, so as to immobilize a sugar chain serving as a ligand onto the surface of the supporter. Therefore, a sugar molecule binding to a linker compound can be arranged on a surface of a supporter by a simple method of causing a solution including a ligand conjugate to come into contact with a supporter.

Further, in order to solve the above problems, a ligand carrier of the present invention comprises the foregoing ligand conjugate immobilized on a supporter including metal on a surface thereof.

According to the above arrangement, since metal-sulfur bond makes it possible to firmly immobilize a ligand conjugate on a surface of the supporter, it is possible to provide a ligand carrier including a plurality of sugar molecules arranged on a surface of a supporter with high reproducibility. Therefore, the use of the ligand carrier makes it possible to observe an interaction between sugar molecules included in a ligand conjugate and substances, such as proteins, which interact with the sugar molecules with high reproducibility. Thus, it is possible to quantitatively evaluate biological activities of sugar molecules.

Additional objects, features, and strengths of the present invention will be made clear by the description below. Further, the advantages of the present invention will be evident from the following explanation in reference to the drawings.

BRIEF DESCRIPTION OF DRAWINGS

FIG. 5(*b*) is a graph showing total reflection infrared absorption spectra of Tetra-GlcNS6S-IdoA2S-Glc at different mixture proportions in a solution.

FIG. 6(*b*) is a graph showing a relative intensity of sulfuric acid group on a chip with respect to a mixture proportion of Tetra-GlcNS6S-IdoA2S-Glc in a solution.

FIG. 7(*b*) is a graph showing a result of observing h-vWF binding interaction by the SPR method when a mixture ratio of Tri-GlcNS6S-IdoA2S-Glc and Mono-Glc was 100:0.

FIG. 7(c) is a graph showing a result of observing h-vWF binding interaction by the SPR method when a mixture ratio of Tetra-GlcNS6S-IdoA2S-Glc and Mono-Glc was 100:0.

FIG. 9(a) is a plot of h-vWF binding amounts obtained from the results shown in FIGS. 7(a) and 8(a) at different concentrations.

FIG. 9(b) is a plot of h-vWF binding amounts obtained from the results shown in FIGS. 7(b) and 8(b) at different concentrations.

FIG. 9(c) is a plot of h-vWF binding amounts obtained from the results shown in FIGS. 7(c) and 8(c) at different concentrations.

BEST MODE FOR CARRYING OUT THE INVENTION

Figure 1:
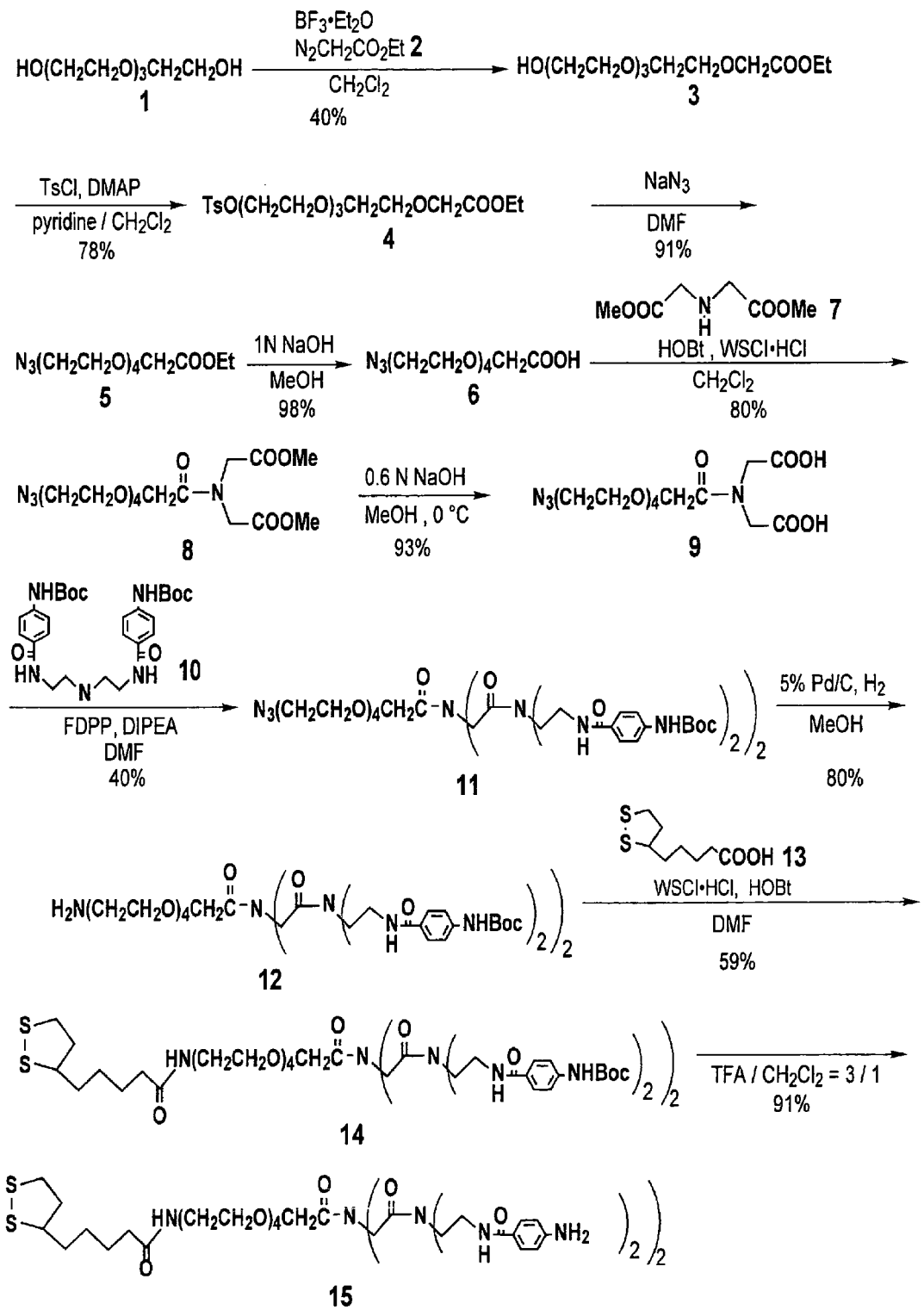
FIG. 1 is a schematic diagram illustrating an example of synthetic pathway of a linker compound (Compound 15) according to the present invention.

The following will describe details of the present invention.

A linker compound of the present invention intervenes between (i) a protein-analyzing supporter, such as a sensor chip of surface plasmon resonance (SPR) and a carrier of affinity chromatography, and (ii) sugar such as oligosaccharide (hereafter referenced to as a sugar molecule), and used to immobilize the sugar molecule onto the supporter. Therefore, the linker compound needs to include a moiety immobilizable onto the supporter and a moiety capable of easily taking in a sugar molecule in molecules of the linker compound.

Moreover, the SPR and affinity chromatography aims at identifying and separating substances which specifically interact with sugar molecules, such as protein. The linker compound therefore must not have a nonspecific interaction with substances such as protein.

Then, the linker compound of the present invention has a disulfide bond (S—S bond) as the moiety immobilizable onto the supporter, as indicated in the general formula (1) or (2). Sulfur (S) constituting the disulfide bond can form a metal-sulfur bond with metal such as gold (Au), for example, with which a surface of the protein-analyzing supporter is coated. This makes it possible to firmly bond to the supporter.

Moreover, in order to arrange a plurality of sugar molecules two-dimensionally onto the surface of the protein-analyzing supporter and to control an interval between separate sugar chains of sugar molecules, the linker compound has a multi-branched structure moiety consisting of a plurality of amino groups as a moiety capable of easily taking in sugar molecules. That is, the multi-branched structure moiety of the linker compound of the present invention is a moiety having a structure represented by X in the general formula (1) or (2). The X, as described previously, has a structure including three or more hydrocarbon derivative chains, wherein the hydrocarbon derivative chains each include an aromatic amino group at an end thereof, and may include a carbon-nitrogen bond or amido bond in a main chain thereof.

Amino group (—$NH_2$ group) of the aromatic amino group is used as reactive group for introducing a sugar molecule of oligosaccharide or like the into linker compound when reductive amination reaction occurs between the amino group and the sugar molecule. Specifically, an aldehyde group (—CHO group) or a ketone group (—CRO group where R means a hydrocarbon group) produced by equilibration within a sugar molecule reacts with the amino group included in the linker compound, thereby forming a Schiff base. A continuous reduction of the Schiff base causes the sugar molecule to be introduced into the aromatic amino group.

Thus, by including three or more hydrocarbon derivative chains as described above, X in general formula (1) or (2) has a multi-branched structure moiety having a plurality of aromatic amino groups capable of taking in sugar molecules. Since sugar molecules of oligosaccharide or the like are introduced into the aromatic amino groups contained in the multi-branched moiety, it is possible to arrange a plurality of sugar molecules two-dimensionally onto the surface of the protein-analyzing supporter with high reproducibility through the linker compound including the structure represented by general formula (1) or (2).

Further, a linker compound of the present invention has an oligoethylene oxide between a disulfide group and the aromatic amino group, as shown in general formula (1) or (2). This makes it possible to reduce a nonspecific hydrophobic interaction as much as possible and to easily adjust a length to the disulfide group subjected to metal bond, thus effectively forming a metal-sulfur bond. In general formula (1), a, b, d, and e can be independently an integer of 0 to 6. In this case, however, when b is 0, X must have an oligoethylene oxide therein. In general formula (2), n is not limited as long as n is an integer of 1 to 6.

As specifically shown in general formula (3), X may have two double-branched structures each formed by two hydrocarbon derivative chains bonding to a nitrogen atom (N) at the opposite end of the aromatic amino groups. The nitrogen atoms of the two double-branched structure bond to a single nitrogen atom (N) through the —CO—CH$_2$— group to form a multi-branched structure. With this, X has a structure serving as a multi-branched moiety including four hydrocarbon derivative chains. It is to be noted, in general formula (3), that $m^1$, $m^2$, $m^3$, and $m^4$ are not limited provided that they are an integer of 1 to 6. The integers represented by $m^1$, $m^2$, $m^3$, and $m^4$ may be mutually different, or may be the same either partly or completely. Above all, in view of ease of production of a compound having the multi-branched moiety, it is preferable that $m^1$ to $m^4$ be mutually the same integer, 2 in particular. Further, $p^1$ and $p^2$ are not limited provided that they are an integer of 1 to 6. The integers represented by $p^1$ and $p^2$ may be mutually different, or may be the same either partly or completely. Above all, in view of ease of production, it is preferable that $p^1$ and $p^2$ be mutually the same integer, 1 in particular.

Note that X including four hydrocarbon derivative chains indicated in general formula (3) can be of a structure having an oligoethylene oxide in each of the hydrocarbon derivative chains. For example, as indicated in general formula (4), X can be of a structure having an oligoethylene oxide between CH$_2$ and NH in each of the hydrocarbon derivative chains.

As shown in general formula (4), X may have a triple-branched structure formed by three hydrocarbon derivative chains bonding to a carbon atom (C) at the opposite end of the aromatic amino groups. In this case, the carbon atoms of the triple-branched structure bond to a single nitrogen atom (N) through the —C—N— group to form a multi-branched structure. With this, X has a structure serving as a multi-branched moiety including three hydrocarbon derivative chains.

It is to be noted, in general formula (4), that $q^1$, $q^2$, and $q^3$ are not limited provided that they are an integer of 0 to 6. The integers represented by $q^1$, $q^2$, and $q^3$ may be mutually different, or may be the same either partly or completely. Above all, in view of ease of production of a compound having the multi-branched moiety, it is preferable that $q^1$ to $q^3$ be mutually the same integer, 2 in particular. Further, $r^1$, $r^2$, and $r^3$ are not limited provided that they are an integer of 0 to 6. The integers represented by $r^1$ to $r^3$ may be mutually different, or may be the same either partly or completely. Above all, in view of ease of production, it is preferable that $r^1$ to $r^2$ be mutually the same integer, 1 in particular. Still further, $u^1$, $u^2$, and $u^3$ are not limited provided that they are an integer of 0 to 6. The integers represented by $u^1$ to $u^3$ may be mutually different, or may be the same either partly or completely. Above all, in view of ease of production, it is preferable that $u^1$ to $u^2$ be mutually the same integer, 1 in particular. Yet further, $t^1$, $t^2$, and $t^3$ are not limited provided that they are an integer of 0 to 6. The integers represented by $t^1$, $t^2$, and $t^3$ may be mutually different, or may be the same either partly or completely. However, in a case where X in general formula (1) is general formula (4), it is preferable that $t^1$, $t^2$, and $t^3$ are an integer of 1 to 6 when b in general formula (1) is 0. In view of ease of production, it is preferable that $t^1$ to $t^3$ be mutually the same integer, 4 in particular.

Thus, X has a structure serving as a multi-branched moiety which causes an atom such as carbon and nitrogen to bind the plurality of hydrocarbon derivative chains so as to form a branched structure. It is to be noted that although it is preferable that the plurality of hydrocarbon derivative chains included in X be all the same, they may have different structures so long as they have an aromatic amino group at an end thereof.

As described above, the linker compound having a structure represented by general formula (1) or (2) includes: S—S bond capable of binding to a protein-analyzing supporter; and an amino group capable of binding to a sugar molecule of oligosaccharide or the like. Therefore, since the linker compound is immobilized onto the protein-analyzing supporter by metal-sulfur bond such as Au—S bond, for example, the linker compound makes it possible to firmly and easily bind a sugar molecule onto the supporter.

Further, the linker compound has a multi-branched moiety and aromatic amino groups at an end thereof. Therefore, with a ligand conjugate (to be mentioned later) which includes the linker compound and a sugar molecule introduced thereinto, sugar molecules can be effectively collected on the surface of the supporter. Also, since the linker compound has a multi-branched moiety, a plurality of sugar molecules can be arranged with high reproducibility when a ligand conjugate including the linker compound is bound with a surface of a supporter.

Moreover, since the linker compound is hardly affected by a nonspecific interaction with a protein, the use of a linker compound of the present invention makes it possible to evaluate biological activities of sugar molecules with high reproducibility.

Further, the above-mentioned linker compound has an oligoethylene oxide between the disulfide group and the aromatic amino group, as shown in general formula (1) or (2). This makes it possible to reduce a nonspecific hydrophobic interaction as much as possible and to easily adjust a length to the disulfide group subjected to metal bond, thus effectively forming a metal-sulfur bond.

The above-mentioned linker compound is produced by a producing method described below. That is, the linker compound is produced by carrying out a condensation reaction between thioctic acid and an amine compound having a multi-branched structure including three or more branched chains each having an aromatic amino group end protected by a protecting group, and deprotecting the protecting group at the aromatic amino group end.

The thioctic acid has a structure represented by the following general formula (10).

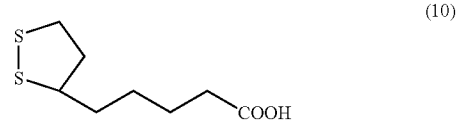

(10)

Further, the amine compound is not particularly limited if it includes a branched chain which has an aromatic amino group end protected by a protecting group. The amine compound only needs to have a structure equivalent to the multi-branched moiety of the linker compound.

Therefore, the branched chain only needs to have a structure included in the hydrocarbon derivative chain except that the branched chain has the aromatic amino group end protected by a protecting group, instead of the aromatic amino group included in the hydrocarbon derivative chain. That is, the branched chain may be modified so that part of the carbon or hydrogen atoms in the hydrocarbon chain consisting of carbon and hydrogen atoms is replaced with other atoms or substituents. More specifically, the branched chain, having an aromatic amino group end protected by a protecting group, may be modified so that part of the carbon-carbon bonds constituting the main chain structure of the hydrocarbon chain is replaced with a carbon-nitrogen bond (C—N bond), a carbon-oxygen bond (C—O bond), or an amide bond (CO—NH bond).

Further, the protecting group is a substituent which is introduced to prevent an amino group of the aromatic amino group from undergoing the condensation reaction. Such a protecting group is not particularly limited provided that it is not affected when deprotecting a protecting group for a secondary amino group. The protecting group is for example a t-butoxycarbonyl group (—COOC($CH_3$)$_3$ group; referred to as a Boc group), a benzyl group, or an arylcarbamate group (—COOCH$_2$CH═CH$_2$, Alloc group).

The amine compound is for example a compound which has a structure represented by following general formula (11).

that bis[2-(2-hydroxyethoxy)ethyl]ether has a structure in which a degree of polymerization is completely controlled, that is, a length is controlled.

The following describe a ligand conjugate of the present invention. Here, the "ligand conjugate" means the one including the aromatic amino group of the linker compound and a sugar molecule introduced therein. In a ligand conjugate of the present invention, a sugar molecule is introduced into the aromatic amino group. This is due to a continuous reduction of the Schiff base formed by the reaction of the amino group of the linker compound with the aldehyde group or ketone group produced by an equilibration within the sugar molecule. That is, the reductive amination reaction binds the linker compound to a sugar molecule.

The sugar molecule included in the ligand conjugate of the present invention is not particularly limited provided that it is a reducing sugar having a reducing end. The sugar molecule is for example a monosaccharide, an oligosaccharide, or a

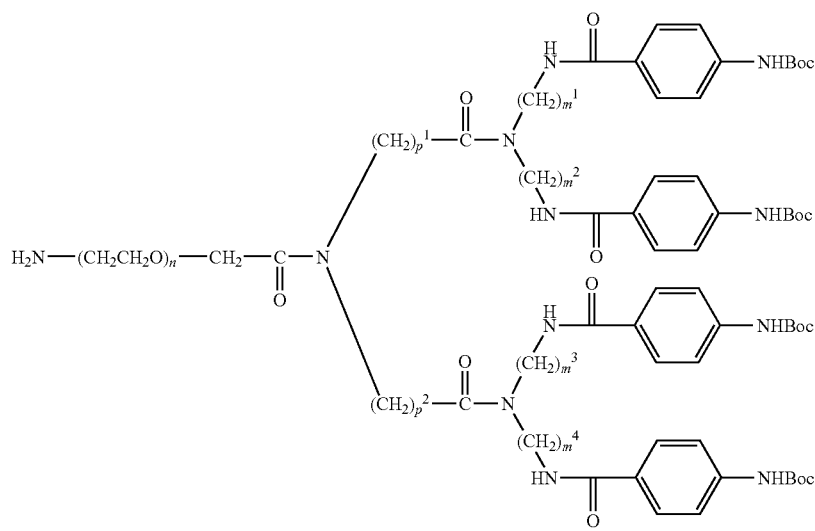

It is to be noted that n, $m^1$ to $m^4$, $p^1$, and $p^2$ in general formula (11) are independently an integer of 1 to 6. A synthesis method of the amine compound will be described in detail in Examples to be mentioned later.

In the condensation reaction of the thioctic acid with the amine compound, a carboxyl group (—COOH group) of the thioctic acid condenses with the amino group (—NH$_2$ group) to form an amide bond. Thereafter, a protecting group of the aromatic amino group end is deprotected and removed to free the aromatic amino group, thereby obtaining the linker compound.

It is to be noted that since the foregoing linker compound has a structure of including oligoethylene oxide in a linker section thereof, as described previously, it is preferable to use a substance including an oligoethylene oxide structure as a material in a production method of the linker compound. Examples of the material include bis[2-(2-hydroxyethoxy)ethyl]ether (Compound 1 in Examples), and commercial polyethylene glycols of different molecular weights (Mw: 200, 300, 400, 600, and 1000) (made from Sigma Corporation). Particularly, it is preferable to use bis[2-(2-hydroxyethoxy)ethyl]ether (Compound 1 in Examples) for the reason polysaccharide. The monosaccharide is for example a glucose, galactose, or mannose. The oligosaccharide is for example a maltose, lactose or a sulfated oligosaccharide to be mentioned later, having two to ten sugar molecules bonding to one another. The polysaccharide is for example a heparin, chondroitin sulfate, or heparan sulfate, having 11 or more sugar molecules including monosaccharides and oligosaccharides.

Further, the oligosaccharide is for example a sulfated oligosaccharide which has a specific partial disaccharide unit (GlcNS6S-IdoA2S), represented by following general formula (8), which is contained in sulfated polysaccharic heparin known for having an anticoagulant activity.

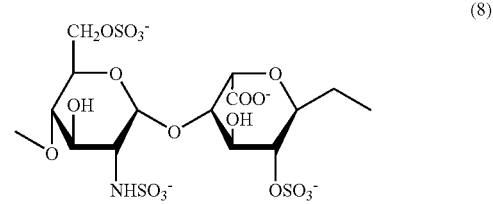

(8)

Another example is an oligosaccharide having a structure represented by following general formula (12), which is the sulfated oligosaccharide having incorporated a glucose into a hydroxyl group which is a reducing end of the sulfated oligosaccharide.

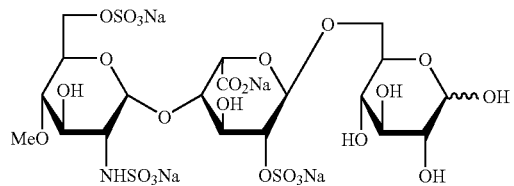

(12)

It is to be noted that the oligosaccharide and the polysaccharide may be a homooligosaccharide or homopolysaccharide consisting of a single monosaccharide, or a complex carbohydrate consisting of different monosaccharides or derivatives thereof, or a conjugated polysaccharide including various monosaccharides or derivatives thereof, and oligosaccharides. Further, the sugar may be natural sugar obtained through isolation and purification from nature, or artificially synthesized sugar.

Specifically, a ligand conjugate of the present invention has a structure represented by general formula (5). The ligand conjugate having a structure represented by general formula (5) is obtained by introducing a sugar molecule into a linker compound represented by general formula (2), where X has a structure represented by general formula (3). The sugar molecule is not limited to a reducing sugar having a reducing end, but is preferably a sugar molecule selected from general formula group (9) and general formula (12). Since X represented by general formula (3) has a structure which includes four hydrocarbon derivative chains, a ligand conjugate which has a structure represented by general formula (5) includes the linker compound and four or more units of sugar molecules bound therewith. It is to be noted, in general formula (5), that $m^1$ to $m^4$, like $m^1$ to $m^4$ in general formula (3), are not limited provided that they are an integer of 1 to 6. The integers represented by $m^1$ to $m^4$ may be mutually different, or may be the same either partly or completely. Further, n is not particularly limited provided that they are an integer of 1 to 6. R' only needs to be a hydrogen atom (H) or an oligosaccharide-derived compound.

Further, a ligand conjugate of the present invention has a structure represented by general formula (7). The ligand conjugate having a structure represented by general formula (7) is obtained by introducing a sugar molecule into a linker compound represented by general formula (1), where X has a structure represented by general formula (4). The sugar molecule is not limited to a reducing sugar having a reducing end, but is preferably a sugar molecule selected from general formula group (9) and general formula (12). Since X represented by general formula (7) has a structure which includes three hydrocarbon derivative chains, a ligand conjugate which has a structure represented by general formula (7) includes the linker compound and three or more units of sugar molecules bound therewith.

Since both of the foregoing ligand conjugates include a linker compound and sugar molecules, S—S bond in the linker compound makes it possible to bind a metal on the surface of the protein-analyzing supporter by a metal-sulfur (S) bond, e.g. gold-sulfur (Au—S) bond. With this arrangement, the use of the Au—S bond makes it possible to provide a ligand carrier including three or more sugar molecules collected or immobilized on the surface of the supporter. Therefore, the use of the ligand conjugate makes it possible to arrange a plurality of sugar molecules two-dimensionally onto a surface of the protein-analyzing supporter, for example, with high reproducibility, thus obtaining a ligand carrier. Then, the use of the obtained ligand carrier makes it possible to evaluate biological activities of sugar molecules with high reproducibility. Note that for the metal on the surface of the supporter, metal such as Cu, Ag, or Pt, as well as Au, can be used. Particularly, Au is preferable.

Further, the foregoing linker compound has an oligoethylene oxide in a linker thereof. This makes it possible to reduce a nonspecific hydrophobic interaction as much as possible and to easily adjust a length to the disulfide group subjected to metal bond, thus effectively forming a metal-sulfur bond.

Thus, the present invention also includes a ligand carrier including the ligand conjugate of the present invention immobilized on a surface of a supporter through a metal-sulfur bond. The applicable field of the ligand carrier is not limited to the protein analysis. For example, the ligand carrier can be used for analyzing substances other than a protein so as to examine an interaction with sugar molecules.

The ligand carrier makes contact between a solution including the ligand conjugate and a supporter having a metal film on a surface thereof, so that S atoms of the S—S bond in the ligand conjugate are bound to a metal on the surface of the supporter by metal-sulfur bond, and the ligand conjugate is introduced on the surface of the supporter. More specifically, the protein-analyzing supporter is soaked into the ligand conjugate solution for a predetermined period of time, or the ligand conjugate solution is injected to the supporter (the ligand conjugate solution is flown onto the surface of the supporter), so that the S—S bond of the linker compound included in the ligand conjugate is converted into an Au—S bond, such as a bond with gold on the surface of the supporter, thereby making it possible to immobilize the ligand conjugate on the surface of the supporter.

Although a solvent used for the ligand conjugate solution is not particularly limited, methanol, water, dimethylacetamide (DMAc), a mixture solvent of these substances can be for example used. In case of immersion in the ligand solution, the duration of immersion only needs to be about 0.5 to 12 hours. In case of injection of the ligand solution, a concentration of the ligand conjugate solution injected only needs to be 1 µM to 1 mM.

Thus, since a ligand conjugate of the present invention has an S—S bond, the ligand conjugate allows for easy immobilization onto the surface of the protein-analyzing supporter and easy introduction of sugar molecules onto the supporter.

Note that the present invention also includes the above method of introducing sugar molecules into the supporter.

A ligand carrier of the present invention is applicable to analysis of an interaction between a sugar molecule and other substance such as a protein, for example. More specifically, the ligand carrier can be applied to SPR measurement, affinity chromatography, or the like.

For example, an SPR measurement for protein analysis is carried out as follows. That is, if a ligand carrier including a ligand conjugate of the present invention immobilized on a supporter where metal thin film such as gold thin film is deposited is used to bring the ligand carrier into contact with a protein so as to measure a resonant angle with a surface plasmon resonance apparatus in the usual manner, the binding behavior of the ligand carrier with the protein can be observed. It is to be noted that glass, plastic, or the like can be used to form the carrier (sensor chip) used for an SPR measurement. Particularly, glass is suitably used. Further, a ligand carrier can be brought into contact with a protein by flowing a solution including a running buffer and a protein dissolved therein onto a surface of the ligand carrier, or by immersing the ligand carrier in the solution including the running buffer solution and the protein dissolved therein. The running buffer is for example a phosphate buffer solution.

Since a ligand carrier of the present invention has the foregoing ligand conjugate, a plurality of sugar molecules are arranged two-dimensionally on a surface of a supporter with high reproducibility. This makes it possible to observe a biological activity of a sugar molecule with high reproducibility, thereby making it possible to reveal a structure of a sugar molecule and quantitatively evaluate a biological activity of a sugar molecule.

Further, a sensor chip including a sugar molecule immobilized thereon, as a ligand carrier of the present invention, can be used for, for example, an SPR measurement described below. That is, it is possible to observe an interaction between sugar molecules by comparing a detection result of an SPR measurement obtained by using the first sensor chip which has a first sugar molecule immobilized on a surface of a supporter with a detection result of an SPR measurement obtained by using the second sensor chip which a second sugar molecule wholse end structure is different from that of the first sugar molecule and immobilized on a surface of the supporter. The sensor chips only need to be formed of ligand conjugates having different sugar molecules immobilized thereon. Sugar molecules to be compared with each other are for example lactose and glucose, maltose and glucose, and kojibiose and glucose. Although two sensor chips are used here, two or more sensor chips having different types of sugar molecules introduced thereon may be used. It is to be noted that the end of a sugar molecule means the side not immobilized onto a sensor chip.

In the above SPR measurement, a protein which specifically interacts with the first sugar molecule is used to act on the two sensor chips under constant measurement conditions so as to observe resonant angles of the two sensor chips. By comparing between the resonance angles of the two sensor chips, a specific interaction between a sugar molecule and a protein or the like can be measured.

Also, a substance whose interaction with a sugar molecule is observed is not limited to a protein.

In the above arrangement, two kinds of sensor chips are simultaneously measured. However, this is not for limitation. More than two sensor chips may be measured and do not need to be measured simultaneously. Also, at least one sensor chip not including a sugar molecule introduced thereon may be used. For example, a sensor chip including only a linker compound immobilized thereon may be used.

The above SPR measurement enables a measurement using at least two sensor chips including immobilized ligand conjugates of the same structure except for sugar molecules. A difference in a degree of an interaction measured by using at least two sensor chips is observed as resulting from sugar molecules. Thus, the above measurement method, suppressing a nonspecific interaction with another substance, makes it possible to measure a specific interaction of a sugar molecule with another substance.

EXAMPLES

The following will describe details of synthesis of a linker compound and a ligand conjugate of the present invention. In these Examples, experiments of comparative study of a synthesized ligand conjugate and another ligand conjugate were carried out and explained below.

Example 1

Synthesis of Linker Compound (Compound 15)

One of linker compounds according to the present invention, i.e. a linker compound (Compound 15) having a structure represented by general formula (2) where n is 4, X is represented by general formula (3), wherein $p^1$ and $p^2$ are 1, $m^1$, $m^2$, $m^3$, $m^4$ are 2, was synthesized according to the following procedure. FIG. 1 illustrates a process of synthesizing the linker compound (Compound 15). Note that reference numerals given to compounds in the description of Example 1 correspond to reference numerals shown in FIG. 1.

As illustrated in FIG. 1, first of all, bis[2-(2-hydroxyethoxy)ethyl]ether (Compound 1) as a raw material was brought into reaction with ethyl diazoacetate (Compound 2) in dichloromethane in the presence of $BF_3 \cdot Et_2O$ to synthesize an ester compound (Compound 3) at the yield of 40%. Then, Compound 3 was brought into reaction with p-toluenesulfonyl chloride in dichloromethane in the presence of DMAP and pyridine to obtain a tosyl compound (Compound 4) at the yield of 78%. Compound 4 was caused to act with sodium azide in N,N-dimethylformamide to obtain an azide compound (Compound 5) at the yield of 90%.

Compound 5 was hydrolyzed with 1N NaOH in methanol to obtain a carboxylic acid derivative (Compound 6) at the yield of 98%. Compound 6 and Compound 7 were condensed in dichloromethane by using HOBt, EDC.HCl to obtain a diester derivative (Compound 8) at the yield of 80%. Compound 8 was hydrolyzed with 0.6N NaOH in methanol to obtain a dicarboxylic acid derivative (Compound 9) at the yield of 93%. Compound 9 and a diamine derivative (Compound 10) were condensed by using FDPP and DIPEA to obtain Compound 11 at the yield of 40%. An azido group of Compound 11 was subjected to catalytic hydrogen reduction to obtain an amine compound (Compound 12) at the yield of 80%.

Thereafter, Compound 12 was condensed with thioctic acid (Compound 13) to obtain Compound 14 at the yield of 59%. Finally, Compound 14 is caused to act on TFA to deprotect a Boc group and then obtain a linker compound (Compound 15) having four units of target aromatic amino groups as an object at the yield of 91%.

The following will describe more specifically a synthesis method of the compounds obtained in the foregoing synthesis process, and results of $^1$H-NMR spectrum measurement and mass spectrometry measurement regarding the synthesized compounds. A relative concentration of a sugar molecule on a tip as a ligand was obtained by measuring a total reflection FT-IR (ATR-FT-IR). These were carried out according to the following procedures.

[$^1$H-NMR Spectrum, Mass Spectrometry, ATR-FT-IR Measurement, Reagents, and Others]

For $^1$H-NMR spectrum measurement, JEOL-JNM-Lambda-500 NMR spectrometer, JEOL JNM-GSX400 NMR spectrometer, JEOL EX-270 NMR spectrometer were used. Chemical shifts in $CDCl_3$ are expressed in δ-values in accordance with chemical shift of tetramethylsilane as a reference substance. Chemical shifts in $CD_3OD$ and DMSO-$d_6$ are expressed in δ-values in accordance with chemical shift of proton of a remaining solvent used as a reference substance. Mass spectrometry was measured by using Applied Biosystems, Mariner™. For an ATR-FT-IR measurement, Shimadzu, IRPrestige-21 was used with a single-reflection ATR-accessory unit (MIRacle Ge Prism). A sensor chip used for an ATR-FT-IR measurement was the same as a sensor chip for an SPR measurement. For a Medium-pressure column silica gel chromatography, Silica gel 60 No. 9385 (Merck) was used. For thin layer silica gel chromatography, Silica gel 60 F254 (Merck) was used. An anhydrous dichloromethane was obtained by distillation in the air of nitrogen by using calcium hydride serving as a drying agent. For other dehydrating solvent, a product made from Kanto Chemical Co. Ltd. was purchased to use. For other reagent and solvent, high-grade products were used.

(1) Synthesis of Compound 3

Bis[2-(2-hydroxyethoxy)ethyl]ether (Compound 1) (14.57 ml, 80 mmol) and $BF_3.Et_2O$ (252 ml, 2 mmol) were dissolved in 50 ml of anhydrous dichloromethane, subjected to dropping of ethyl diazoacetate (Compound 2)(1.8 ml, 17.35 mmol) at 0° C., and then stirred for 70 minutes at room temperature. To a reaction solution, 20 ml of a saturated aqueous solution of ammonium chloride was added. Extraction with dichloromethane was performed, and the extract was dried with an anhydrous magnesium sulfate. The drying agent was filtered out from the dried residue to obtain a filtrate. The filtrate was concentrated under reduced pressure to obtain a residue. The residue was purified by medium-pressure preparative chromatography (600 g, hexane:ethyl acetate=1:3) to obtain a colorless liquid serving as Compound 3 (2.26 g, yield of 47%).

$^1$H-NMR (400 MHz, $CDCl^3$) measurement was conducted on Compound 3 so obtained to find that δ4.22 (2H, q, J=7.0, 14.2 Hz, $CO_2CH_2$), 4.14 (2H, s, $OCH_2CO$), 3.75-3.62 (14H, m, $CH_2CH_2O×3$, $HOCH_2CH_2$), 3.61 (2H, t, J=4.4 Hz, HOC$H_2$), 1.84 (1H, bs, O$H$), 1.28 (3H, t, J=7.3 Hz, $CH_2CH_3$). An ESI-MS (positive) measurement was conducted on Compound 3 to find that the m/z was 303.27[(M+Na)$^+$]. This could examine a structure of Compound 3. It is to be noted that a molecular mass of the Compound 3 is $C_{12}H_{24}O_7$:280.15.

(2) Synthesis of Compound 4

The ethyl compound 3 (2.15 g, 7.66 mmol) and DMAP (41.7 mg, 337 mmol) were dissolved in 8 ml of anhydrous pyridine. The mixture solution was subjected to dropping of a solution in which p-toluenesulfonate chloride (1.75 g, 9.19 mmol) was dissolved in 8 ml of anhydrous dichloromethane at 0° C., and stirred for three hours at room temperature. To the reaction solution, dichloromethane and iced water were added. An organic phase was extracted into dichloromethane from the mixture solution. The organic phase washed once each by a saturated aqueous solution of sodium bicarbonate, water, and a saturated saline solution, and dried with an anhydrous magnesium sulfate. The drying agent was filtered out from the dried residue to obtain a filtrate. The filtrate was concentrated under reduced pressure to obtain a residue. The residue was purified by medium-pressure preparative chromatography (100 g, chloroform:acetone=4:1) to obtain a yellow liquid serving as Compound 4 (2.59 g, yield of 78%).

$^1$H-NMR (400 MHz, $CDCl_3$) measurement was conducted on Compound 4 so obtained to find that δ7.80 (2H, d, J=8.4 Hz, aromatic), 7.35 (2H, d, J=8.4 Hz, aromatic), 4.21 (2H, q, $CO_2CH_2$), 4.16 (2H, t, J=4.8 Hz, TsOC$H_2$), 4.14 (2H, s, OC$H_2$CO), 3.76-3.59 (14H, m, $CH_2CH_2O×3$, $TsOCH_2CH_2$), 2.45 (3H, s, $CH_3Ar$), 1.28 (3H, t, J=7.0 Hz, $CH_2CH_3$). An ESI-MS (positive) measurement was conducted on Compound 4 to find that the m/z was 457.16[(M+Na)$^+$]. This could examine a structure of Compound 4. It is to be noted that a molecular mass of the Compound 4 is $C_{19}H_{30}O_9S$: 434.16.

(3) Synthesis of Compound 5

The tosyl compound 4 (1.01 g, 2.31 mmol) and sodium azide (1.53 g, 2.31 mmol) were dissolved in 50 ml of anhydrous dimethylformamide and stirred in a shade for 10 hours under nitrogen atmosphere at 120° C. An organic phase was extracted from the reaction solution with chloroform, and washed once each by water and a saturated saline solution, and dried with an anhydrous magnesium sulfate. The drying agent was filtered out from the dried residue to obtain a filtrate. The filtrate was concentrated under reduced pressure to obtain a residue. The residue was purified by medium-pressure preparative chromatography (10 g, chloroform:acetone=2:1) to obtain a yellow liquid serving as Compound 5 (638 mg, yield of 90%).

$^1$H-NMR (400 MHz, $CDCl_3$) measurement was conducted on Compound 5 so obtained to find that δ4.22 (2H, q, J=7.3 Hz, $CO_2CH_2$), 4.15 (2H, s, $OCH_2CO_2Et$), 3.75-3.63 (12H, m, $OCH_2CH_2O$), 3.69 (2H, m, $N_3CH_2CH_2$), 3.39 (2H, t, J=5.1 Hz, $N_3CH_2$), 1.29 (3H, t, J=7.3 Hz, $CO_2CH_2CH_3$). An ESI-MS (positive) measurement was conducted on Compound 5 to find that the m/z was 328.14[(M+Na)$^+$]. This could examine a structure of Compound 5. It is to be noted that a molecular mass of the Compound 5 is $C_{12}H_{23}N_3O_6$: 305.16.

(4) Synthesis of Compound 6

The above azide compound 5 (614 mg, 2.01 mmol) was dissolved in 24 ml of methanol. 4.3 ml of 1N NaOH was added to the mixture at 0° C. in a shade. Thereafter, the mixture was stirred for 21 hours at room temperature. The reaction solution was concentrated under reduced pressure to obtain a residue. After chloroform was added to the residue, 1N HCl was added to the residue until the pH of the residue becomes 2. Then, an organic phase was extracted with chloroform. The organic phase washed once by a saturated saline solution, and dried with an anhydrous magnesium sulfate. The drying agent was filtered out from the dried residue to obtain a filtrate. The filtrate was concentrated under reduced pressure to obtain a colorless liquid serving as Compound 6 (549 mg, yield of 90%).

$^1$H-NMR (400 MHz, $CDCl_3$) measurement was conducted on Compound 6 so obtained to find that δ6.19 (1H, bs, $CO_2H$), 4.16 (2H, s, $OCH_2CO_2H$), 3.75-3.64 (12H, m, $OCH_2CH_2O$), 3.68 (2H, m, $N_3CH_2CH_2$), 3.41 (2H, t, J=5.1 Hz, $N_3CH_2$). An ESI-MS (positive) measurement was conducted on Compound 6 to find that the m/z was 328.14[(M+Na)$^+$]. This could examine a structure of Compound 6. It is to be noted that a molecular mass of the Compound 6 is $C_{10}H_{19}N_3O_6$: 277.13.

(5) Synthesis of Compound 7

Iminodiacetate (10.0 g, 75.1 mmol) and $BF_3.OEt_2$ (22 ml, 173 mmol) were dissolved in anhydrous methanol (50 ml) and flown for 5 hours under argon atmosphere. Then, the mixture solution was neutralized with a saturated aqueous sodium bicarbonate solution, and extraction with chloroform was performed. Triethylamine was added to an aqueous phase until the pH thereof becomes 9, and extraction with chloroform was performed again. The extract was dried with an anhydrous sodium sulfate as a drying agent. Thereafter, the drying agent was filtered out from the dried residue to obtain a filtrate. The filtrate was concentrated under reduced pressure to obtain a yellow oily object serving as Compound 7 (9.61 g, yield of 79%).

$^1$H-NMR (400 MHz, $CDCl_3$) measurement was conducted on Compound 7 so obtained to find that δ3.74 (6H, s, OMe), 3.48 (4H, s, $CH_2N$), 2.00 (1H, s, NH). An ESI-MS (positive) measurement was conducted on Compound 7 to find that the m/z was 162.1[(M+H)$^+$]. This could examine a structure of Compound 7. It is to be noted that a molecular mass of the Compound 7 is $C_6H_{11}NO_2$: 161.07.

(6) Synthesis of Compound 8

The Compound 6 (0.35 g, 1.26 mmol), EDC.HCl (0.27 g, 1.39 mmol), and HOBt (0.19 g, 1.39 mmol) were dissolved in 2 ml of anhydrous dichloromethane. The mixture was stirred for 80 minutes at 0° C. in a shade under argon atmosphere. Thereafter, a solution including the Compound 7(1.42 g, 6.83 mmol) dissolved in 1 ml of anhydrous dichloromethane 1 was added to the mixture, and the mixture was stirred for 17 hours at room temperature. An organic phase was extracted with chloroform from the reaction solution. The organic phase was washed once each by 10% citric acid and a saturated aqueous solution of sodium bicarbonate. The resultant was dried with anhydrous sodium sulfate as a drying agent. Then, the drying agent was filtered out from the dried residue to obtain a filtrate. The filtrate was concentrated under reduced pressure to obtain a residue. The residue was purified by preparative silica gel chromatography (50 g, chloroform:acetone=10:1) to obtain a white solid serving as Compound 8 (0.42 g, yield of 80%).

$^1$H-NMR (400 MHz, CDCl$_3$) measurement was conducted on Compound 8 so obtained to find that δ4.23, 4.11 (4H, s, s, CONCH$_2$), 4.18 (2H, s, OCH$_2$CON), 3.69, 3.66 (4H, S, S, CO$_2$CH$_3$), 3.69-3.56 (12H, m, OCH$_2$CH$_2$O), 3.61 (2H, t, J=5.1 Hz, N$_3$CH$_2$CH$_2$), 3.32 (3H, t, J=5.0 Hz, N$_3$CH$_2$). An ESI-MS (positive) measurement was conducted on Compound 8 to find that the m/z was 443.17[(M+Na)+]. This could examine a structure of Compound 8. It is to be noted that a molecular mass of the Compound 8 is C$_{16}$H$_{28}$N$_4$O$_9$: 420.19.

(7) Synthesis of Compound 9

The Compound 8 (398 mg, 947 μmol) was dissolved in methanol (5 ml), mixed with 2N NaOH (2.1 ml), and stirred for 2.5 hours at 0° C. Thereafter, the mixture solution was mixed with Dowex 50WX-8 (H$^+$ form) until the pH becomes 2 for neutralization. The Dowex 50WX-8 was filtered out and separated from the neutralized solution to obtain a filtrate. The filtrate was concentrated under reduced pressure to obtain a residue. The residue obtained by concentration under reduced pressure was mixed with water, and an insoluble object is filtered out and separated from the residue. The filtrate was concentrated under reduced pressure and freeze-dried to obtain a white solid serving as Compound 9 (346 mg, yield of 93%).

$^1$H-NMR (400 MHz, CDCl$_3$) measurement was conducted on Compound 9 so obtained to find that δ5.66 (2H, bs, CO$_2$H×2), 4.26 (2H, s, OCH$_2$CON), 4.24, 4.18 (4H, s, s, CONCH$_2$), 3.71-3.63 (12H, m, OCH$_2$CH$_2$O), 3.67 (2H, m, J=5.1 Hz, N$_3$CH$_2$CH$_2$), 3.40 (3H, t, J=4.9 Hz, N$_3$CH$_2$). An ESI-MS (positive) measurement was conducted on Compound 9 to find that the m/z was 391.15[(M−H)$^-$]. This could examine a structure of Compound 9. It is to be noted that a molecular mass of the Compound 9 is C$_{14}$H$_{24}$N$_4$O$_9$: 392.15.

(8) Synthesis of Compound 10

N-Boc aminobenzoic acid derivative (3.33 g, 14.0 mmol) and HOBt (1.93 g, 14.3 mmol) were suspended in anhydrous dichloromethane (60 ml), stirred for 15 minutes at 0° C. under argon atmosphere. The stirred solution was mixed with a solution including EDC.HCl (2.87 g, 15.0 mmol) dissolved in anhydrous dichloromethane (30 ml) and stirred for 50 minutes. The mixture solution was mixed with diethylene triamine (0.79 ml, 7.00 mmol), and stirred overnight at room temperature in a shade to obtain a white crystal. The white crystal filtered out and obtained was recrystallized from methanol to obtain a white crystal serving as Compound 10 (3.53 g, yield of 92.9%).

$^1$H-NMR (400 MHz, CDCl$_3$) measurement was conducted on Compound 10 so obtained to find that δ7.77-7.74 (4H, d, J=8.67 Hz, aromatic), 7.50-7.48(4H, d, J=8.57 Hz, aromatic), 3.70-3.66 (4H, m, J=5.19 Hz CONHCH$_2$), 3.34-3.28 (4H, m, J=5.61 Hz CH$_2$CH$_2$ONH), 1.53 (18H, s, CH$_3$). An ESI-MS (positive) measurement was conducted on Compound 10 to find that the m/z was 542.4[(M+H)$^+$]. This could examine a structure of Compound 10. It is to be noted that a molecular mass of the Compound 10 is C$_{28}$H$_{39}$N$_5$O$_6$: 541.29.

(9) Synthesis of Compound 11

The Compound 9 (333 mg, 847 μmol), diisopropylethylamine (435 ml, 2.54 mmol), and FDPP (1.00 g, 2.60 mmol) were dissolved in anhydrous dimethylformamide (5 ml) and stirred for 30 minutes at 0° C. under argon atmosphere in a shade. Then, the stirred solution was mixed with a solution including Compound 10 (1.15 g, 2.11 mmol) dissolved in anhydrous dimethylformamide (11 ml) and stirred for 20 hours at room temperature. The reaction solution was concentrated under reduced pressure to obtain a residue. An organic phase and an aqueous phase were extracted with chloroform from the residue. Both the aqueous phase and the organic phase were washed once each by 10% citric acid and a saturated aqueous solution of sodium bicarbonate. The resultant was dried with anhydrous magnesium sulfate as a drying agent. Then, the drying agent was filtered out from the dried residue to obtain a filtrate. The filtrate was concentrated under reduced pressure to obtain a residue. The residue was purified by preparative silica gel chromatography (80 g, chloroform:methanol=10:1) to obtain a white solid serving as Compound 11 (125 mg, yield of 59%).

$^1$H-NMR (400 MHz, CDCl$_3$) measurement was conducted on Compound 11 so obtained to find that δ8.18 (1H, bs, NHCOPh), 7.86 (2H, d, J=8.4 Hz, aromatic), 7.80 (1H, bs, PhNHCO), 7.75-7.68 (8H, m, NHCOPh, aromatic, PhNHCO), 7.54 (1H, bs, PhNHCO), 7.48 (2H, d, J=8.4 Hz, NHCOPh, aromatic), 7.42 (5H, m, aromatic, NHCOPh), 7.34 (2H, d, J=8.8 Hz, aromatic), 7.28 (1H, bs, PhNHCO), 3.84 (4H, bs, CONCH$_2$), 3.62-3.48 (20H, m, OCH$_2$CH$_2$O, NCH$_2$CH$_2$NH), 3.56 (2H, t, J=5.1 Hz, N$_3$CH$_2$CH$_2$), 3.43 (2H, bs, OCH$_2$CON), 3.35-3.30 (4H, m, NCH$_2$CH$_2$NH), 3.26 (2H, t, J=5.1 Hz, N$_3$CH$_2$), 3.13, 2.98 (4H, bs, bs, NCH$_2$CH$_2$NH), 1.52, 1.50, 1.49 (36H, s, s, s, t-butyl). An ESI-MS (positive) measurement was conducted on Compound 11 to find that the m/z was 1461.72[(M+Na)$^+$]. This could examine a structure of Compound 11. It is to be noted that a molecular mass of the Compound 11 is C$_{70}$H$_{98}$N$_{14}$O$_{19}$: 1438.71.

(10) Synthesis of Compound 12

The Compound 11 (165 mg, 114 μmol) was dissolved in methanol (12 ml), mixed with 5% Pd/C (55 mg), and stirred for 5 hours at room temperature under hydrogen atmosphere. Then, Pd/C was filtered out from the mixture solution to obtain a filtrate. The filtrate was concentrated under reduced pressure to obtain a residue. The residue was purified by preparative silica gel chromatography (10 g, chloroform:methanol=7:1) to obtain a white solid serving as Compound 12 (128 mg, yield of 79%).

$^1$H-NMR (400 MHz, CDCl$_3$) measurement was conducted on Compound 12 so obtained to find that δ7.78-7.68 (8H, m, aromatic), 7.48 (8H, m, aromatic), 4.21, 4.10 (4H, bs, bs, CONCH$_2$), 3.85 (2H, bs, OCH$_2$CON), 3.62-3.44 (26H, m, OCH$_2$CH$_2$O, NCH$_2$CH$_2$NH, NCH$_2$CH$_2$NH), 3.50 (2H, t, J=5.1 Hz, H$_2$NCH$_2$CH$_2$), 2.76 (2H, t, J=5.1 Hz, H$_2$NCH$_2$CH$_2$), 1.50 (36H, s, t-butyl). An ESI-MS (positive) measurement was conducted on Compound 12 to find that the m/z was 1413.74[(M+H)$^+$]. It is to be noted that a molecular mass of the Compound 12 is C$_{70}$H$_{100}$N$_{12}$O$_{19}$: 1412.72.

The Compound 12 is an amine compound having a structure represented by general formula (11) wherein n is 4, p$^1$ and p$^2$ are 1, and m$^1$, m$^2$, m$^3$, and m$^4$ are 2.

(11) Synthesis of Compound 14

The Compound 13 (thioctic acid) (3.4 mg, 16.6.mol), HOBt (1.6 mg, 16.6 μmol), and EDC.HCl (3.2 mg, 1.66 μmol) were dissolved in anhydrous dimethylformamide (2 ml) and stirred at 0° C. under argon atmosphere in a shade. The mixture solution was mixed with a solution including Compound 12 (23.5 mg, 16.6 μmol) dissolved in anhydrous dimethylformamide (2 ml) and stirred for 22 hours at room temperature. The reaction solution was concentrated under reduced pressure to obtain a residue. An organic phase was extracted with dichloromethane from the residue. The organic phase washed once each by 10% citric acid and a saturated aqueous solution of sodium bicarbonate. The resultant was dried with anhydrous sodium sulfate as a drying agent. Subsequently, the drying agent was filtered out from the dried residue to obtain a filtrate. The filtrate was concentrated under reduced pressure to obtain a residue. The residue was purified by preparative silica gel chromatography (7 g, chloroform:methanol=10:1) to obtain a white solid serving as Compound 14 (15.7 mg, yield of 59%).

$^1$H-NMR (400 MHz, CDCl$_3$) measurement was conducted on Compound 14 so obtained to find that δ8.20, 8.00 (4H, bs, bs, N$\underline{H}$COPh), 7.86 (2H, d, J=8.8 Hz, aromatic), 7.77-7.72 (7H, m, COPhNH, aromatic), 7.53 (1H, bs, N$\underline{H}$COPh), 7.50-7.36 (10H, m, aromatic, J=8.8 Hz, COPhN$\underline{H}$), 7.27 (2H, bs, COPhN$\underline{H}$, CONH$\underline{C}$H$_2$), 3.89 (4H, bs, CONC$\underline{H}_2$CO), 3.64-3.37 (26H, m, NCH$_2$C$\underline{H}_2$NH, NC$\underline{H}_2$CH$_2$NH, OC$\underline{H}_2$C$\underline{H}_2$O, CONHC$\underline{H}_2$, CONHCH$_2$C$\underline{H}_2$), 3.53 (1H, m, SSC$\underline{H}$), 3.48 (2H, m, NC$\underline{H}_2$CH$_2$NH), 3.32 (4H, m, OC$\underline{H}_2$CON, NC$\underline{H}_2$CH$_2$NH), 3.18, 2.85 (4H, bs, bs, NC$\underline{H}_2$CH$_2$NH), 3.17-3.04 (2H, m, C$\underline{H}_2$SSCH), 2.44-2.36 (1H, m, C$\underline{H}_2$CH$_2$SS), 2.16 (2H, m, C$\underline{H}_2$CH$_2$C$\underline{H}_2$CONH), 1.89-1.81 (1H, m, C$\underline{H}_2$CH$_2$SS), 1.69-1.56 (4H, m, CH$_2$C$\underline{H}_2$CH$_2$CONH, C$\underline{H}_2$CH$_2$CH$_2$CONH), 1.51, 1.50 (36H, s, s, t-butyl), 1.42-1.34 (2H, m, C$\underline{H}_2$CH$_2$CH$_2$CONH). An ESI-MS (positive) measurement was conducted on Compound 14 to find that the m/z was 1601.81[(M+H)$^+$]. This could examine a structure of Compound 14. It is to be noted that a molecular mass of the Compound 14 is C$_{78}$H$_{112}$N$_{12}$O$_{20}$S$_2$: 1600.76.

(12) Synthesis of Linker Compound (Compound 15)

The Compound 14 (60.3 mg, 31.2 μmol) was dissolved in dichloromethane (1 ml), mixed with TFA (3 ml), and stirred for one hour at 0° C. in a shade. Subsequently, the mixture solution was concentrated under reduced pressure to obtain a residue. The residue was dissolved in methanol, and the mixture solution was poured into a column (1.0 cm Φ×3.0 cm) having Dowex Marathon A (OH$^-$ form) filled therein to carry out ion exchange. The eluate was concentrated under reduced pressure to obtain a white solid serving as Compound 15 (41.2 mg, yield of 91%).

$^1$H-NMR (400 MHz, DMSO-d$_3$) measurement was conducted on Compound 15 so obtained to find that δ8.19, 8.05 (4H, m, m, N$\underline{H}$COPh), 7.82 (1H, bt, CONH$\underline{C}$H$_2$), 7.53 (8H, m, aromatic), 6.51 (8H, dd, J=8.4, 1.5 Hz, aromatic), 5.61-5.55 (8H, m, N$\underline{H}_2$), 4.24, 4.11 (4H, s, s, CONC$\underline{H}_2$CO), 3.93 (2H, bs, OC$\underline{H}_2$CON), 3.60-3.37 (31H, m, NCH$_2$C$\underline{H}_2$NH, NC$\underline{H}_2$CH$_2$NH, OC$\underline{H}_2$C$\underline{H}_2$O, CONHC$\underline{H}_2$, CONHCH$_2$C$\underline{H}_2$, SSCH), 3.19-3.06 (4H, m, CONHC$\underline{H}_2$CH$_2$, C$\underline{H}_2$SSCH), 2.42-2.32 (1H, m, C$\underline{H}_2$CH$_2$SS), 2.04 (2H, m, CH$_2$C$\underline{H}_2$CH$_2$CONH), 1.87-1.78 (1H, m, CH$_2$CH$_2$SS), 1.64-1.45 (4H, m, CH$_2$C$\underline{H}_2$CH$_2$CONH, C$\underline{H}_2$CH$_2$CH$_2$CONH), 1.34-1.28 (2H, m, C$\underline{H}_2$CH$_2$CH$_2$CONH). An ESI-MS (positive) measurement was conducted on Compound 15 to find that the m/z was 623.27[(M+2Na)$^{2+}$]. It is to be noted that a molecular mass of the Compound 15 is C$_{58}$H$_{80}$N$_{12}$O$_{12}$S$_2$: 1200.55.

The Compound 15 is a linker compound having a structure represented by general formula (2) where n is 4, X is represented by general formula (3), wherein p$^1$ and p$^2$ are 1, and m$^1$, m$^2$, m$^3$, and m$^4$ are 2.

Example 2

Synthesis of Ligand Conjugate (Compound 17)

Figure 2:
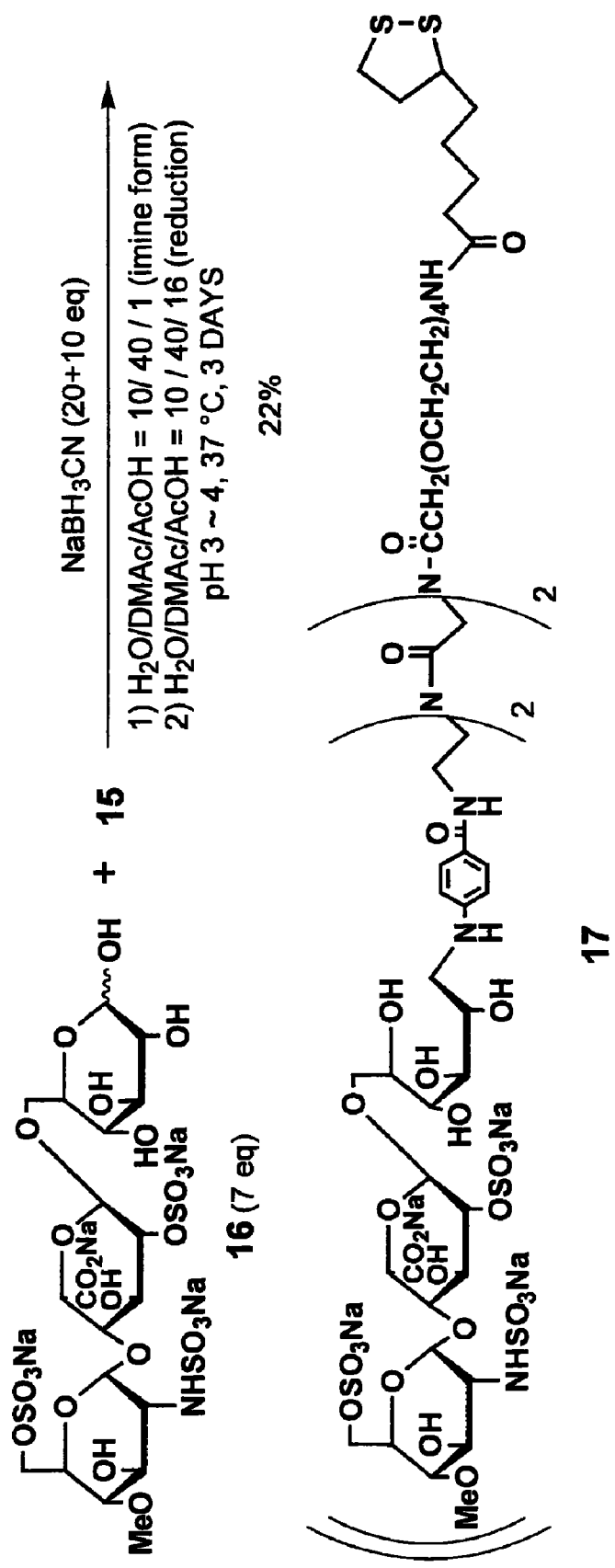
FIG. 2 is a schematic diagram illustrating an example of synthetic pathway of a ligand conjugate (Compound 17) according to the present invention.

Using the linker compound 15 obtained in Example 1, a ligand conjugate having an oligosaccharide-derived structure represented by general formula (5) where n is 4, p$^1$ and p$^2$ are 1, m$^1$, m$^2$, m$^3$, and m$^4$ are 2, R' is hydrogen (H), and R is represented by general formula (12) was synthesized according to the following procedure. FIG. 2 illustrates a chemical reaction formula of the synthesis.

As shown in FIG. 2, reductive amination reaction was performed using the linker compound 15 obtained in Example 1, and the compound 16 (7 equivalents) which is a sugar molecule represented by general formula (12). With this, Compound 17 which is an example of the ligand conjugate of the present invention was obtained at a yield of 22%.

More specifically, the linker compound 15 (2.0 mg, 1.67 μmol) and Compound 16 (10 mg, 11.7 mmol) were dissolved in a mixture solvent of 100 ml of water, 400 ml of dimethylacetamide, and 10 ml of acetic acid. The resulting mixture was heated in a sealed tube for 25 hours at 37° C. in a shade to obtain a reaction solution. NaBH$_3$CN (3.51 mg, 50.2 mmol) was dissolved in 15 ml of acetic acid, mixed with the reaction solution, heated for 6 days at 37° C., concentrated under reduced pressure, and purified by using Sephadex G-50 (1.6 cm Φ×80 cm, a solution including 0.3M of NaCl mixed in PBS). A target fraction obtained by the purification was concentrated under reduced pressure to obtain a residue. The residue was desalinated by using Sephadex G-25 (1.6 cm Φ×40 cm, water). A target fraction obtained by the desalination was concentrated under reduced pressure, dissolved in water, and freeze-dried to obtain a white powder serving as Compound 17 (1.7 mg, yield of 22%).

$^1$H-NMR (400 MHz, D$_2$O) measurement was conducted on Compound 17 so obtained according to a method described in Example 1 to find that δ7.65-7.58 (8H, m, aromatic), 6.78-6.67 (8H, m, aromatic), 5.37 (4H, bs, H-1''), 5.13 (4H, bs, J=2.5 Hz), 4.52 (4H, bs, H-5'), 4.29 (10H, m, H-6a'', H-3', CONC$\underline{H}_2$CO), 4.19 (10H, m, H-6b'', H-2', CONC$\underline{H}_2$CO), 4.05 (3H, m, H-4'), 3.99-3.92 (14H, m, H-2, H-6a, H-5'', OC$\underline{H}_2$CON), 3.87 (8H, m, H-5, NCH$_2$C$\underline{H}_2$NH), 3.83 (8H, m, H-3, NCH$_2$C$\underline{H}_2$NH), 3.77-3.70 (8H, m, H-4, NCH$_2$C$\underline{H}_2$NH), 3.71 (4H, t, J=9.9 Hz, H-3''), 3.64-3.50 (25H, m, H-6b, NC$\underline{H}_2$CH$_2$NH, OC$\underline{H}_2$C$\underline{H}_2$O, CONHC$\underline{H}_2$, CONHCH$_2$C$\underline{H}_2$, SSC$\underline{H}$), 3.54 (3H, s, OC$\underline{H}_3$), 3.45-3.19 (14H, m, H-1a, H-1b, NC$\underline{H}_2$CH$_2$NH, C$\underline{H}_2$SS), 3.34 (4H, t, J=9.6 Hz, H-4''), 3.24 (4H, dd, J=3.4, 10.5 Hz, H-2''), 2.35-2.28 (1H, m, C$\underline{H}_2$CH$_2$SS), 2.27 (2H, bt, CH$_2$C$\underline{H}_2$CONHCH$_2$), 1.89-1.84 (1H, m, C$\underline{H}_2$CH$_2$SS), 1.56-1.46 (2H, m, C$\underline{H}_2$CH$_2$CONH), 1.35-1.14 (2H, m, C$\underline{H}_2$CH$_2$(CH$_2$)$_2$CONH). An ESI-MS (negative) measurement was conducted on Compound 17 to find that the m/z was 1449.93 [(M−10Na+7H)$^{3-}$]. This could examine a structure of Compound 17. It is to be noted that a molecular mass of the Compound 17 is C$_{134}$H$_{196}$N$_{16}$Na$_{16}$O$_{108}$S$_{14}$:4572.48.

The Compound 17 is a ligand conjugate having an oligosaccharide-derived structure represented by general formula (5) where n is 4, p$^1$ and p$^2$ are 1, m$^1$, m$^2$, m$^3$, and m$^4$ are 2, R' is hydrogen (H), and R is represented by general formula (6-3).

Example 3

Verification of Interaction Between a Sugar Chain Serving as Ligand and a Protein In the present Example, using a ligand conjugate obtained in Example 2 and having an oligosaccharide-derived structure represented by general formula (5) where n is 4, $p^1$ and $p^2$ are 1, $m^1$, $m^2$, $m^3$, and $m^4$ are 2, R' is hydrogen (H), and R is represented by general formula (6-3) (This ligand conjugate is hereinafter referred to as "Tetra-GlcNS6S-IdoA2S-Glc"), an intermolecular interaction between Tetra-GlcNS6S-IdoA2S-Glc and a protein was verified.

In the present Example, for the purpose of comparison, similar experiments were conducted on another two ligand conjugates that the inventors of the present application found before, and comparative study on their interactions was conducted. One of the two ligand conjugates, more specifically, is the ligand conjugate described in Patent document 1 and represented by general formula (13). Hereinafter, this ligand conjugate is referred to as "Mono-GlcNS6S-IdoA2S-Glc".

Example 3-1

Confirmation of Specific Interaction

First of all, in Example 3-1, an inhibition experiment was conducted to confirm a specific interaction between (i) a chip including a disaccharide unit (GlcNS6S-IdoA2S) represented by general formula (8) immobilized thereon and (ii) a heparin-binding protein. That is, in the presence of an inhibitor which inhibits a binding between the heparin-binding protein and the GlcNS6S-IdoA2S structure, whether a binding of the heparin-binding protein to the chip was inhibited was studied.

The present experiment used heparin (derived from small intestine of a pig, Mw=17600) serving as an inhibitor and bFGF serving as a heparin-binding protein. The bFGF, which is also termed as FGF-2, is known to facilitate wound healing by working on vascular endothelial cells and fibroblasts for its

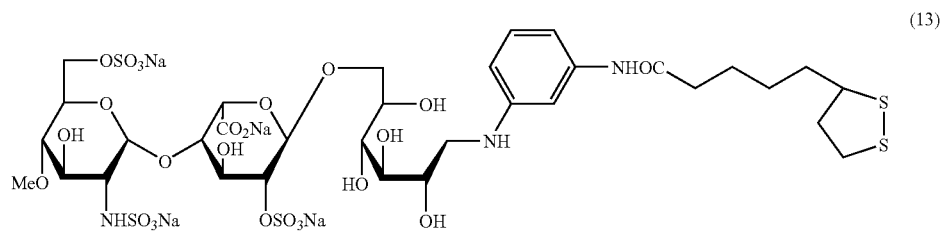

(13)

The other ligand conjugate is the ligand conjugate described in Japanese Unexamined Patent Publication No. 157108/2004 (Tokukai 2004-157108) and represented by general formula (14). Hereafter, this ligand conjugate is referred to as "Tri-GlcNS6S-IdoA2S-Glc". Note that Japanese Unexamined Patent Publication No. 157108/2004 was not open public at the point in time of a priority date of the present application.

vascularization and granulation promotion. In vivo, bFGF interacts with heparan sulfate which is a heparin-like substance on a cell surface, and expresses its biological activity. It has been reported that a minimum binding sequence required for bFGF binding is a sequence of fine sugar residues represented by general formula (15) given below (Reference: M. Maccarana, B. Casu & U. Lindahl, J. Biol. Chem. Vol. 268, p. 8857, in 1993).

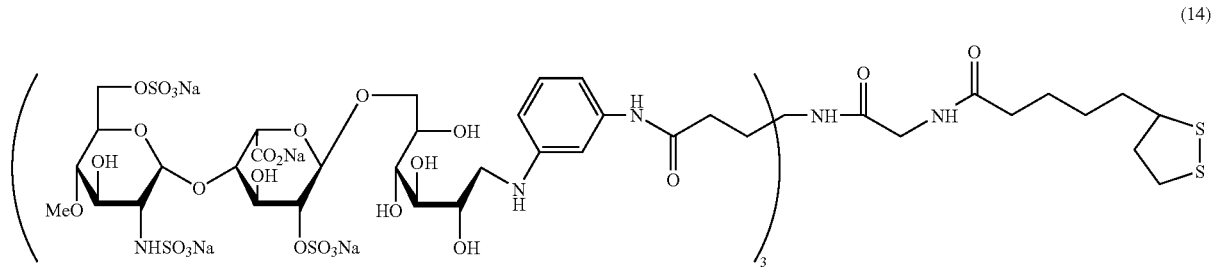

(14)

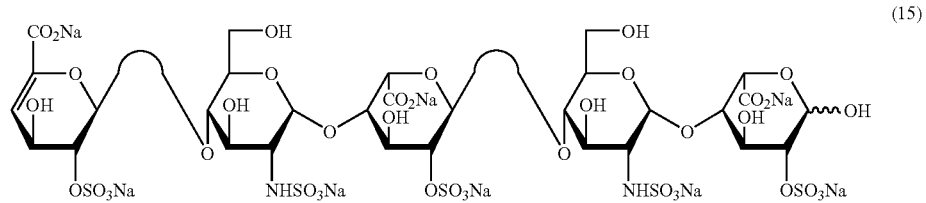

(15)

The above structure does not contain a structure having sulfation at 6 position of glucosamine residues. However, it has been confirmed that an indefinite number of sulfations at 6 of glucosamine residues are not necessary for association between the IdoA2S-GlcNS structure and bFGF in heparan sulfate, but are necessary for formation of active site. Therefore, bFGF was selected as a protein for observing an interaction with the GlcNS6S-IdoA2S structure.

Next, an experiment for inhibition of bFGF binding was conducted in the presence of haparin by using chips respectively including the foregoing Mono-GlcNS6S-IdoA2S-Glc, Tri-GlcNS6S-IdoA2S-Glc, and Tetra-GlcNS6S-IdoA2S-Glc immobilized thereon. That is, 200 nM of bFGF solution was mixed with each of heparins in different concentrations, i.e. concentrations of 3, 10, 100, 300, and 1000 nM, and mixture solutions were injected into chips.

Figure 3:
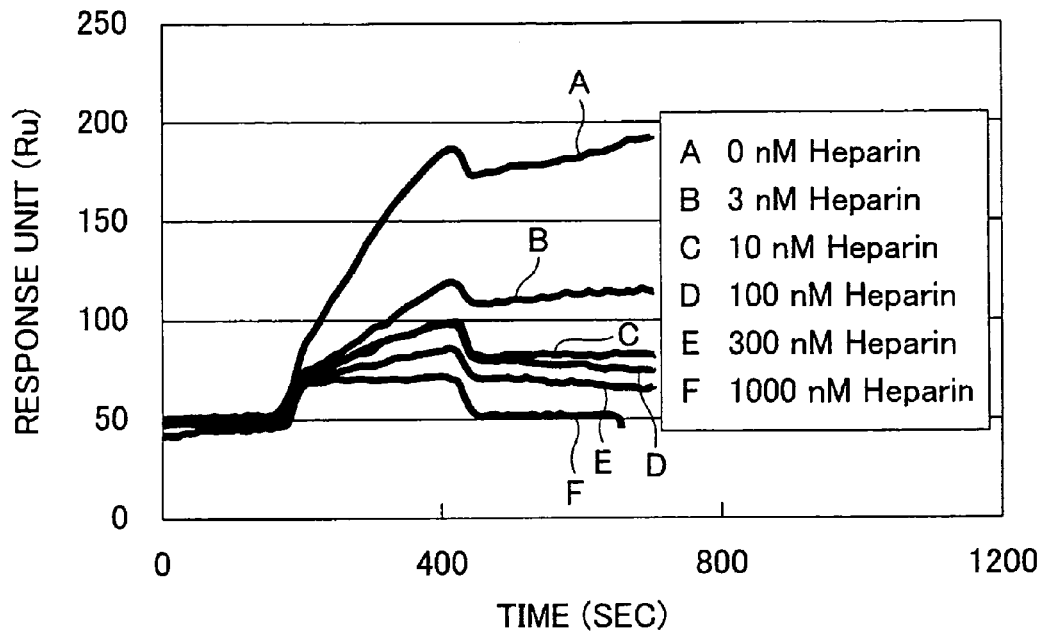
FIG. 3 is a graph showing binding behavior of bFGF to a chip including Mono-GlcNS6S-IdoA2S-Glc immobilized thereon in the presence of haparin.

FIG. 3 illustrates binding behaviors of bFGF to a chip including Mono-GlcNS6S-IdoA2S-Glc immobilized thereon. From FIG. 3, it was confirmed that bFGF binding to the chip including Mono-GlcNS6S-IdoA2S-Glc immobilized thereon decreases with dependence upon a concentration of heparin. That is, it was confirmed that bFGF binding to the chip including Mono-GlcNS6S-IdoA2S-Glc immobilized thereon was inhibited by heparin.

Figure 4:
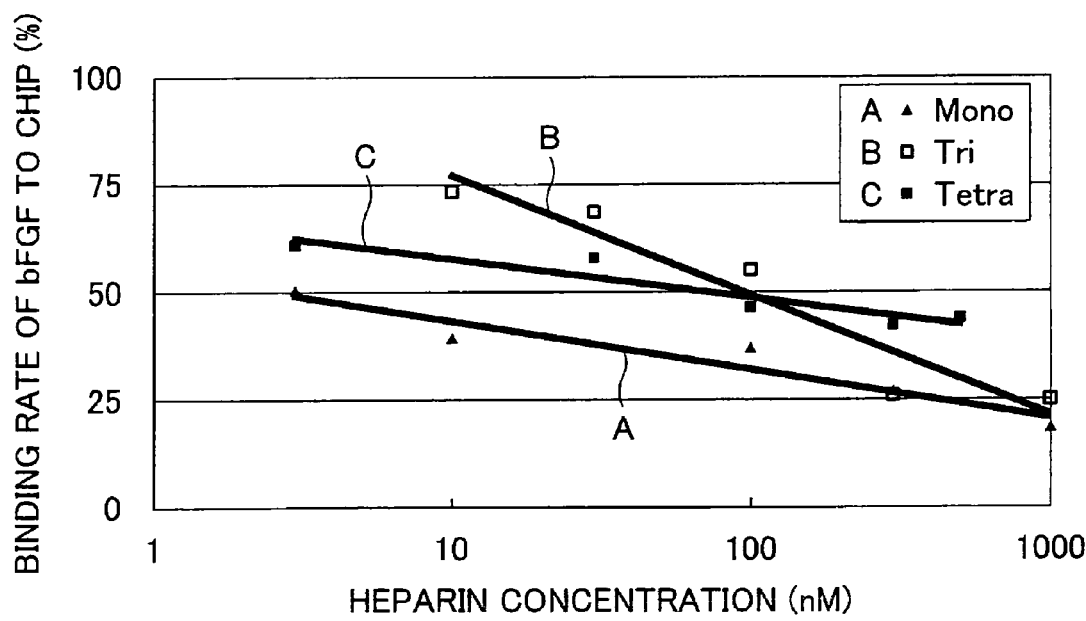
FIG. 4 is a graph showing rates of heparin inhibition of bFGF binding interactions to the chips respectively including Mono-GlcNS6S-IdoA2S-Glc, Tri-GlcNS6S-IdoA2S-Glc, and Tetra-GlcNS6S-IdoA2S-Glc immobilized thereon.

From sets of data on three types of chips obtained by the above experiment, inhibition rates of bFGF binding to the chips were calculated. The result of the calculation is shown in FIG. 4. It is to be noted that the inhibition rate is a percentage of a maximum angle change amount in the presence of haparin in a different concentration to a maximum angle change amount in the absence of heparin.

In a graph illustrated in FIG. 4, a point having 50% of inhibition rate of bFGF binding to the chip was defined as $IC_{50}$. As a result, the chip including Mono-GlcNS6S-IdoA2S-Glc immobilized thereon had $IC_{50}$=2.5 nM, the chip including Tri-GlcNS6S-IdoA2S-Glc immobilized thereon had $IC_{50}$=94 nM, and the chip including Tetra-GlcNS6S-IdoA2S-Glc immobilized thereon had $IC_{50}$=71 nM. This confirmed that the chip including Mono-GlcNS6S-IdoA2S-Glc immobilized thereon was one order lower in $IC_{50}$ value than the other two chips and was strongly influenced by inhibition effect of heparin. From the fact that all inhibition rates obtained by using the above chips changed with dependence upon a concentration of haparin, we can come to a conclusion that these chips specifically recognize bFGF which is a heparin-binding protein.

Example 3-2

Study on Relative Density of Sugar Chain on Chip Surface

Figure 5:
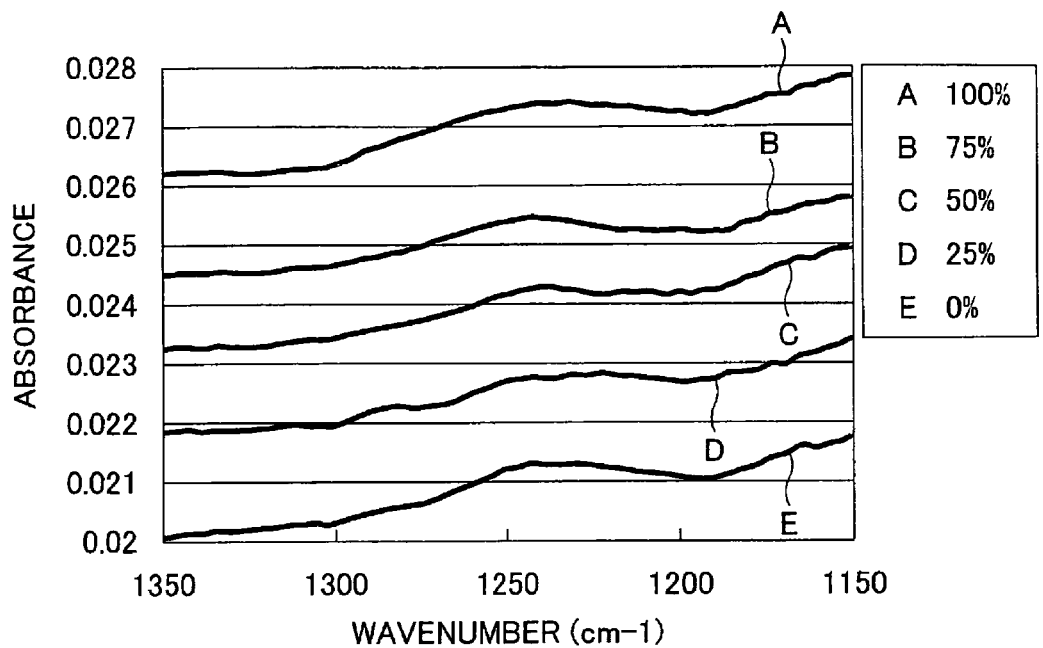
FIG. 5(*a*) is a graph showing total reflection infrared absorption spectra of Tri-GlcNS6S-IdoA2S-Glc at different mixture proportions in a solution.
Figure 5:
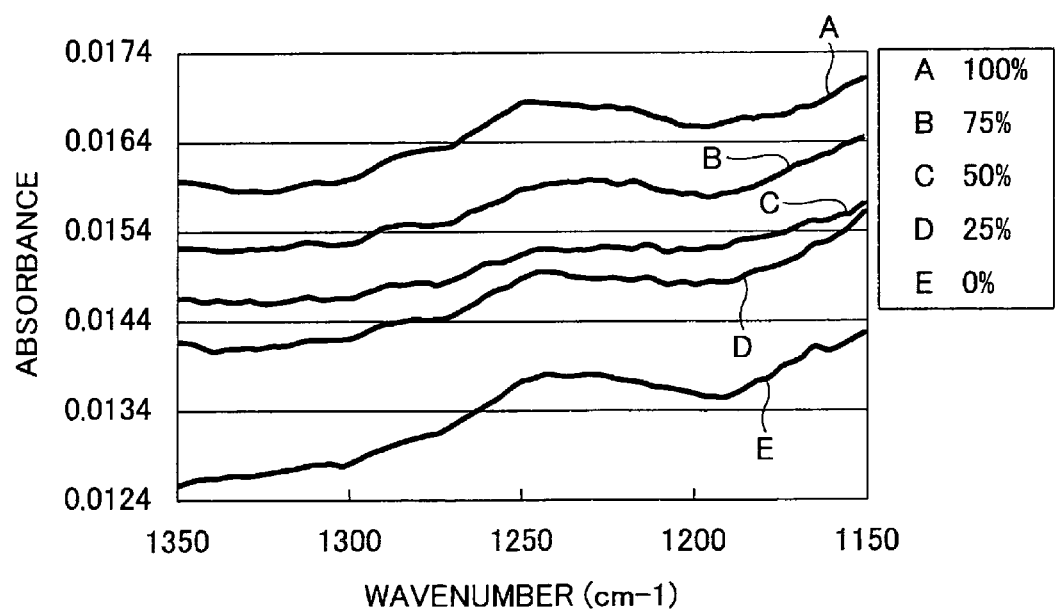

First of all, Tri-GlcNS6S-IdoA2S-Glc or Tetra-GlcNS6S-IdoA2S-Glc and a linker compound including bound molecules having no sugar chains (non-sugar chain-linker binding compound, hereinafter referred to as Mono-Glc) were mixed into a solution to immobilize them onto the chip. Then, change in density of a sulfated disaccharide, which is a ligand on the chip according to a percentage of mixture (percentage of incorporation) of Tri-GlcNS6S-IdoA2S-Glc or Tetra-GlcNS6S-IdoA2S-Glc into the linker compound, was studied by using ATR-FT-IR method. Proportions of Tri-GlcNS6S-IdoA2S-Glc or Tetra-GlcNS6S-IdoA2S-Glc in a solution were as follows: 0.25%, 50%, 75%, and 100%. The result is shown in FIGS. 5($a$) and 5($b$). FIG. 5($a$) indicates total reflection spectra of Tri-GlcNS6S-IdoA2S-Glc obtained with changes in percentage of mixture of Tri-GlcNS6S-IdoA2S-Glc in a solution. FIG. 5($b$) indicates total reflection spectra of Tetra-GlcNS6S-IdoA2S-Glc obtained with changes in percentage of mixture of Tetra-GlcNS6S-IdoA2S-Glc in a solution.

Figure 6:
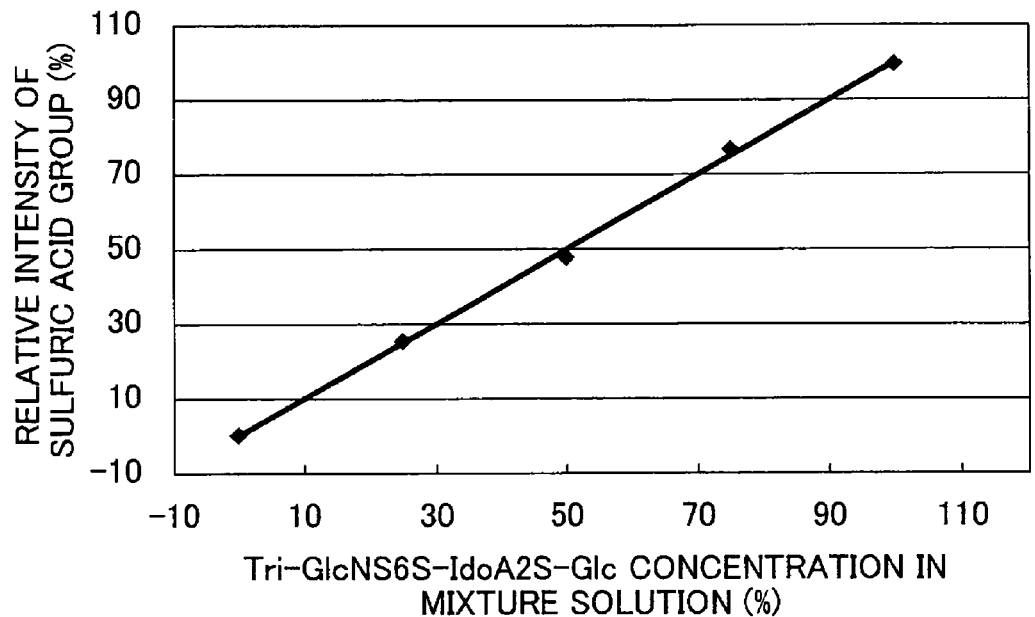
FIG. 6(*a*) is a graph showing a relative intensity of sulfuric acid group on a chip with respect to a mixture proportion of Tri-GlcNS6S-IdoA2S-Glc in a solution.
Figure 6:
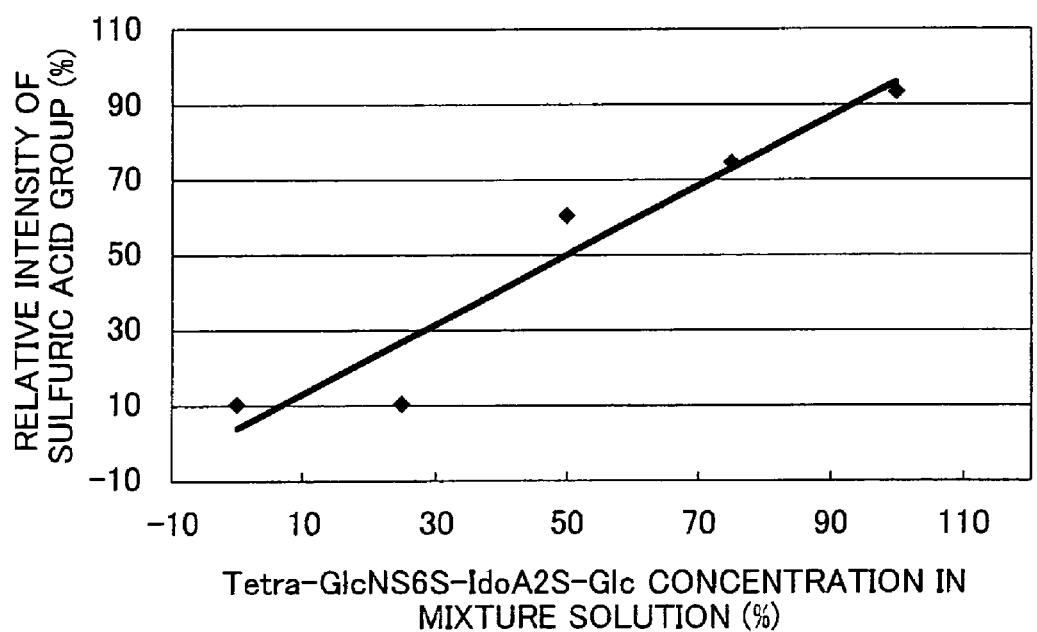

Since stretching vibration of S=O derived from sulfuric acid group was observed in a wavenumber domain from 1200 to 1303 $cm^{-1}$, sulfuric acid was quantified according to a multivariate analysis method by using an absorbance curve of this domain, and a relative intensity of sulfuric acid group on a chip with respect to a percentage of mixture of a ligand conjugate in a solution was plotted. A result of plotting is shown in FIGS. 6($a$) and 6($b$). FIG. 6($a$) is a graph illustrating a relative intensity of sulfuric acid group on a chip with respect to a percentage of mixture of Tri-GlcNS6S-IdoA2S-Glc in a solution. FIG. 6($b$) is a graph illustrating a relative intensity of sulfuric acid group on a chip with respect to a percentage of mixture of Tetra-GlcNS6S-IdoA2S-Glc in a solution. Since correlation coefficients of a first-order curve illustrated in FIGS. 6($a$) and 6($b$) are 0.9993 and 0.9610, respectively, percentages of immobilization of a sulfated disaccharide serving as a ligand (densities of sugar chains on a chip surface) are in proportion to abundance ratio of a ligand conjugate to a solution.

Example 3-3

Study on Influence of a Relative Density of Sugar Chains on Interaction with h-vWF Next, we have studied influence of a relative density of a sulfated disaccharide serving as a ligand on a chip surface on an interaction with a protein. In this study, interaction with human plasma-derived vWF (hereinafter referred to as h-vWF) was analyzed.

Six types of chips were prepared in such a manner that mixture ratios of the three types of ligand conjugates (Mono-GlcNS6S-IdoA2S-Glc, Tri-GlcNS6S-IdoA2S-Glc, and Tetra-GlcNS6S-IdoA2S-Glc) and Mono-Glc were 100:0 and 20:80. Using the chips, interaction with h-vWF was observed according to SPR method. Here, a procedure of measurement according to SPR method will be described.

For the measurement, SPR670 (Japan Laser Electronics Co., Ltd.) was used. A used sensor chip was a sensor chip (Japan Laser Electronics Co., Ltd.) prepared by depositing chromium of 2 nm thick as a contact layer on a glass substrate of 13 mm×20 mm×0.7 mm and further depositing a gold thin film of 50 nm thick on the contact layer. The sensor chip was placed in a UV ozone cleaner (product name: NL-UV253, Japan Laser Electronics Co., Ltd.) and was exposed to ultraviolet rays for 30 minutes so as to wash the surface of the sensor chip with ozone.

Next, after the sensor chip was placed in a dedicated PTFE cell (Japan Laser Electronics Co., Ltd.), the six types of chips were dissolved in a mixture solution (0.1 mM) with a mixture of methanol and water in a 1:1 ratio (methanol solution for a mixture of Mono-GlcNS6S-IdoA2S-Glc and Mono-Glc). 50 µl of the solution was taken into the PTFE cell, and sealed with a Parafilm. The PTFE cell having the chip therein was gently shaken overnight at room temperature on a Bio Dancer (New Brunswick Scientific Co., Ltd.).

The chip was washed with methanol six times, washed with water once. Subsequently, the chip was washed with methanol once and washed with water. The chip was air-dried and then mounted on a sensor chip cartridge of SPR670. The chip surface was fully come to equilibrium by a running buffer. Thereafter, a laser beam was irradiated onto the gold film. A surface plasmon resonant angle change then observed was monitored. A phosphate buffer solution (PBS) at pH 7.4 was used as the running buffer. Also, all SPR measurements were conducted at a constant temperature of 25° C. In the measurements, a used bFGF was bFGF made from STRATHMANN BIOTEC AG (Recombiant Human FGF-basic, MW; 17000, Lot No.; 471120), and a used h-vWF was h-vWF made from CALBIOCHEM (von Willebrand Factor, Human Plasma, MW; 270000 (on a Monomer Unit basis), Lot No.; B41632).

In the SPR measurements, when h-vWF was injected on the chips with different concentrations of 10 nM, 20 nM, 40 nM, 80 nM, and 160 nM, binding interaction was observed, and a state of h-vWF immobilized onto the chip was monitored. In this case, a dissociation agent for completely dissociating h-vWF from the chip without denaturation of sulfated disaccharide serving as a ligand was not found. Therefore, a dissociation constant ($K_D$) was calculated from the amount of h-vWF binding on the chip. As the amount of h-vWF binding used was a difference in amount of h-vWF binding between a state where the ligand conjugate was immobilized as a base and a state where a curve of a sensor gram of h-vWF injected with each different concentration became substantially level.

Figure 7:
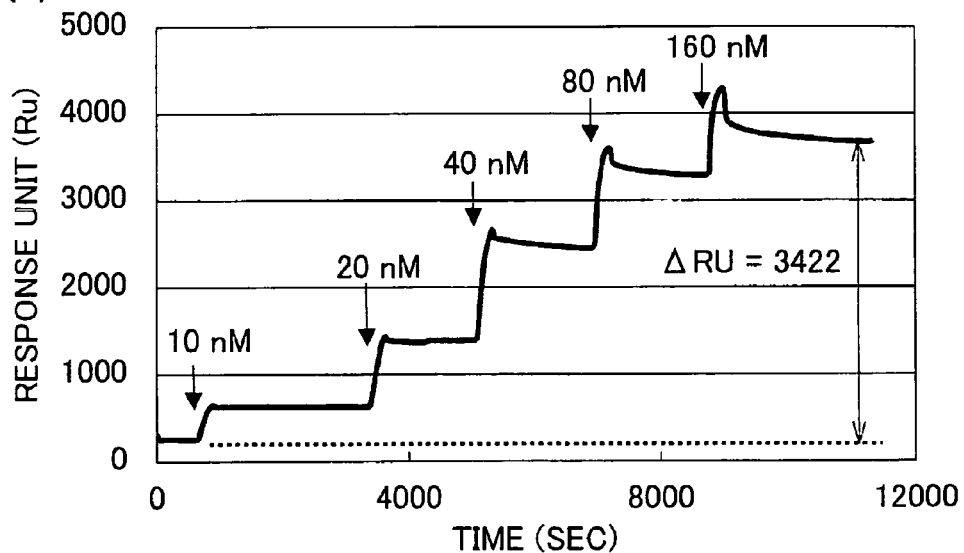
FIG. 7(*a*) is a graph showing a result of observing h-vWF binding interaction by the SPR method when a mixture ratio of Mono-GlcNS6S-IdoA2S-Glc and Mono-Glc was 100:0.
Figure 7:
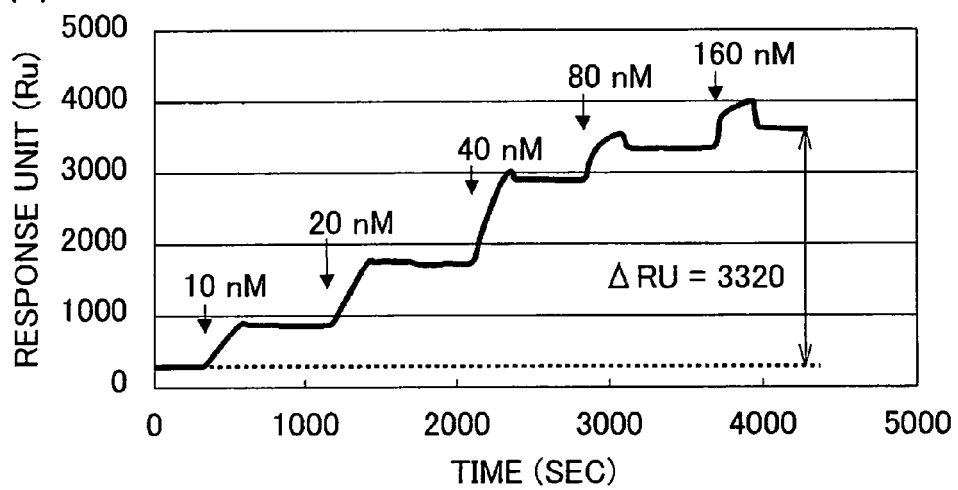
Figure 7:
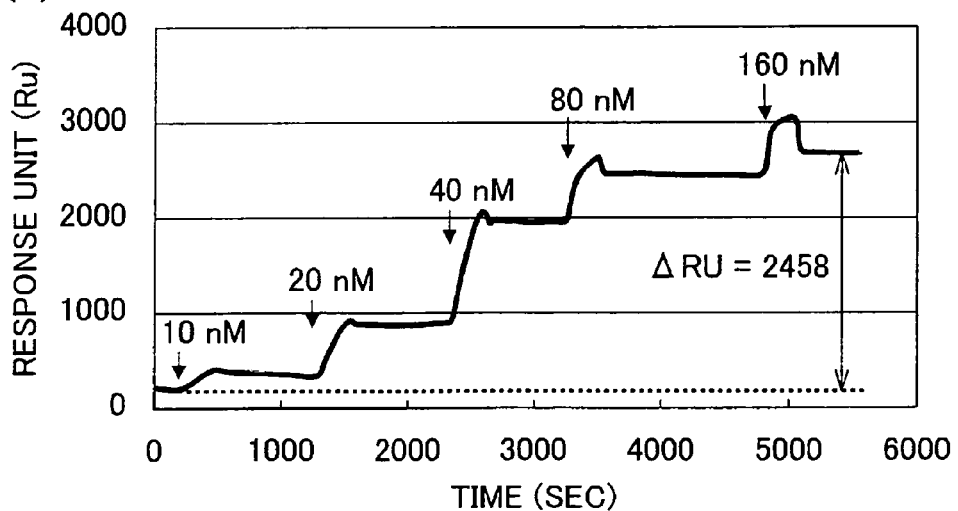
Figure 8:
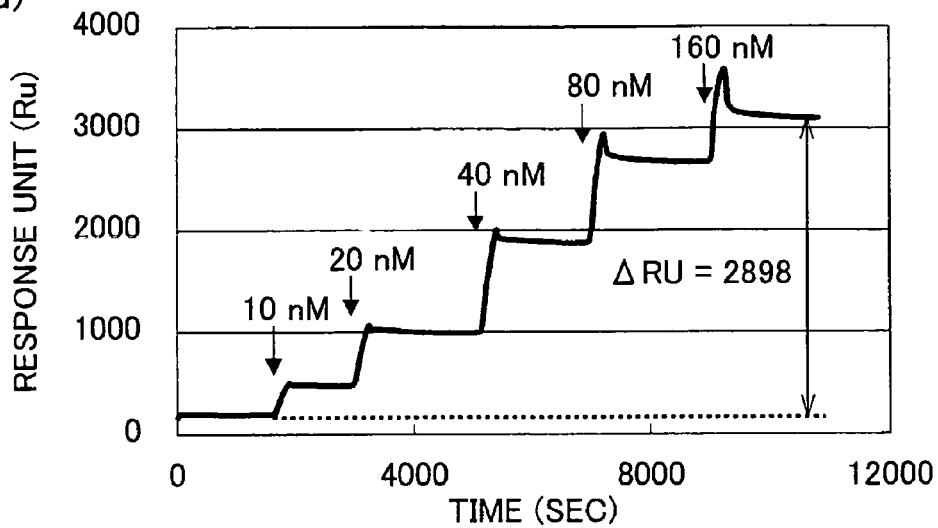
FIG. 8(a) is a graph showing a result of observing h-vWF binding interaction by the SPR method when a mixture ratio of Mono-GlcNS6S-IdoA2S-Glc and Mono-Glc was 20:80.
FIG. 8(b) is a graph showing a result of observing h-vWF binding interaction by the SPR method when a mixture ratio of Tri-GlcNS6S-IdoA2S-Glc and Mono-Glc was 20:80.
FIG. 8(c) is a graph showing a result of observing h-vWF binding interaction by the SPR method when a mixture ratio of Tetra-GlcNS6S-IdoA2S-Glc and Mono-Glc was 20:80.
Figure 8:
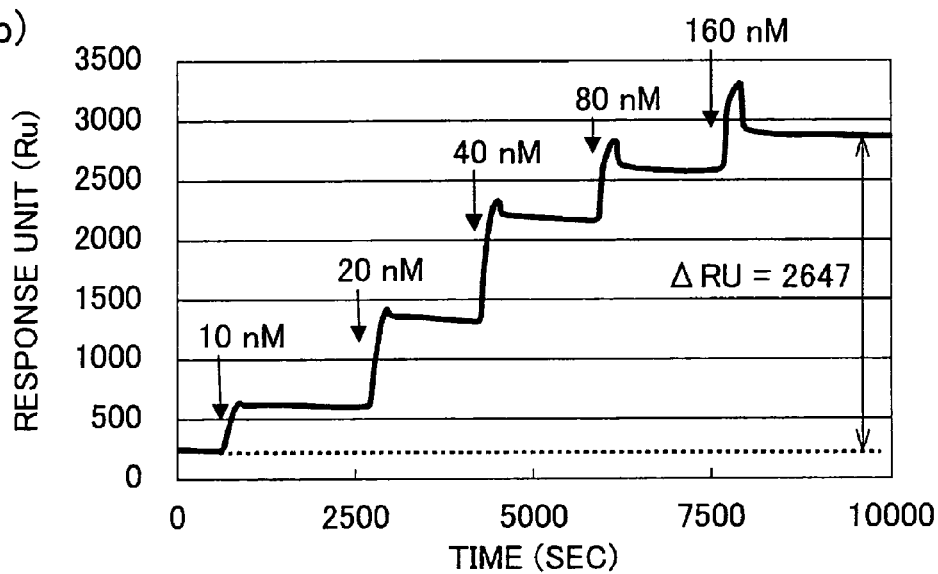
Figure 8:
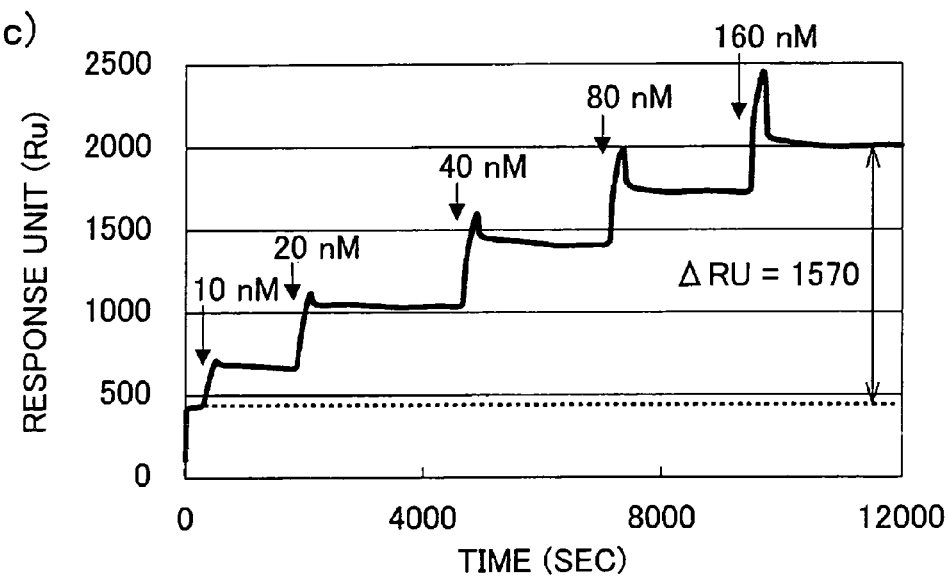

FIGS. 7(a) through 7(c) illustrate measurements of binding interactions obtained with mixture of any of the three types of ligand conjugates (Mono-GlcNS6S-IdoA2S-Glc, Tri-GlcNS6S-IdoA2S-Glc, and Tetra-GlcNS6S-IdoA2S-Glc) and Mono-Glc in a 100:0 ratio. FIG. 7(a) illustrates measurement of binding interaction obtained with Mono-GlcNS6S-IdoA2S-Glc, FIG. 7(b) illustrates measurement of binding interaction obtained with Tri-GlcNS6S-IdoA2S-Glc, and FIG. 7(c) illustrates measurement of binding interaction obtained with Tetra-GlcNS6S-IdoA2S-Glc. FIGS. 8(a) through 8(c) illustrate measurements of binding interactions obtained with mixture of any of the three types of ligand conjugates (Mono-GlcNS6S-IdoA2S-Glc, Tri-GlcNS6S-IdoA2S-Glc, and Tetra-GlcNS6S-IdoA2S-Glc) and Mono-Glc in a 20:80 ratio. FIG. 8(a) illustrates measurement of binding interaction obtained with Mono-GlcNS6S-IdoA2S-Glc, FIG. 8(b) illustrates measurement of binding interaction obtained with Tri-GlcNS6S-IdoA2S-Glc, and FIG. 8(c) illustrates measurement of binding interaction obtained with Tetra-GlcNS6S-IdoA2S-Glc.

FIGS. 9(a) through 9(c) are plots of binding amounts obtained by the above result for different h-vWF concentrations. FIG. 9(a) is a plot of binding amounts obtained with Mono-GlcNS6S-IdoA2S-Glc, FIG. 9(b) is a plot of binding amounts obtained with Tri-GlcNS6S-IdoA2S-Glc, and FIG. 9(c) is a plot of binding amounts obtained with Tetra-GlcNS6S-IdoA2S-Glc. Also, FIGS. 9(a) through 9(c) indicate calculation results of dissociation constants ($K_D$) from curves of the plots.

As illustrated in FIG. 9(a), for the chips including a sulfated disaccharide serving as a ligand immobilized with Mono-GlcNS6S-IdoA2S-Glc and Mono-Glc in a 100:0 ratio and the chips including a sulfated disaccharide serving as a ligand immobilized with Mono-GlcNS6S-IdoA2S-Glc and Mono-Glc in a 20:80 ratio, dissociation constants were $K_D$=35 nM and 41 nM, respectively. As illustrated in FIG. 9(b), for the chips including a sulfated disaccharide serving as a ligand immobilized with Tri-GlcNS6S-IdoA2S-Glc and Mono-Glc in a 100:0 ratio and the chips including a sulfated disaccharide serving as a ligand immobilized with Tri-GlcNS6S-IdoA2S-Glc and Mono-Glc in a 20:80 ratio, dissociation constants were $K_D$=27 nM and 24 nM, respectively. Further, for the chips including a sulfated disaccharide serving as a ligand immobilized with Tetra-GlcNS6S-IdoA2S-Glcto and Mono-Glc in a 100:0 ratio and the chips including a sulfated disaccharide serving as a ligand immobilized with Tetra-GlcNS6S-IdoA2S-Glcto and Mono-Glc in a 20:80 ratio, dissociation constants were $K_D$=32 nM and 35 nM, respectively.

From these results, it was found that in a case where h-vWF was used as analight, changes in abundance of sugar chains serving as a ligand on a chip had almost no influence on affinity. Further, even with the use of a chip including a ligand conjugate having a different interval between sugar chains immobilized thereon, difference in interval between sugar chains had no influence on a value of dissociation constant in the interaction with h-vWF. It was considered that this is because existence of a plurality of haparin binding domains caused due to a multimer structure of h-vWF significantly decreased a dissociation velocity, and thus difference in interval between sugar chains did not reflect a dissociation constant.

Example 3-4

Study on Influence of a Relative Density of Sugar Chains on Interaction with Protein The following experiment was conducted, considering that using an *Escherichia-coli*-derived recombinant human vWF partial protein having only A1 loop having one heparin binding domain (hereinafter referred to as rhvWF-A1), makes it possible to study on influence of difference in interval between sugar chains upon interaction between a sugar chain and sugar chain binding protein in interaction between a sugar chain clustered on the chip and a protein in interaction between sugar chains clustered on a chip and a protein. rhvWF-A1 was prepared according to the document (A. Cruz, R. I. Handin & R. J. Wise, J. Biol. Chem. Vol. 264, p. 21238, in 1933).

Figure 10:
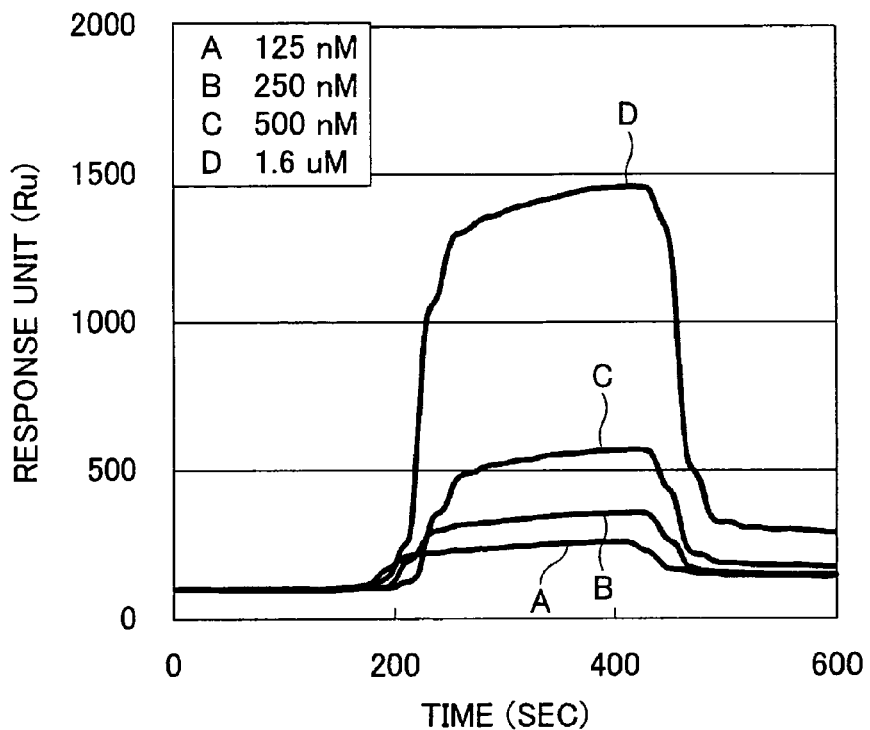
FIG. 10(a) is a graph showing results of measurements of interactions between a chip including Mono-GlcNS6S-IdoA2S-Glc immobilized thereon and rhvWF-A1 when a ratio of Mono-GlcNS6S-IdoA2S-Glc and Mono-Glc is 100:0.
FIG. 10(b) is a graph showing results of measurements of interactions between a chip including Mono-GlcNS6S-IdoA2S-Glc immobilized thereon and rhvWF-A1 when a ratio of Mono-GlcNS6S-IdoA2S-Glc and Mono-Glc is 50:50.
Figure 10:
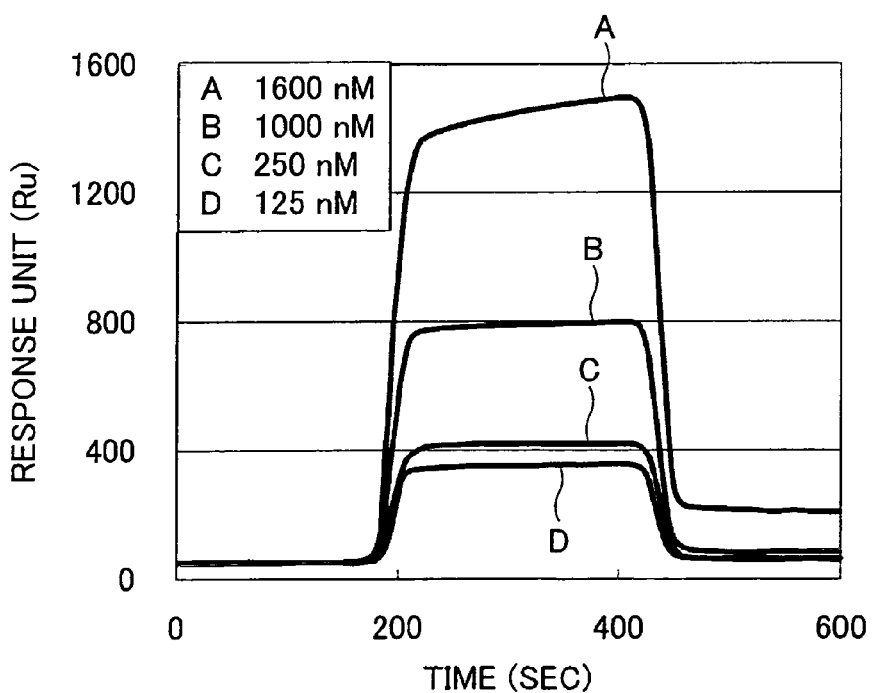
Figure 11:
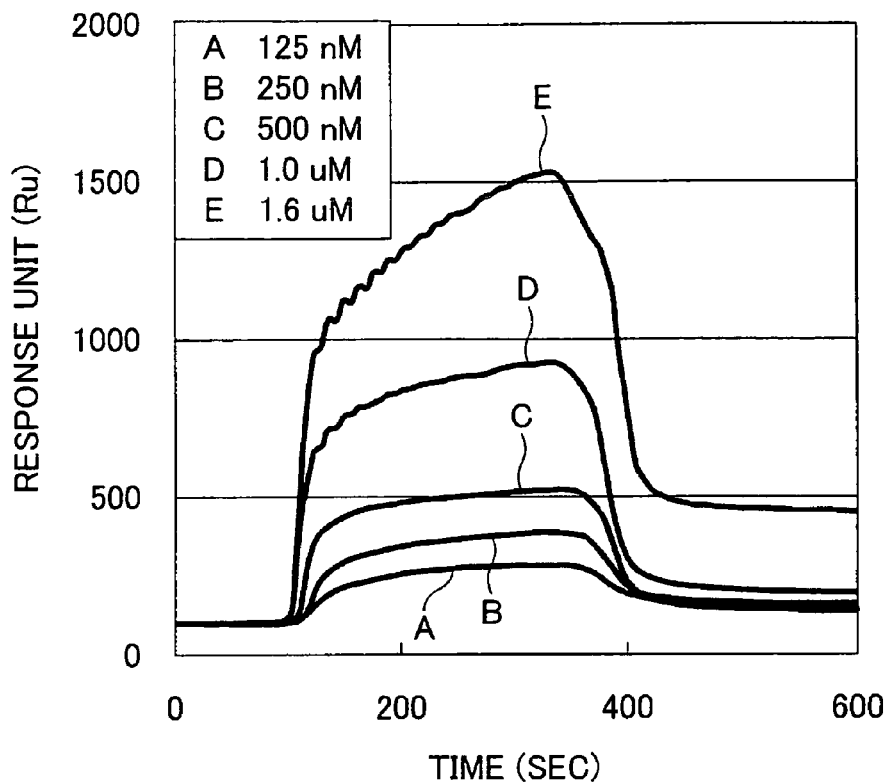
FIG. 11(a) is a graph showing results of measurements of interactions between a chip including Tri-GlcNS6S-IdoA2S-Glc immobilized thereon and rhvWF-A1 when a ratio of Tri-GlcNS6S-IdoA2S-Glc and Mono-Glc is 100:0.
FIG. 11(b) is a graph showing results of measurements of interactions between a chip including Tri-GlcNS6S-IdoA2S-Glc immobilized thereon and rhvWF-A1 when a ratio of Tri-GlcNS6S-IdoA2S-Glc and Mono-Glc is 50:50.
Figure 11:
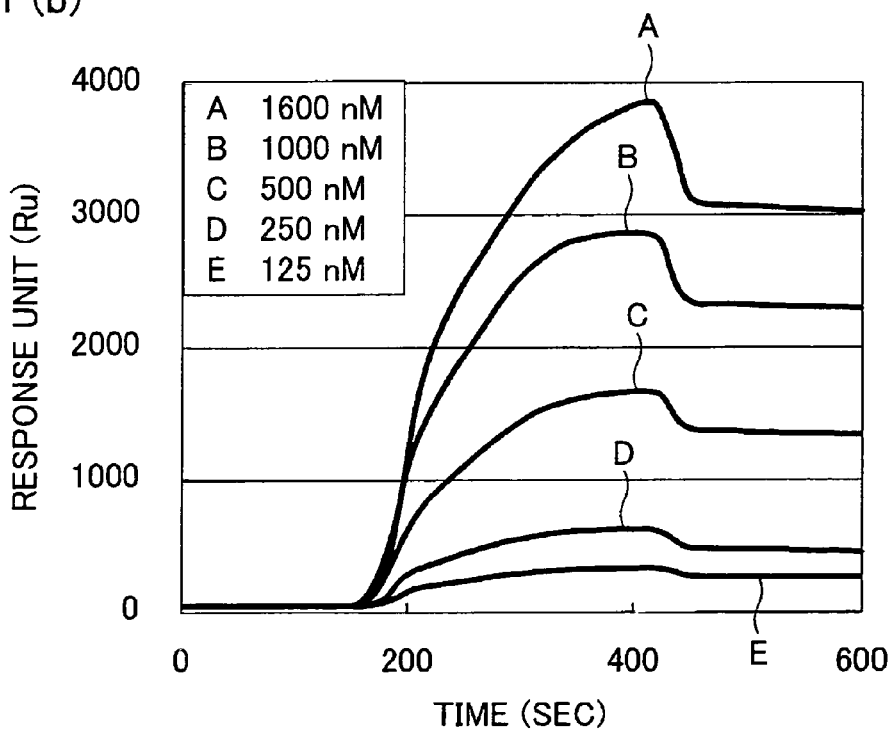
Figure 12:
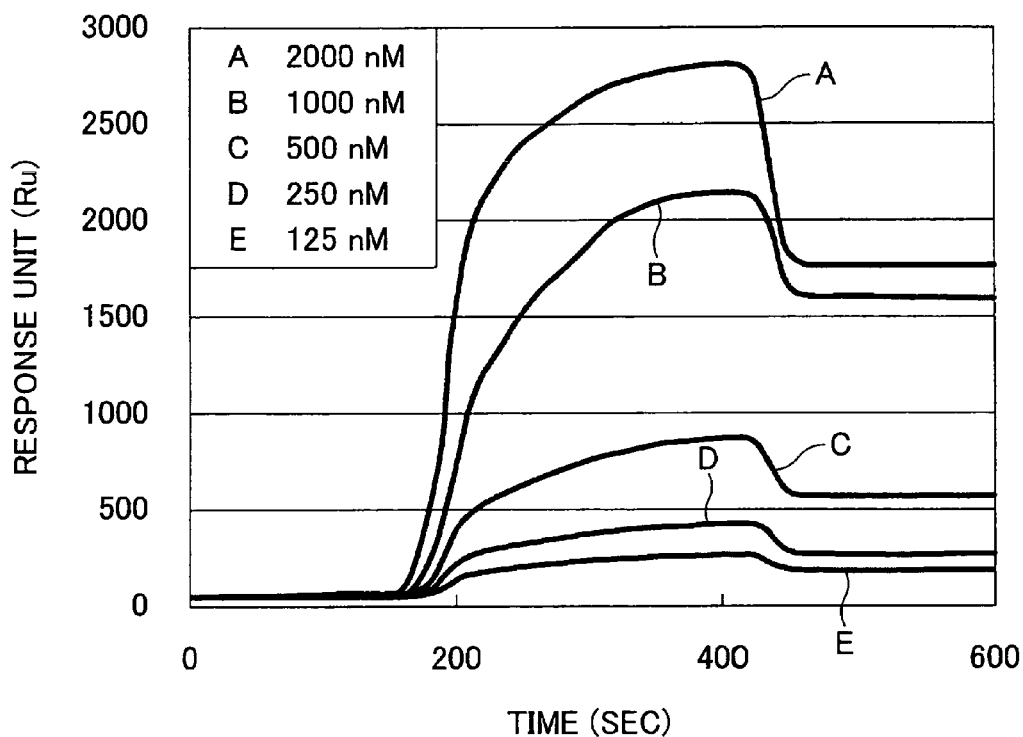
FIG. 12(a) is a graph showing results of measurements of interactions between a chip including Tetra-GlcNS6S-IdoA2S-Glc immobilized thereon and rhvWF-A1 when a ratio of Tetra-GlcNS6S-IdoA2S-Glc and Mono-Glc is 100:0.
FIG. 12(b) is a graph showing results of measurements of interactions between a chip including Tetra-GlcNS6S-IdoA2S-Glc immobilized thereon and rhvWF-A1 when a ratio of Tetra-GlcNS6S-IdoA2S-Glc and Mono-Glc is 50:50.
Figure 12:
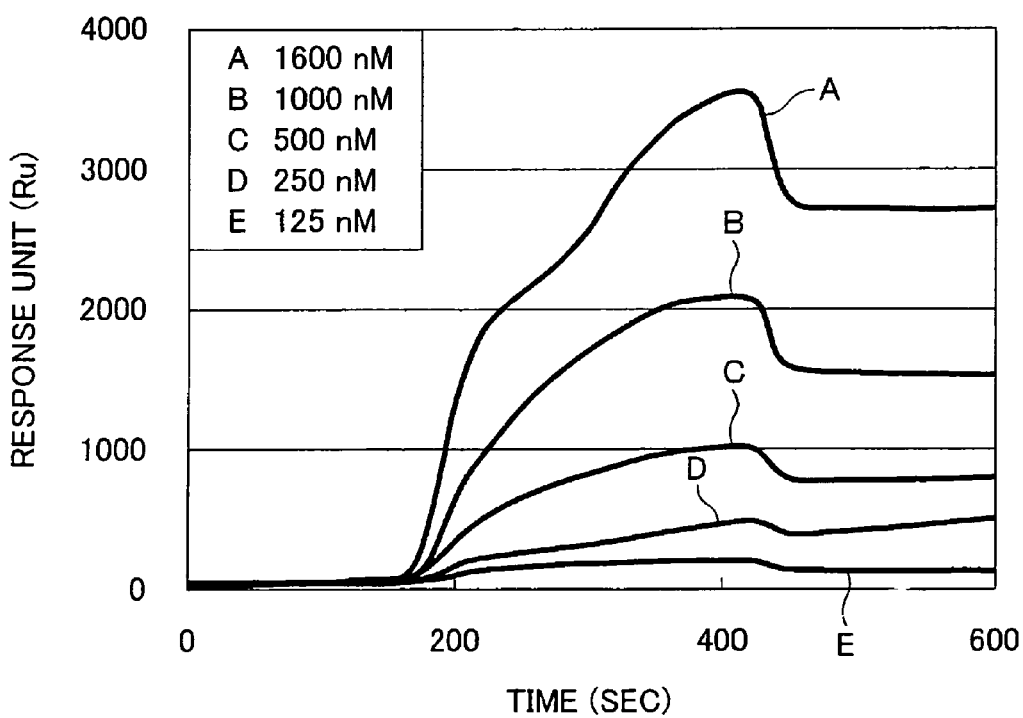

Chips used in the experiment were (i) chips respectively including combinations of any of the three ligand conjugates (Mono-GlcNS6S-IdoA2S-Glc, Tri-GlcNS6S-IdoA2S-Glc, Tetra-GlcNS6S-IdoA2S-Glc) as ligand conjugates and Mono-Glc in a 100:0 ratio and (ii) chips respectively including combinations of any of the three ligand conjugates (Mono-GlcNS6S-IdoA2S-Glc, Tri-GlcNS6S-IdoA2S-Glc, Tetra-GlcNS6S-IdoA2S-Glc) as ligand conjugates and Mono-Glc in a 50:50 ratio. FIGS. 10 through 12 show measurement results of binding interaction between rhvWF-A1 and the chips with different concentrations of rhvWF-A1. FIG. 10(a) illustrates measurement of binding interaction obtained for the chip with Mono-GlcNS6S-IdoA2S-Glc and Mono-Glc in a 100:0 ratio. FIG. 10(b) illustrates measurement of binding interaction obtained for the chip with Mono-GlcNS6S-IdoA2S-Glc and Mono-Glc in a 50:50 ratio. FIG. 11(a) illustrates measurement of binding interaction obtained for the chip with Tri-GlcNS6S-IdoA2S-Glc and Mono-Glc in a 100:0 ratio. FIG. 11(b) illustrates measurement of binding interaction obtained for the chip with Tri-GlcNS6S-IdoA2S-Glc and Mono-Glc in a 50:50 ratio. FIG. 12(a) illustrates measurement of binding interaction obtained for the chip with Tetra-GlcNS6S-IdoA2S-Glc and Mono-Glc in a 100:0 ratio. FIG. 12(b) illustrates measurement of binding interaction obtained for the chip with Tetra-GlcNS6S-IdoA2S-Glc and Mono-Glc in a 50:50 ratio.

Table 1 shows dissociation constants, binding constants, binding velocity constants, and dissociation velocity constants calculated from these results. In Table 1, dissociation constant is represented by $K_D$ ($k_d/k_a$), binding constant is represented by $K_A$ ($k_a/k_d$), binding velocity constant is represented by $k_a$, and dissociation velocity constant is represented by $k_d$.

TABLE 1

| No. | Types of Ligands | Composition ratio on chip | $K_D$ (μM) | $K_A$ ($M^{-1} \times 10^{-5}$) | $k_a$ ($M^{-1}s^{-1} \times 10^3$) | $k_d$ ($s^{-1} \times 10^{-3}$) |
|---|---|---|---|---|---|---|
| 1 | Mono-GlcNS6S-IdoA2A- | 100/0 | 2.60 | 3.85 | 8.38 | 21.9 |
| 2 | Glc/Mono-Glc | 50/50 | 3.79 | 2.64 | 14.6 | 55.2 |
| 3 | Tri-GlcNS6S-IdoA2A- | 100/0 | 1.20 | 8.33 | 6.60 | 8.05 |
| 4 | Glc/Mono-Glc | 50/50 | 1.50 | 6.65 | 4.52 | 6.83 |
| 5 | Tetra-GlcNS6S-IdoA2A- | 100/0 | 0.99 | 10.1 | 6.50 | 6.44 |
| 6 | Glc/Mono-Glc | 50/50 | 1.00 | 9.96 | 5.24 | 5.26 |

As shown in Table 1, the chip including Mono-GlcNS6S-IdoA2S-Glc immobilized had a larger dissociation constant ($K_D$=2.60 μM) than the chip including Tri-GlcNS6S-IdoA2S-Glc immobilized and the chip including Tetra-GlcNS6S-IdoA2S-Glc immobilized. A relative decrease in density of sugar chains immobilized on the chip further increased a value of the dissociation constant ($K_D$=3.79 μM). On the other hand, in case of the chip including Tri-GlcNS6S-IdoA2S-Glc immobilized, a relative decrease in density of sugar chains immobilized on the chip increased a value of the dissociation constant to some extent ($K_D$=1.20 μM→1.50 μM). In case of the chip including Tetra-GlcNS6S-IdoA2S-Glc immobilized, change in density of sugar chains immobilized on the chip brought about almost no change in value of the dissociation constant ($K_D$=0.99 μM→1.00 μM).

Further, as shown in Table 1, it was confirmed that the chip including Mono-GlcNS6S-IdoA2S-Glc immobilized had one order higher dissociation velocity constant ($k_d$) than the other two chips respectively including the other ligand conjugates. From this result, it can be considered that Tri-GlcNS6S-IdoA2S-Glc and Tetra-GlcNS6S-IdoA2S-Glc are not affected by a relative decrease in density of sugar chains immobilized on the chip because they have a sugar chain cluster structure which controls an interval between sugar chains of a sulfated oligosaccharide in a molecule.

That is, in terms of interaction with rhvWF-A1, it was confirmed that the chip including Mono-GlcNS6S-IdoA2S-Glc immobilized thereon decreases its binding force as a density of sugar chains immobilized on the chip is decreased. On the other hand, in case of the chip including Tri-GlcNS6S-IdoA2S-Glc immobilized thereon and the chip including Tetra-GlcNS6S-IdoA2S-Glc immobilized thereon, it was confirmed that their binding forces change little as a density of sugar chains immobilized on the chips is decreased.

From the above results, it was established that in order to increase binding forces in interaction between sugar chains of a sulfated oligosaccharide and a sugar-chain-binding protein, a structure in which sugar chains of a sulfated oligosaccharide having the same ligand conjugate structure are two-dimensionally clustered on a chip, as in the chip including Mono-GlcNS6S-IdoA2S-Glc immobilized thereon, is not enough, and a clustering structure in which an interval between sugar chains is controlled in molecular level, Tri-GlcNS6S-IdoA2S-Glc and Tetra-GlcNS6S-IdoA2S-Glc, is necessary.

Example 4

Synthesis of Linker Compound (Compound 26) and Ligand Conjugate (Compound 27)

Figure 13:
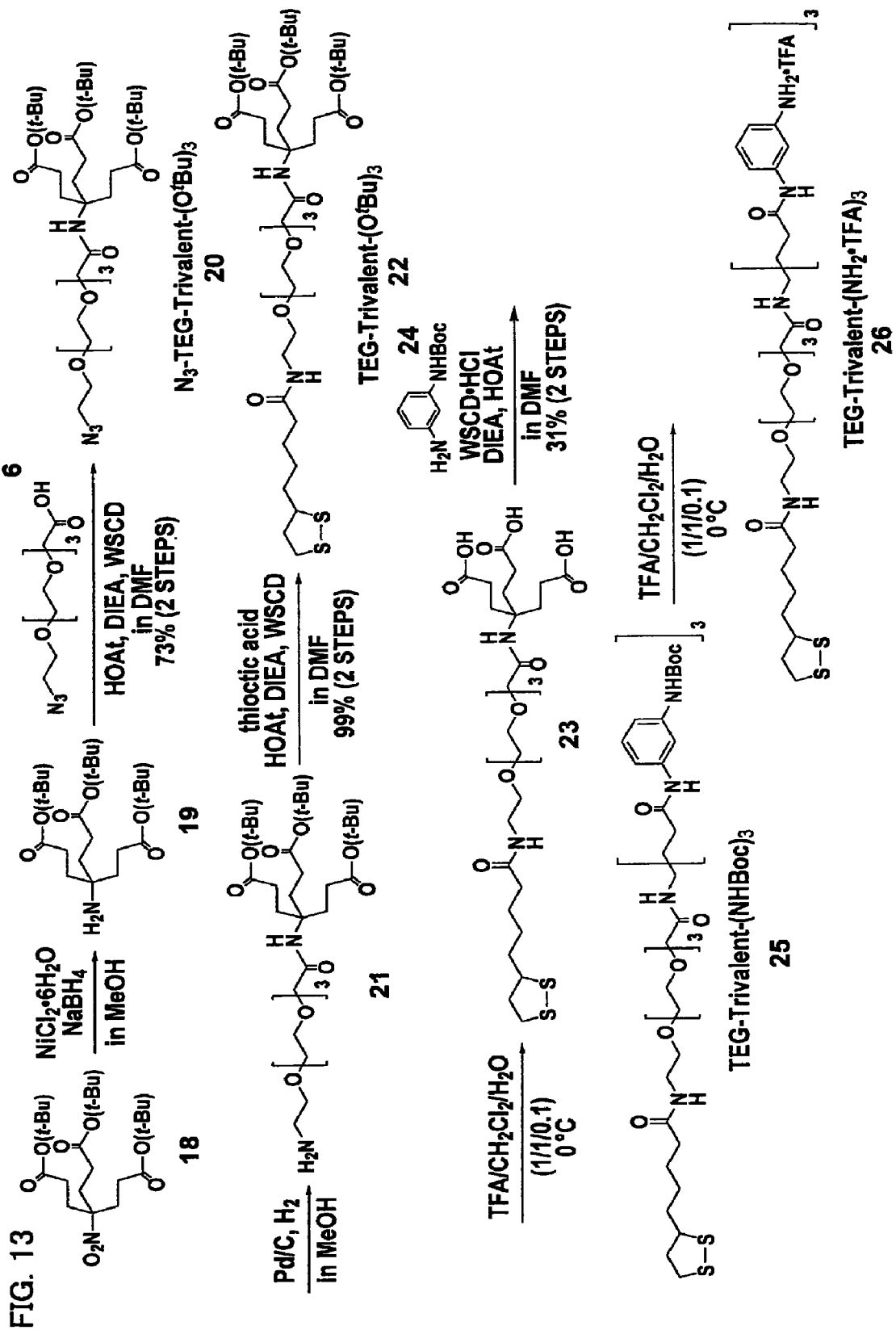
FIG. 13 is a schematic diagram illustrating an example of synthetic pathway of a linker compound (Compound 26) according to the present invention.
Figure 14:
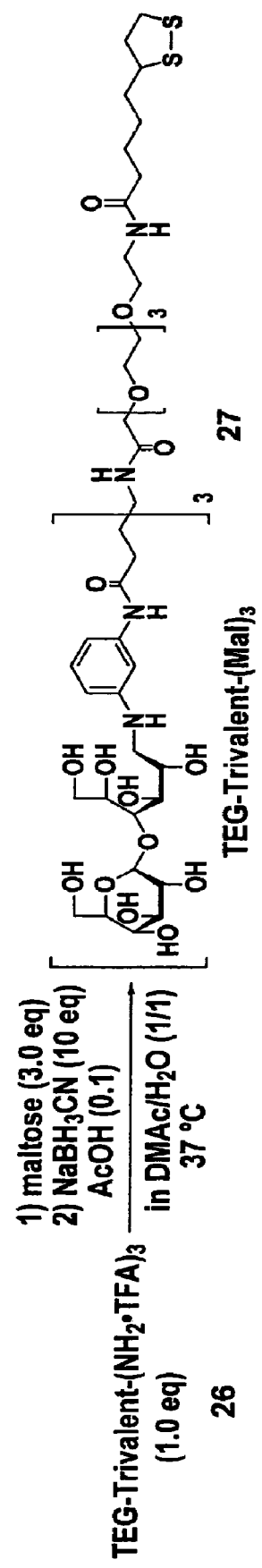
FIG. 14 is a schematic diagram illustrating an example of synthetic pathway of a ligand conjugate (Compound 27) according to the present invention.

One of the linker compounds according to the present invention, i.e. the linker compound (Compound 26) having a structure represented by general formula (1) where a is 1, b is 4, d is 1, e is 4 and X is represented by general formula (4) wherein $q^1$, $q^2$, $q^3$ are 2, and $r^1$, $r^2$, $r^3$, $t^1$, $t^2$, $t^3$, $u^1$, $u^2$, and $u^3$ are 0, and the ligand conjugate (Compound 27) having a structure represented by general formula (7) where a is 1, b is 4, d is 1, e is 4, $q^1$, $q^2$, $q^3$ are 2, and $r^1$, $r^2$, $r^3$, $t^1$, $t^2$, $t^3$, $u^1$, $u^2$, and $u^3$ are 0, R' is hydrogen (H), and R is represented by general formula (6-2) were synthesized by the following procedure. FIG. 13 illustrates a process of synthesizing the linker compound (Compound 26). FIG. 14 illustrates a process of synthesizing the ligand conjugate (Compound 27) from the linker compound (Compound 26). Reference numbers given to the compounds in the descriptions of Example 4 correspond to reference numbers described in FIGS. 13 and 14.

[Measurement Method, Reagent, and Others]

For $^1$H-NMR spectrum measurement, JOEL-Delta600 Spectrometer was used. Chemical shifts in $CDCl_3$ are expressed in δ-values in accordance with chemical shift of tetramethylsilane (0.00 ppm) as a reference substance. Chemical shifts in $D_2O$ are expressed in δ-values in accordance with chemical shift of DHO (4.65 ppm) as a reference substance. A mass spectrometry measurement was carried out by using PerSeptive Biosystem Mariner™ Biospectrometry Workstation. A medium-pressure silica gel chromatography was carried out by using Silicagel 60 (Merck, 0.040-0.063 mm). A thin-layer chromatography was carried out by using Precoated Silicagel 60 F254 (Merck, 0.5 mm). All reagents and dehydrated solvents were purchased from Kanto Chemical Co. Ltd.

(1) Synthesis of N₃-TEG-Trivalent-(O^tBU)₃ (Compound 20) (See FIG. 13)

O₂N-Trivalent-(O^tBu)₃ (Compound 18) (757 mg, 1.70 mmol) and nickel chloride hexahydrate (NiCl₂.6H₂O) (80.8 mg, 0.340 mmol) were dissolved in methanol (20 ml). To the solution, sodium borohydride (322 mg, 8.50 mmol) was added with five-equivalent portions, and the resulting mixture was stirred for 30 minutes at room temperature. After Methanol was removed by concentration, water and chloroform was added to the residue. After the residue was subjected to celite filtration, an organic phase was extracted from the filtrate with chloroform three times. After the organic phase was dried with anhydrous sodium sulfate, the drying agent was filtered out to obtain a filtrate. The filtrate was concentrated under reduced pressure to obtain a residue (Compound 19). The obtained residue and N₃-TEG-COOH (Compound 6) (441 mg, 1.70 mmol) were dissolved in anhydrous dimethylformamide (10 ml). To the mixture, DIEA (592 μl, 3.40 mmol), HOAt (463 mg, 3.40 mmol), and EDC.HCl (652 mg, 3.40 mmol) were added in this order under argon atmosphere at room temperature, and the resulting mixture was stirred for 16 hours. After the reaction solution was mixed with water, an organic phase was extracted with ethyl acetate three times from an aqueous phase. The organic phase washed with a saturated saline solution, and dried with an anhydrous magnesium sulfate. Then, the drying agent was filtered out from the dried residue to obtain a filtrate. The filtrate was concentrated under reduced pressure to obtain a residue. The residue was purified by silica gel column chromatography (50 g, chloroform:acetone=50:1) to obtain N₃-TEG-Trivalent-(O^tBu)₃ (Compound 20) as a colorless oily object. A yield thereof was 839 mg (73%).

¹H-NMR spectrum (600 MHz, CDCl₃) measurement was conducted on Compound 20 so obtained to find that δ3.90 (s, 2H, —OCH₂CONH—), 3.70-3.67 (m, 14H, —OCH₂CH₂O—×3, N₃CH₂CH₂O—), 3.39 (t, 2H, J=4.8 Hz, N₃CH₂CH₂O—), 2.21-2.18 (m, 6H, —CH₂CH₂CO—×3), 2.00-1.96 (m, 6H, —CH₂CH₂CO—×3), 1.43 (s, 27H, —CH₃×9). An ESI-MS (positive) measurement was conducted to find that the m/z was 697.45[(M+Na)⁺]. This could examine a structure of Compound 20. It is to be noted that a molecular mass of the Compound 20 is $C_{32}H_{58}N_4O_{11}$: 676.41.

(2) Synthesis of TEG-Trivalent-(O^tBUu)₃ (Compound 22) (See FIG. 13)

The Compound 20 (N₃-TEG-Trivalent-(O^tBU)₃)(837 mg, 1.24 mmol) was dissolved in methanol (10 ml), mixed with 10% Pd/C (200 mg), and stirred for 1.5 hours under hydrogen atmosphere at room temperature. Pd/C was filtered out to obtain a filtrate. The filtrate was concentrated under reduced pressure to obtain a residue (Compound 21). The residue and thioctic acid (385 mg, 1.87 mmol) were dissolved in anhydrous dimethylformamide (10 ml). To the reaction solution, DIEA (325 μl, 1.87 mmol), HOAt (254 mg, 1.87 mmol), and EDC.HCl (358 mg, 1.87 mmol) were added in this order for 13 hours at room temperature under argon atmosphere. After a saturated aqueous sodium bicarbonate solution was added to the reaction solution, an organic phase was extracted with ethyl acetate three times from an aqueous phase. The organic phase was washed with saturated saline solution, dried with an anhydrous magnesium sulfate. The drying agent was filtered out from the dried residue to obtain a filtrate. The filtrate was concentrated under reduced pressure to obtain a residue. The residue was purified by silica-gel column chromatography (50 g, chloroform:methanol=30:1) to obtain TEG-Trivalent-(O^tBu)₃ (Compound 22) as a colorless oily object. A yield thereof was 1.05 g (99%).

¹H-NMR spectrum (600 MHz, CDCl₃) measurement was conducted on Compound 22 so obtained to find that δ3.91 (s, 2H, —OCH₂CONH—), 3.70-3.54 (m, 13H, —OCH₂CH₂O—×3, CH₂CH(CH₂—)(S—)), 3.55 (t, 2H, J=5.5 Hz, —CONHCH₂CH₂O—), 3.45 (q, 2H, J=5.5 Hz, —CONHCH₂CH₂O—), 3.20-3.16 (m, 1H, —SCH₂(1H)—), 3.14-3.09 (m, 1H, —SCH₂(1H)—), 2.49-2.43 (m, 1H, —SCH₂CH₂(1H)—), 2.22-2.17 (m, 8H, —CH₂CH₂CO—×3, —NHCOCH₂CH₂—), 2.00-1.96 (m, 6H, —CH₂CH₂CO—×3), 1.94-1.88 (m, 1H, —SCH₂CH₂(1H)—), 1.74-1.62 (m 4H, —COCH₂CH₂CH₂CH₂—), 1.52-1.41 (m, 2H, —COCH₂CH₂CH₂CH₂—), 1.44 (s, 27H, —CH₃×9). This could examine a structure of Compound 22.

(3) Synthesis of TEG-Trivalent-(NHBOc)₃ (Compound 25) (See FIG. 13)

The Compound 22 (TEG-Trivalent-(O^tBu)₃) (500 mg, 0.587 mmol) was dissolved in a mixture solution of dichloromethane and water (2.2 ml, 10:1), mixed with TFA (2 ml) at 0° C., and stirred for 1 hour at 0° C. The reaction solution was concentrated and then subjected to azeotropy with toluene to obtain a residue (Compound 23). The residue and N-Boc-phenylenediamine (Compound 24) (612 mg, 2.94 mmol) were dissolved in anhydrous dimethylformamide (10 ml). To the reaction solution, DIEA (380 μl, 2.94 mmol), HOAt (400 mg, 2.94 mmol), and EDC.HCl (563 mg, 2.94 mmol) were added in this order at room temperature under argon atmosphere, and the resulting mixture was stirred for 19 hours. After a saturated aqueous sodium bicarbonate solution was added to the reaction solution, an organic phase was extracted with AcOEt three times from an aqueous phase. The organic phase washed with saturated saline solution, dried with an anhydrous magnesium sulfate. The drying agent was filtered out from the dried residue to obtain a filtrate. The filtrate was concentrated under reduced pressure to obtain a residue. The residue was purified by silica-gel column chromatography (50 g, chloroform:acetone=3:1) to obtain TEG-Trivalent-(NHBoc)₃ (Compound 25) as a light yellow oily object. A yield thereof was 230 mg (31%).

¹H-NMR spectrum (600 MHz, CDCl₃) measurement was conducted on Compound 25 so obtained to find that δ8.72 (bs, 3H, —NHCO—), 7.56 (bs, 3H, aromatic), 7.22-7.10 (m, 6H, aromatic), 6.91 (bs, 3H, —NHCO—), 3.85 (s, 2H, —OCH₂CONH—), 3.67-3.57 (m, 9H, ethylene glycol chain, CH2CH(CH₂—)(S—)), 3.55-3.47 (m, 6H, ethylene glycol chain, —CONHCH₂CH₂O—), 3.38 (q, 2H, J=5.2 Hz, —CONHCH₂CH₂O—), 3.14 (ddd, 1H, J=5.5, 6.9, 12.4 Hz, —SCH₂(1H)—), 3.08 (ddd, 1H, J=6.9, 6.9, 12.4 Hz, —SCH₂(1H)—), 2.43-2.35 (m, 7H, —CH₂CH₂CO—×3, —SCH₂CH₂(1H)—), 2.08 (t, 2H, J=6.9 Hz, —NHCOCH₂CH₂—), 2.17-2.12 (m, 6H, —CH₂CH₂CO—×3), 1.88-1.83 (m, 1H, —SCH₂CH₂(1H)—), 1.65-1.50 (m 4H, —COCH₂CH₂CH₂CH₂—), 1.50 (s, 27H, —CH₃×9), 1.46-1.29 (m, 2H, —COCH₂CH₂CH₂CH₂—). This could examine a structure of Compound 25.

(4) Synthesis of Ligand Conjugate TEG-Trivalent-(Mal)₃ (Compound 27) (See FIGS. 13 and 14)

The Compound 25 (TEG-Trivalent-(OtBu)3)(500 mg, 0.587 mmol) was dissolved in a mixture solution of dichloromethane and water (4.4 ml, 10:1), mixed with TFA (2 ml) at 0° C., and stirred for 1.5 hours at 0° C. The reaction mixture was concentrated and then subjected to azeotropy with toluene to obtain a residue (Compound 26). The residue was used in a subsequent reductive amination reaction, without being purified. A yield thereof was 252 mg.

The following will describe with reference to FIG. 14. The obtained residue (Compound 26)(12.1 mg, 8.88 μmol) and maltose (9.60 mg, 26.7 μmol) were dissolved in a mixture solution of dimethylacetamide and water (1:1, 600 μl), and incubated for 7 hours at 37° C. To the reaction solution, acetic acid (30 μl) and sodium cyanoborohydride (5.58 mg, 88.8 μmol) were added. The reaction mixture was again incubated for 70 hours at 37° C. The reaction mixture was freeze-dried to obtain a residue. The residue was purified by a preparative high-performance liquid chlomatography (ODS column, methanol:water=50:50). A ligand conjugate TEG-Trivalent-(Mal)$_3$(Compound 27) was obtained as a white solid.

$^1$H-NMR spectrum (600 MHz, D$_2$O) measurement was conducted on Compound 27 so obtained to find that δ7.02 (dd, 3H, J=7.6, 8.2 Hz, aromatic), 6.72 (s, 3H, aromatic), 6.60 (dd, 3H, J=1.4, 7.6 Hz, aromatic), 6.44 (dd, 3H, J=1.4, 8.2 Hz, aromatic), 4.91 (d, 3H, J=3.4 Hz, H-1'×3), 3.82-3.73 (m, 8H, H-2×3, H-5×3, —OCH$_2$CONH—), 3.73-3.67 (m, 9H, H-3× 3, H-5'×3, H-6a'×3), 3.65 (dd, 3H, J=2.1, 12.4 Hz, H-6b'×3), 3.59 (dd, 3H, J=4.8, 12.4 Hz, H-6a×3), 3.55 (dd, 3H, J=5.5, 6.2 Hz, H-4×3) 3.55 (dd, 3H, J=9.6, 9.6 Hz, H-3'×3), 3.50-3.36 (m, 12H, —OCH$_2$CH$_2$O—×3), 3.45-3.40 (m, 3H, H-6b×3), 3.42-3.38 (m, 1H, CH$_2$CH(CH$_2$—)(S—)), 3.38 (dd, 3H, J=3.4, 10.3 Hz, H-2'×3), 3.40 (t, 2H, J=5.5 Hz, —CONHCH$_2$CH$_2$O—), 3.25 (dd, 3H, J=9.6, 9.6 Hz, H-4'×3), 3.15-3.10 (m, 5H, —CONHCH$_2$CH$_2$O—, H-1a×3), 3.02 (dd, J=8.2, 13.7 Hz, H-1b×3), 3.01-2.97 (m, 1H, —SCH$_2$(1H)—), 2.96-2.91 (m, 1H, —SCH$_2$(1H)—), 2.29-2.25 (m, 6H, CH$_2$CH$_2$CO—×3), 2.26-2.19 (m, 1H, —SCH$_2$CH$_2$(1H)—), 2.05-1.98 (m, 6H, —CH$_2$CH$_2$CO—×3), 1.99 (t, 2H, J=6.9 Hz, —NHCOCH$_2$CH$_2$—), 1.74-1.69 (m, 1H, —SCH$_2$CH$_2$(1H)—), 1.50-1.30 (m 4H, —COCH$_2$CH$_2$CH$_2$CH$_2$—), 1.16-1.10 (m, 2H, —COCH$_2$CH$_2$CH$_2$CH$_2$—). An ESI-MS measurement was conducted to find that the m/z was 981.41 [(M+2Na)$^{2+}$]. This could examine a structure of Compound 27. It is to be noted that a molecular mass of the Compound 27 is C$_{82}$H$_{132}$N$_8$O$_{39}$S$_2$: 1916.80.

Example 5

Synthesis of Linker Compound (Compound 32) and Ligand Conjugate (Compound 34)

Figure 15:
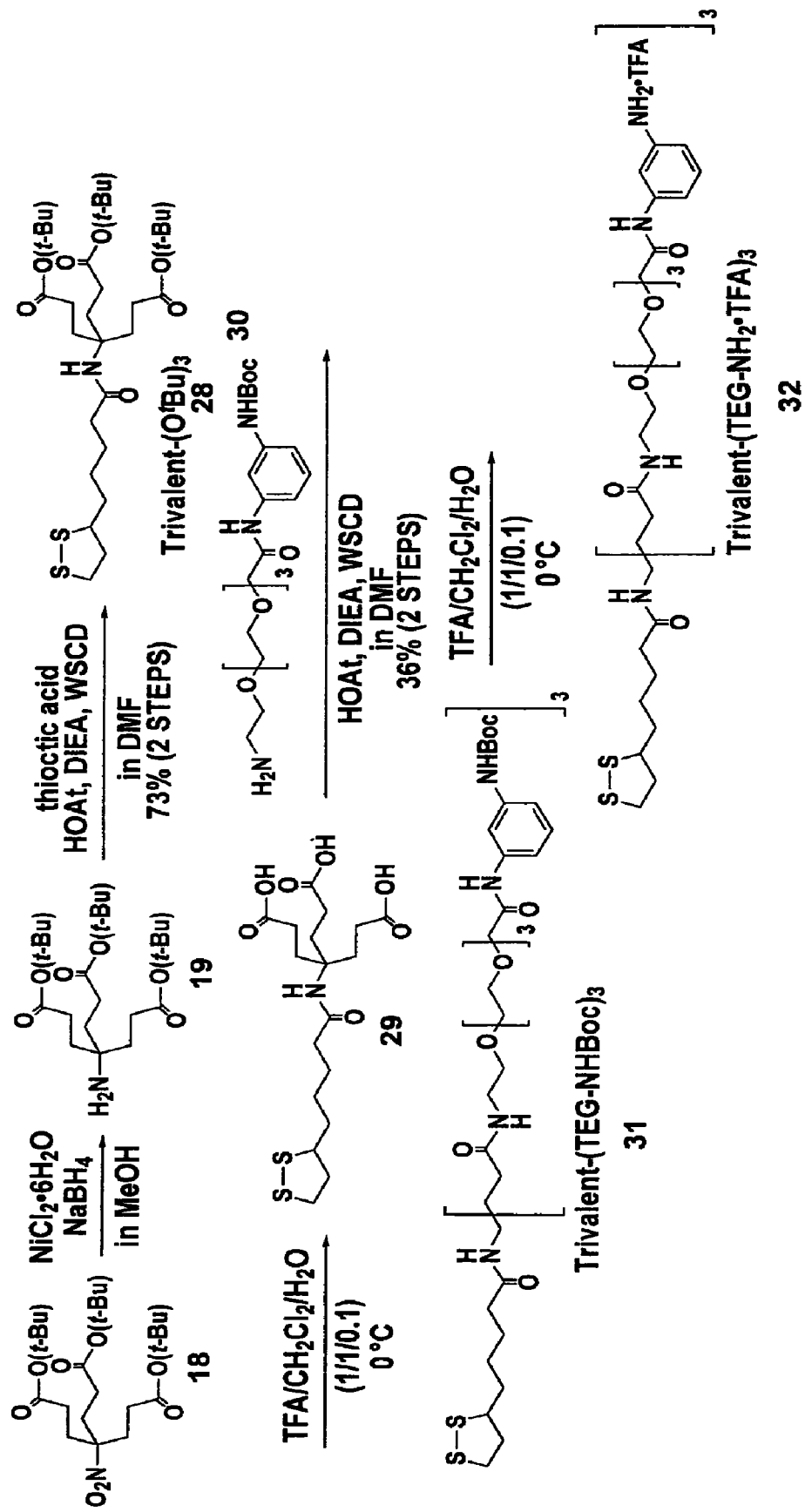
FIG. 15 is a schematic diagram illustrating an example of synthetic pathway of a linker compound (Compound 32) according to the present invention.
Figure 16:
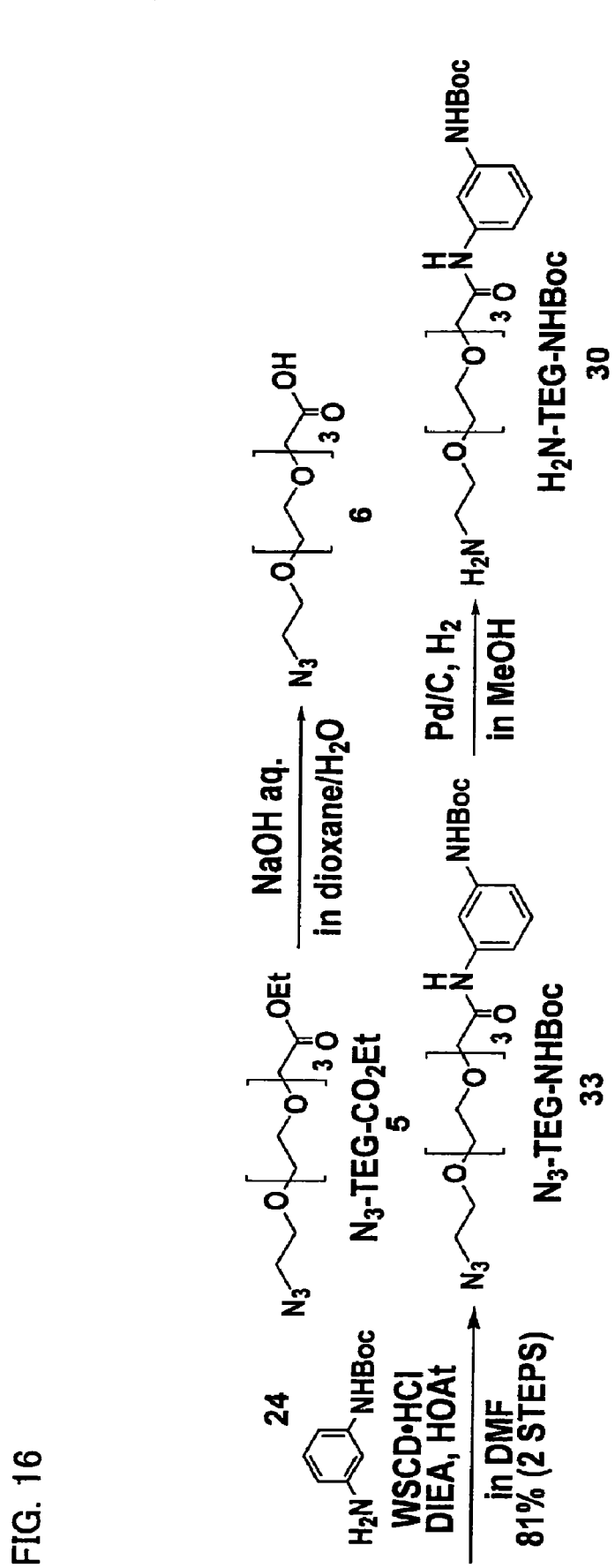
FIG. 16 is a schematic diagram illustrating an example of synthetic pathway of H2N-TEG-NHBoc (Compound 30).
Figure 17:
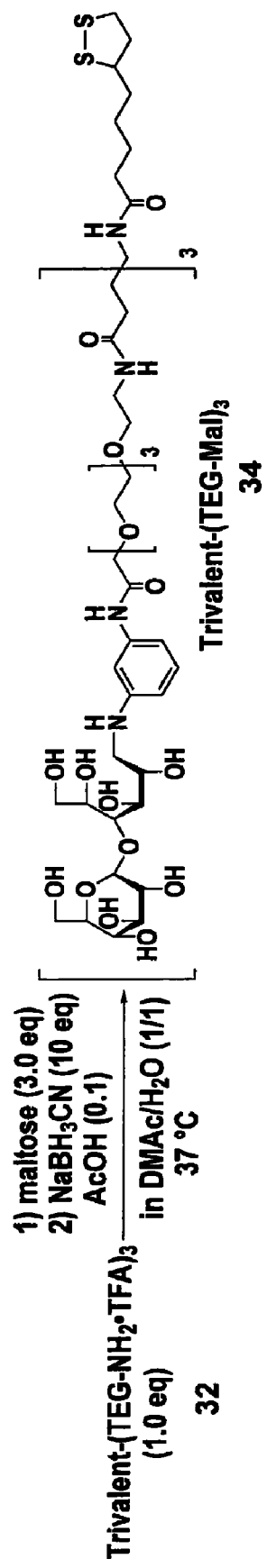
FIG. 17 is a schematic diagram illustrating an example of synthetic pathway of a ligand conjugate (Compound 34) according to the present invention.

One of the linker compounds according to the present invention, i.e. the linker compound (Compound 32) having a structure represented by general formula (1) where a is 4, b is 0, d is 0, e is 0 and X is represented by general formula (4) wherein q$^1$, q$^2$, q$^3$ are 2, r$^1$, r$^2$, and r$^3$ are 1, t$^1$, t$^2$, and t$^3$ are 4, and u$^1$, u$^2$, and u$^3$ are 1, and the ligand conjugate (Compound 34) having a structure represented by general formula (7) where a is 4, b is 0, d is 0, e is 0, q$^1$, q$^2$, an q$^3$ are 2, and r$^1$, r$^2$, and r$^3$ are 1, t$^1$, t$^2$, and t$^3$ are 4, and u$^1$, u$^2$, and u$^3$ are 1, R' is hydrogen (H), and R is represented by general formula (6-2) were synthesized by the following procedure. FIG. 15 illustrates a process of synthesizing the linker compound (Compound 32). FIG. 16 illustrates a process of synthesizing Compound 30 used in the process of synthesizing the linker compound (Compound 32). FIG. 17 illustrates a process of synthesizing the ligand conjugate (Compound 34) from the linker compound (Compound 32). Reference numbers given to the compounds in the descriptions of Example 5 correspond to reference numbers described in FIGS. 15, 16, and 17.

[Measurement Method, Reagent, and Others]

For $^1$H-NMR spectrum measurement, JOEL-Delta600 Spectrometer was used. For CDCl$_3$, chemical shifts are expressed in δ-values in accordance with chemical shift of tetramethylsilane (0.00 ppm) as a reference substance. For D$_2$O, chemical shifts are expressed in α-values in accordance with chemical shift of DHO (4.65 ppm) as a reference substance. A mass spectrometry measurement was carried out by using PerSeptive Biosystem Mariner™ Biospectrometry Workstation. A medium-pressure silica gel chromatography was carried out by using Silicagel 60 (Merck, 0.040-0.063 mm). A thin-layer chromatography was carried out by using Precoated Silicagel 60 F254 (Merck, 0.5 mm). All reagents and dehydrated solvents were purchased from Kanto Chemical. Co. Ltd.

(1) Synthesis of Trivalent-(O$^t$Bu)$_3$ (Compound 28) (See FIG. 15)

O$_2$N-Trivalent-(O$^t$Bu)$_3$ (Compound 18) (757 mg, 1.70 mmol) and NiCl$_2$.6H$_2$O (80.8 mg, 0.340 mmol) were dissolved in methanol (20 ml). To the mixture, sodium borohydride (322 mg, 8.50 mmol) was added with five-equivalent portions at 0° C. The reaction mixture was stirred for 30 minutes at room temperature. Methanol was removed by concentration. To the reaction solution, water and chloroform were added. After the mixture was filtrated with celite, an organic phase was extracted from an aqueous phase with chloroform three times. After the organic phase was dried with anhydrous sodium sulfate, the drying agent was filtered out from the dried residue to obtain a filtrate. The filtrate was concentrated under reduced pressure to obtain a residue (Compound 19). The obtained residue and thioctic acid (351 mg, 1.70 mmol) were dissolved in anhydrous dimethylformamide (10 ml). To the mixture, DIEA (592 μl, 3.40 mmol), HOAt (463 mg, 3.40 mmol), and EDC.HCl (652 mg, 3.40 mmol) were added in this order under argon atmosphere at room temperature, and the resulting mixture was stirred for 16 hours. After the reaction solution was mixed with water, an organic phase was extracted from an aqueous phase with ethyl acetate three times. The organic phase washed with a saturated saline solution and a saturated aqueous sodium bicarbonate solution, and dried with an anhydrous magnesium sulfate. Then, the drying agent was filtered out from the dried residue to obtain a filtrate. The filtrate was concentrated under reduced pressure to obtain a residue. The residue was purified by silica gel column chromatography (50 g, hexane:ethyl acetate=3:1) to obtain Trivalent-(O$^t$Bu)$_3$ (Compound 28) as a light yellow oily object. A yield thereof was 750 mg (73%).

$^1$H-NMR spectrum (600 MHz, CDCl$_3$) measurement was conducted on Compound 28 so obtained to find that δ5.91 (s, 1H, —CONH—), 3.57 (ddd, 1H, J=6.2, 6.2, 12.4 Hz, CH$_2$CH(CH$_2$—)(S—)), 3.18 (ddd, 1H, J=5.5, 5.5, 12.4 Hz, —SCH$_2$(1H)—), 3.11 (ddd, 1H, J=6.9, 7.6, 12.4 Hz, —SCH$_2$(1H)—), 2.46 (ddd, 1H, J=6.2, 6.2, 12.4 Hz, —SCH$_2$CH$_2$(1H)—), 2.22 (t, 8H, J=7.6 Hz, —CH$_2$CH$_2$CO—×3), 2.11 (dd, 2H, J=6.9, 7.6 Hz, —COCH$_2$CH$_2$CH$_2$—), 1.97 (t, 6H, J=7.6 Hz, —CH$_2$CH$_2$CO—×3), 1.91 (ddd, 1H, J=6.9, 6.9, 12.4 Hz —SCH$_2$CH$_2$(1H)—), 1.74-1.57 (m 4H, —COCH$_2$CH$_2$CH$_2$CH$_2$—), 1.51-1.38 (m, 2H, —COCH$_2$CH$_2$CH$_2$CH$_2$—), 1.43 (s, 27H, —CH$_3$×9). $^{13}$C-NMR (150 MHz, CDCl$_3$) measurement was conducted to find that δ172.9, 172.1, 80.7, 57.3, 56.3, 40.2, 38.5, 37.2, 34.6, 30.0, 29.8, 28.9, 28.1, and 25.3. This could examine a structure of Compound 28.

(2) Synthesis of N$_3$-TEG-NHBoc (Compound 33) (See FIG. 16)

N$_3$-TEG-CO$_2$Et (Compound 5)(500 mg, 1.64 mmol) was dissolved in 1,4-dioxane (6 ml). An aqueous sodium hydrate solution (1 ml, 150 mg/ml) was added to the reaction mixture at 0° C., and stirred for 3 hours at 0° C. After 1,4-dioxane was removed by concentration, 5% aqueous potassium hydrogen sulfate solution and chloroform were added to the resultant. An organic phase was extracted from an aqueous phase with chloroform three times. The organic phase was dried with anhydrous sodium sulfate. Thereafter, the drying agent was filtered out from the dried residue to obtain a filtrate. The filtrate was concentrated under reduced pressure to obtain a residue (Compound 6). The residue was used in a subsequent coupling reaction, without being purified. A yield thereof was 435 mg (96%). The obtained residue and N-Boc-phenylenediamine (Compound 24) (327 mg, 1.57 mmol) were dissolved in anhydrous dimethylformamide. To the mixture, DIEA (410 µl, 2.35 mmol), HOAt (320 mg, 2.35 mmol), and EDC.HCl (451 mg, 2.35 mmol) were added in this order under argon atmosphere at room temperature, and the resulting mixture was stirred for 14 hours. After the reaction solution was mixed with water, an organic phase was extracted from an aqueous phase with ethyl acetate three times. The organic phase washed with a saturated saline solution and a saturated aqueous sodium bicarbonate solution, and dried with an anhydrous magnesium sulfate. Then, the drying agent was filtered out from the dried residue to obtain a filtrate. The filtrate was concentrated under reduced pressure to obtain a residue. The residue was purified by silica-gel column chromatography (50 g, toluene:ethyl acetate=1:1) to obtain $N_3$-TEG-NHBoc (Compound 33) as a light yellow oily object. A yield thereof was 597 mg (81%).

$^1$H-NMR spectrum (600 MHz, CDCl$_3$) measurement was conducted on Compound 33 so obtained to find that δ8.81 (bs, 1H, —NHCO—), 7.61 (s, 1H, aromatic), 7.35 (d, 1H, J=6.9 Hz, aromatic), 7.26-7.20 (m, 2H, aromatic), 6.71 (bs, 1H, —NHCO—), 4.10 (s, 2H, —OCH$_2$CONH—), 3.78-3.70 (m, 8H, ethyleneglycol chain), 3.67-3.62 (m, 6H, ethylene glycol chain, —CONHCH$_2$CH$_2$O—), 3.35 (t, 2H, J=5.5 Hz, —CONHCH$_2$CH$_2$O—). $^{13}$C-NMR (150 MHz, CDCl$_3$) measurement was conducted to find that δ168.3, 152.6, 139.0, 138.0, 129.5, 114.5, 114.3, 109.8, 80.5, 71.2, 70.6, 70.6, 70.6, 70.5, 70.4, 70.2, 70.0, 50.6, and 28.3 This could examine a structure of Compound 33.

(3) Synthesis of H$_2$N-TEG-NHBoc (Compound 30) (See FIG. 16)

The Compound 33 (N$_3$-TEG-NHBoc) (200 mg, 0.425 mmol) was dissolved in methanol (4 ml), mixed with 10% Pd/C (200 mg), and stirred for 1.5 hours at room temperature under hydrogen atmosphere. The Pd/C was filtered out to obtain a filtrate. Thereafter, the filtrate was concentrated under reduced pressure to obtain a residue (Compound 30). The residue was used in a subsequent reaction, without being purified. A yield thereof was 174 mg (93%).

(4) Synthesis of Trivalent-(TEG-NHBOc)$_3$ (Compound 31) (See FIG. 15)

The Compound 28 (Trivalent-(O$^t$Bu)$_3$)(64.2 mg, 0.106 mmol) was dissolved in a mixture solution of dichloromethane and water ((2.2 ml, 10:1), mixed with TFA (2 ml) at 0° C., and stirred for 1 hour at 0° C. The reaction mixture was concentrated and then subjected to azeotropy with toluene to obtain a residue (Compound 29). The residue and H$_2$N-TEG-NHBoc (Compound 30) (174 mg, 0.425 mmol) were dissolved in anhydrous dimethylformamide (3 ml). To the mixture, DIEA (92.6 µl, 0.532 mmol), HOAt (72.3 mg, 0.532 mmol), and EDC.HCl (102 mg, 0.532 mmol) were added in this order under argon atmosphere at room temperature, and the resulting mixture was stirred for 14 hours. After the reaction solution was mixed with water, an organic phase was extracted from an aqueous phase with ethyl acetate three times. The organic phase washed with a saturated saline solution, and dried with an anhydrous magnesium sulfate. Then, the drying agent was filtered out from the dried residue to obtain a filtrate. The filtrate was concentrated under reduced pressure to obtain a residue. The residue was purified by silica-gel column chromatography (50 g, chloroform:methanol=30:1) to obtain Trivalent-(TEG-NHBOc)$_3$ (Compound 31) as a light yellow oily object. A yield thereof was 64.7 mg (36%).

$^1$H-NMR spectrum (600 MHz, CDCl$_3$) measurement was conducted on Compound 31 so obtained to find that δ8.88 (bs, 3H, —NHCO—×3), 7.67 (bs, 3H, aromatic), 7.42 (bs, 3H, —NHCO—×3), 7.31 (d, 3H, J=7.7 Hz, aromatic), 7.27 (d, 3H, J=8.2 Hz, aromatic), 7.22 (dd, 3H, J=7.7, 8.2 Hz, aromatic), 6.63 (bt, 3H, J=4.8 Hz, —NHCO—×3), 4.11 (s, 6H, —OCH$_2$CONH—×3), 3.78-3.58 (m, 36H, ethylene glycol chain), 3.57-3.49 (m, 1H, CH$_2$CH(CH$_2$—)(S—)), 3.50 (t, 6H, J=5.5 Hz, —CONHCH$_2$CH$_2$O—×3), 3.36 (q, 6H, J=5.2 Hz, —CONHCH$_2$CH$_2$O—×3), 3.15 (ddd, 1H, J=5.5, 6.9, 11.0 Hz, —SCH$_2$(1H)—), 3.09 (ddd, 1H, J=6.9, 6.9, 11.0 Hz, —SCH$_2$(1H)—), 2.42 (ddd, 1H, J=6.9, 6.9, 12.4 Hz, —SCH$_2$CH$_2$(1H)—), 2.12-2.06 (m, 8H, —CH$_2$CH$_2$CO—×3, —NHCOCH$_2$CH$_2$CH$_2$—), 1.95-1.88 (m, 6H, —CH$_2$CH$_2$CO—×3), 1.87 (ddd, 1H, J=6.9, 6.9, 12.4 Hz, —SCH$_2$CH$_2$(1H)—), 1.70-1.50 (m 4H, —COCH$_2$CH$_2$CH$_2$—), 1.50 (s, 27H, —CH$_3$×9), 1.48-1.33 (m, 2H, —COCH$_2$CH$_2$CH$_2$CH$_2$—). $^{13}$C-NMR (150 MHz, CDCl$_3$) measurement was conducted to find that δ173.3, 172.8. 168.4, 152.8, 139.3, 137.8, 129.3, 114.5, 114.4, 110.1, 80.2, 71.1, 70.5, 70.4, 70.4, 70.3, 70.1, 70.1, 69.7, 57.3, 56.4, 40.1, 39.2, 38.3, 37.0, 34.5, 31.1, 30.5, 28.8, 28.3, and 25.4. An ESI-MS measurement was conducted to find that the m/z was 875.41[(M+2Na)$^{2+}$]. This could examine a structure of Compound 31. It is to be noted that a molecular mass of the Compound 31 is C$_{81}$H$_{128}$N$_{10}$O$_{25}$S$_2$:1704.85.

(5) Synthesis of Ligand Conjugate Trivalent-(TEG-Mal)$_3$ (Compound 34) (See FIGS. 16 and 17)

The Compound 31 (Trivalent-(TEG-NHBOc)$_3$) (64.7 mg, 37.9 µmol) was dissolved in a mixture solution of dichloromethane and water (2.2 ml, 10:1), mixed with TFA (2 ml) at 0° C., and stirred for 2.5 hours at 0° C. The reaction mixture was concentrated and then subjected to azeotropy with toluene to obtain a residue (Compound 32). The residue was used in a subsequent reductive amination reaction, without being purified. A yield thereof was 70 mg.

The following will describe with reference to FIG. 17. The obtained residue (Compound 32) (content of 6.95 mg, 3.77 µmol) and maltose (4.07 mg, 11.3 µmol) were dissolved in a mixture solution of dimethylacetamide and water (1:1, 400 µl), and incubated for 13 hours at 37° C. To the reaction solution, acetic acid (20 µl) and sodium cyanoborohydride (2.24 mg, 35.6 µmol) were added. The reaction mixture was again incubated for 59 hours at 37° C. The reaction mixture was freeze-dried to obtain a residue. The residue was purified by a preparative high-performance liquid chlomatography (ODS column, methanol:water=50:50) to obtain Trivalent-(TEG-Mal)$_3$ (Compound 34) as a white solid. A yield thereof was 4.46 mg (50%).

$^1$H-NMR spectrum (600 MHz, D$_2$O) measurement was conducted on Compound 34 so obtained to find that δ7.05 (dd, 3H, J=7.6, 8.2 Hz, aromatic), 6.77 (s, 3H, aromatic), 6.63 (dd, 3H, J=1.4, 7.6 Hz, aromatic), 6.47 (dd, 3H, J=1.4, 8.2 Hz, aromatic), 4.92 (d, 3H, J=3.4 Hz, H-1'×3), 4.01 (s, 6H, —OCH$_2$CONH—×3), 3.81 (ddd, 3H, J=2.1, 4.8, 7.6 Hz, H-2×3), 3.71 (ddd, 3H, J=4.1, 7.6 Hz, H-5×3), 3.74-3.68 (m, 9H, H-3×3, H-5'×3, H-6a'×3), 3.65 (dd, 3H, J=2.1, 12.4 Hz, H-6b'×3), 3.64-3.60 (m, 3H, H-6a×3), 3.64-3.42 (m, 36H, —OCH$_2$CH$_2$O—×9), 3.56-3.52 (m, 6H, H-4×3, H-3'×3), 3.47-3.43 (m, 3H, H-6b×3), 3.42-3.39 (m, 1H, CH$_2$CH(CH$_2$—)(S—)), 3.38 (dd, 3H, J=3.4, 9.6 Hz, H-2'×3), 3.37 (t, 6H, J=4.8 Hz, —CONHCH$_2$CH$_2$O—×3), 3.26 (dd, 3H, J=9.6, 9.6 Hz, H-4'×3), 3.15 (dd, 3H, J=4.8, 13.7 Hz, H-1a×3), 3.14 (t, 6H, —CONHCH$_2$CH$_2$O—×3), 3.06 (dd, J=7.6, 13.7 Hz, H-1b×3), 3.01 (ddd, 1H, J=6.2, 6.2, 11.0 Hz, —SCH$_2$(1H)—), 2.95 (ddd, 1H, J=6.9, 6.9, 11.0 Hz, —SCH$_2$(1H)—), 2.24 (ddd, 1H, J=6.2, 6.2, 12.4 Hz, —SCH$_2$CH$_2$(1H)—), 2.00 (t, 2H, J=6.9 Hz, —NHCOCH$_2$CH$_2$—), 1.96-1.92 (m, 6H, CH$_2$CH$_2$CO—×3), 1.77-1.69 (m, 7H, —CH$_2$CH$_2$CO—×3, —SCH$_2$CH$_2$(1H)—), 1.52-1.32 (m 4H, —COCH$_2$CH$_2$CH$_2$CH$_2$—), 1.20-1.14 (m, 2H, —COCH$_2$CH$_2$CH$_2$CH$_2$—). An ESI-MS measurement was conducted to find that the m/z was 1214.57[(M+2Na)$^{2+}$]. This could examine a structure of Compound 34. It is to be noted that a molecular mass of the Compound 34 is C$_{102}$H$_{170}$N$_{10}$O$_{49}$S$_2$: 2283.06.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, a linker compound of the present invention includes an aromatic amino group end as a moiety capable of taking in three or more units of sugar molecules. The linker compound further includes an S—S bond as a moiety capable of binding to a protein-analyzing supporter such as a sensor chip of surface plasmon resonance (SPR) and affinity chromatography carrier. Still further, the linker compound includes an oligoethylene oxide between a disulfide group and the aromatic amino group, so that a nonspecific hydrophobic interaction can be reduced as much as possible, and a length to the disulfide group for a metal bond can be easily adjusted.

Thus, the use of the linker compound brings about the effect of two-dimensional arrangement of three or more units of sugar molecules onto the supporter with high reproducibility. Since the linker compound is hardly affected by a nonspecific interaction with a protein, it is possible to evaluate biological activities of sugar molecules with high reproducibility in observing interaction between sugar molecules and a protein. Further, it is possible to effectively form a metal-sulfur bond.

Moreover, a ligand conjugate of the present invention includes the linker compound having a sugar molecule introduced therein.

Thus, introduction of the ligand conjugate onto a surface of a protein-analyzing supporter makes it possible to two-dimensionally arrange a plurality of sugar molecules with high reproducibility. This brings about the effect of making it possible to evaluating biological activities of sugar molecules with high reproducibility. Further, it is possible to effectively form a metal-sulfur bond.

According to the present invention, it is possible to obtain a linker compound with which oligosaccharides can be two-dimensionally arranged with high reproducibility while an interval between their sugar chains on a surface of a sensor chip is controlled. Also, it is possible to obtain a ligand conjugate which includes the linker compound and a sugar molecule introduced into the linker compound. The linker compound and the ligand conjugate are very useful for commercialization and communization of a chip including sugar chains of oligosaccharide.

It is expected that development of a chip including sugar chains of oligosaccharide immobilized thereon as a tool for functional analysis of sugar chains and a protein will not only contribute to revealing vital phenomena associated with sugar chains of oligosaccharide, but also become an important technique in development of pharmaceuticals. Therefore, it is considered that the present invention is highly beneficial.

The invention claimed is:

1. A ligand conjugate including a linker compound having a structure represented by following general formula (5), where m$^1$, m$^2$, m$^3$, m$^4$, n, p$^1$, and p$^2$ are independently an integer of 1 to 6, R' is hydrogen (H) or R, and

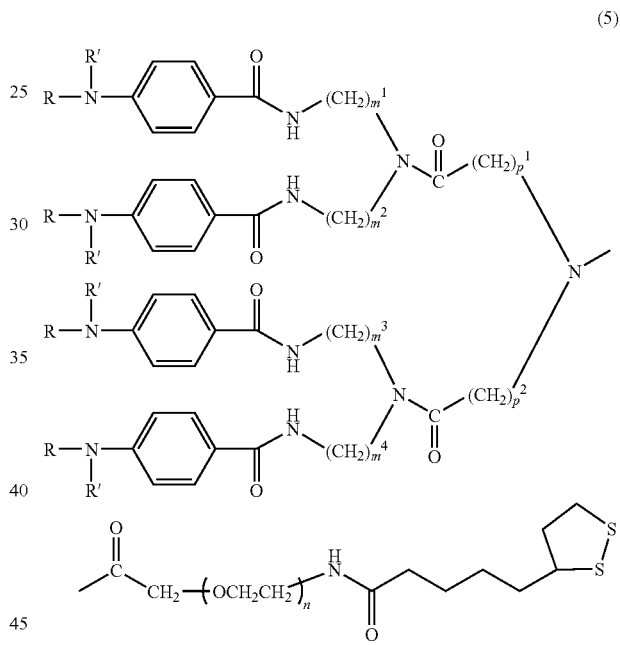

(5)

R is an oligosaccharide-derived compound selected from among the following formulae (6-1) through (6-6),

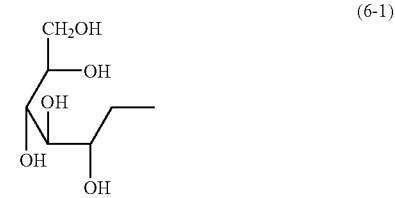

(6-1)

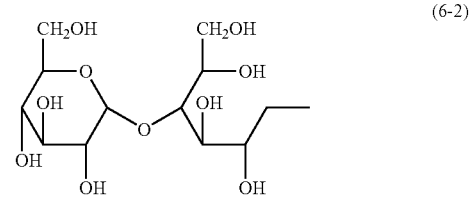

(6-2)

-continued (6-3)
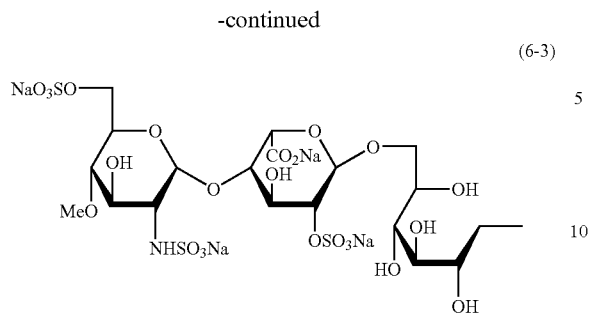

(6-5)
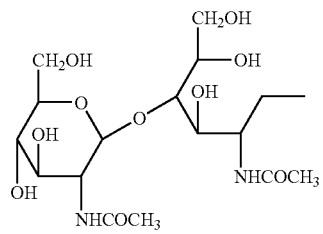

(6-4)
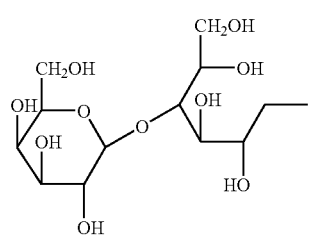

(6-6)
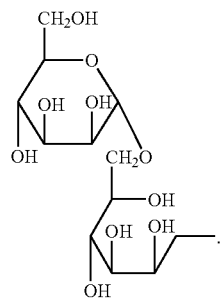

2. A ligand conjugate including a linker compound having a structure represented by following general formula (7), (7)
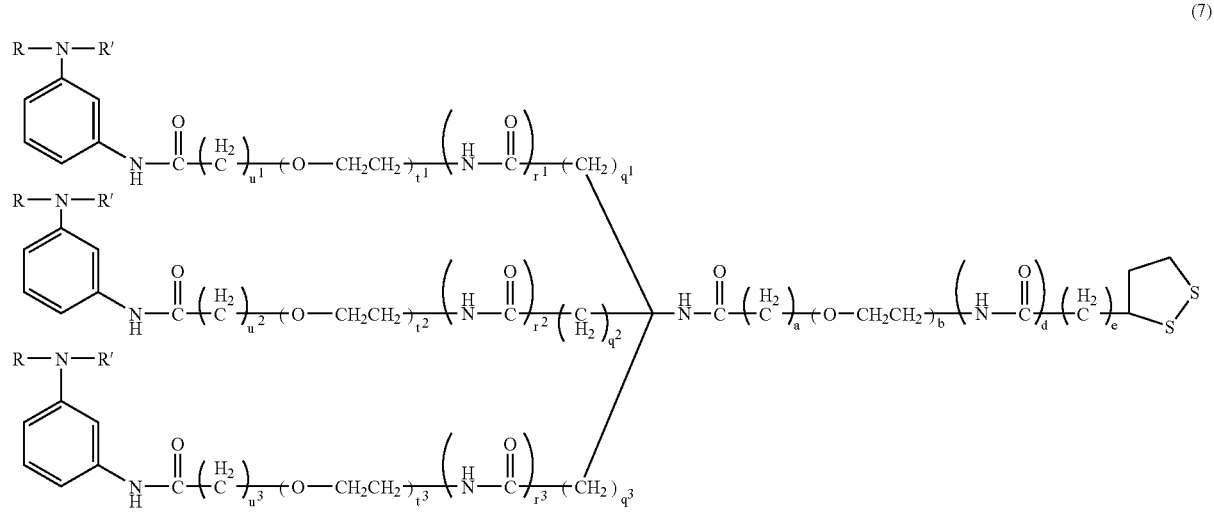

where $a, b, d, e, q^1, q^2, q^3, r^1, r^2, r^3, t^1, t^2, t^3, u^1, u^2$, and $u^3$ are independently an integer of 0 to 6, $t^1, t^2$, and $t^3$ are not 0 when b is 0, b is not 0 when $t^1, t^2$, and $t^3$ are 0, R' is hydrogen (H) or R, and R is an oligosaccharide-derived compound selected from among the following formulae (6-1) through (6-6),

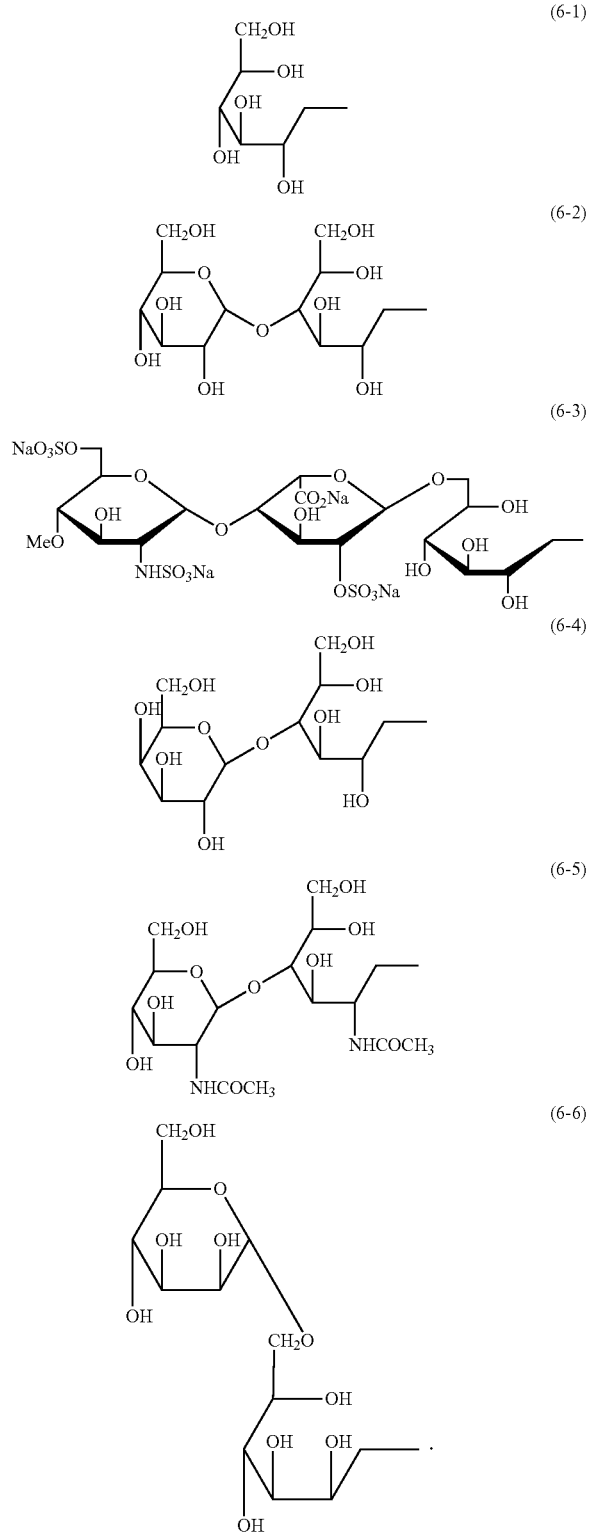

3. A method of arranging a sugar molecule on a surface of a supporter, comprising the step of:
causing a solution containing the ligand conjugate of claim 1 or 2 to come into contact with a supporter comprising metal on a surface thereof.

4. A ligand carrier which comprises the ligand conjugate of claim 1 or 2 immobilized on a supporter comprising metal on a surface thereof.

5. A sensor chip for a surface plasmon resonance, comprising the ligand conjugate according to claim 1 or 2 immobilized onto a surface thereof.

6. The sensor chip of claim 5, wherein the ligand conjugate has a structure represented by formula (5),

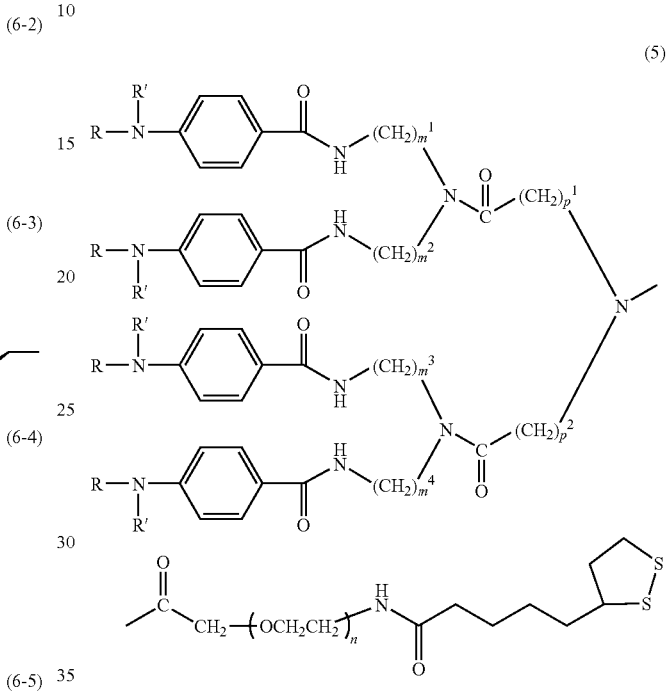

where $m^1$, $m^2$, $m^3$, $m^4$, $n$, $p^1$, and $p^2$ are independently an integer of 1 to 6, R' is hydrogen (H) or R, and R is an oligosaccharide-derived compound selected from among the following formulae (6-1) through (6-6),

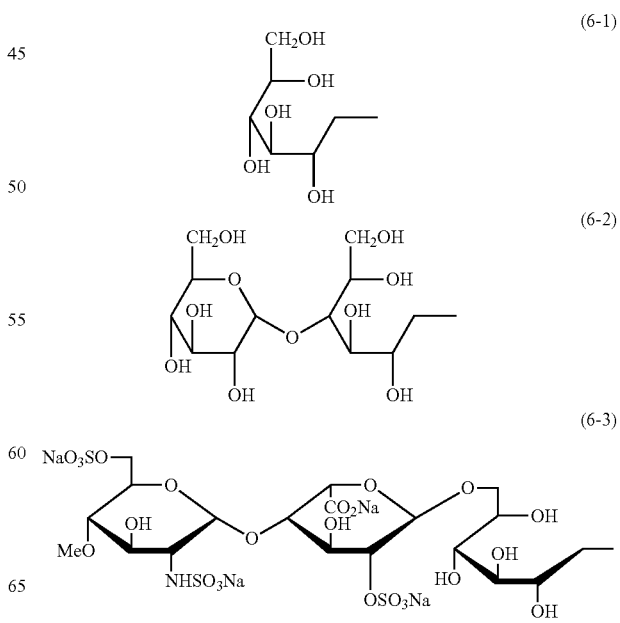

where a, b, d, e, $q^1, q^2, q^3, r^1, r^2, r^3, t^1, t^2, t^3, u^1, u^2$, and $u^3$ are independently an integer of 0 to 6,
$t^1, t^2$, and $t^3$ are not 0 when b is 0,
b is not 0 when $t^1, t^2$, and $t^3$ are 0,
R' is hydrogen (H) or R, and
R is an oligosaccharide-derived compound selected from among the following formulae (6-1) through (6-6),
(6-1)
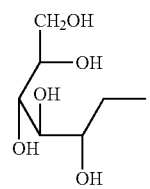
(6-2)
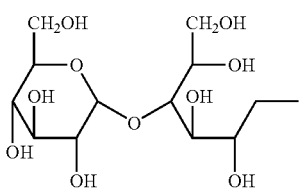
(6-3)
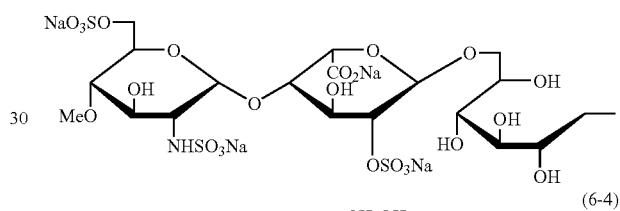
(6-4)
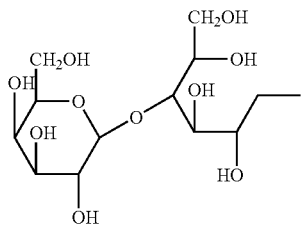
(6-4)
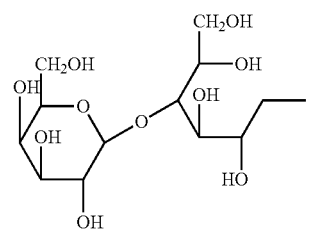
(6-5)
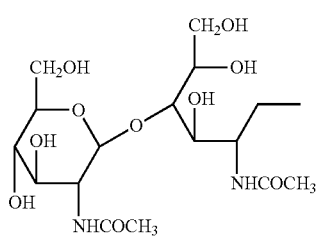
(6-6)
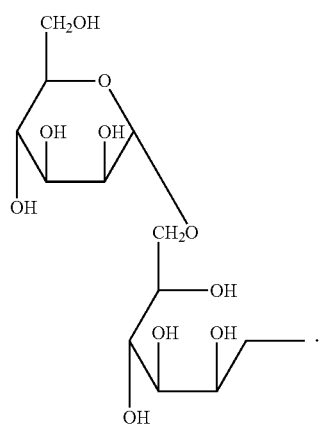
7. The sensor chip of claim 5, wherein the ligand conjugate has a structure represented by formula (7),
(7)
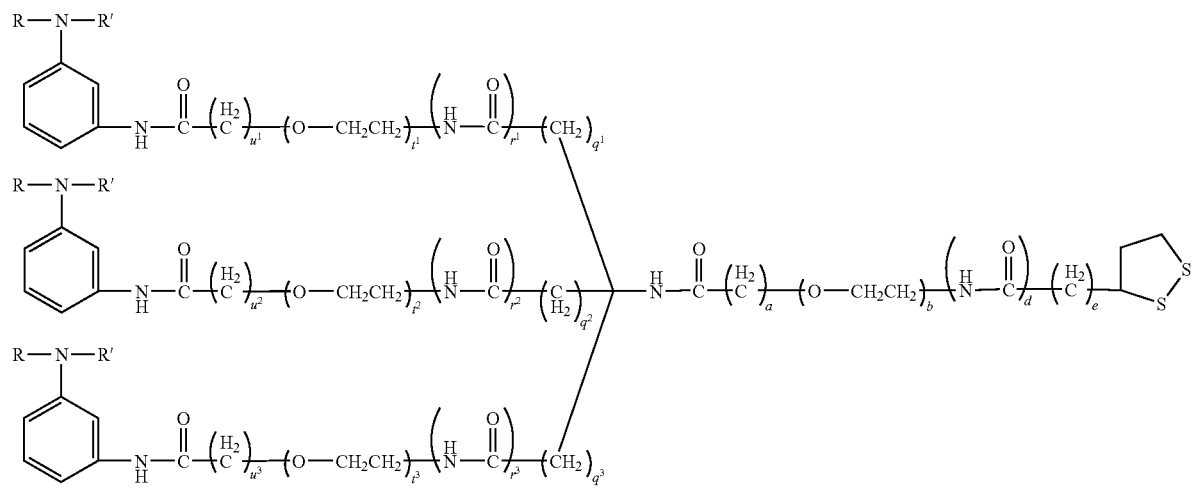

-continued
(6-5)
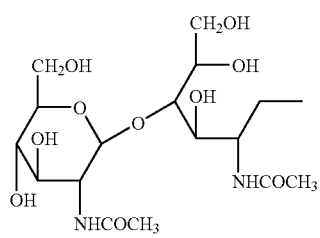
(6-6)
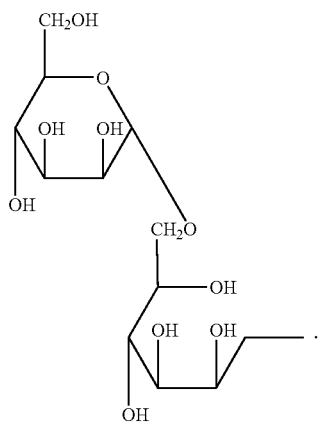
8. A linker compound for use in arrangement of sugar molecules on a supporter,
the linker compound having a structure represented by following general formula (1), where a, b, d, e are independently an integer of 0 to 6,
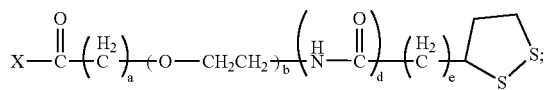
(1)
where a, b, d, e are independently an integer of 0 to 6,
X has the formula (4):
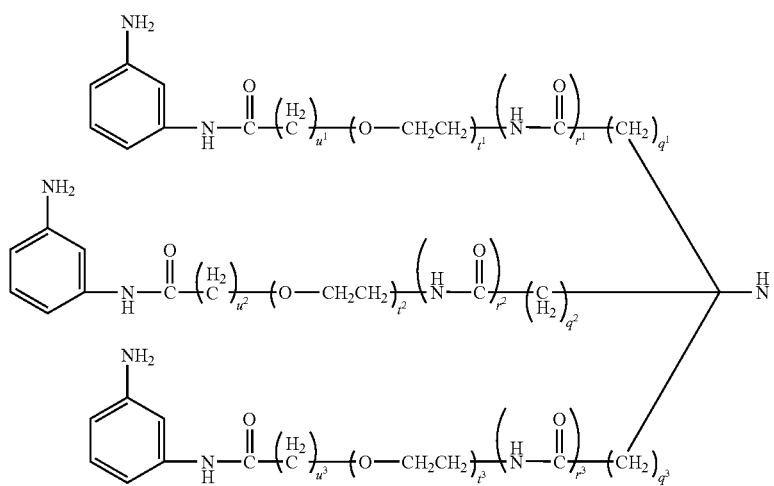
(4)

wherein $q^1$, $q^2$, $q^3$, $r^1$, $r^2$, $r^3$, $t^1$, $t^2$, $t^3$, $u^1$, $u^2$, and $u^3$ are independently an integer of 0 to 6;

and X has oligoethylene oxide therein when b is 0.

9. A linker compound for use in arrangement of sugar molecules on a supporter, the linker compound having a structure represented by following general formula (1),

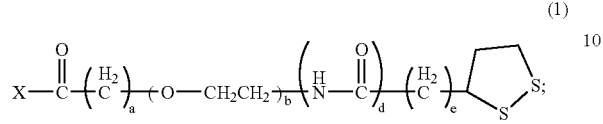

(1)

where a, d, e are independently an integer of 0 to 6, b is an integer of 1 to 6;
X has the formula (3):

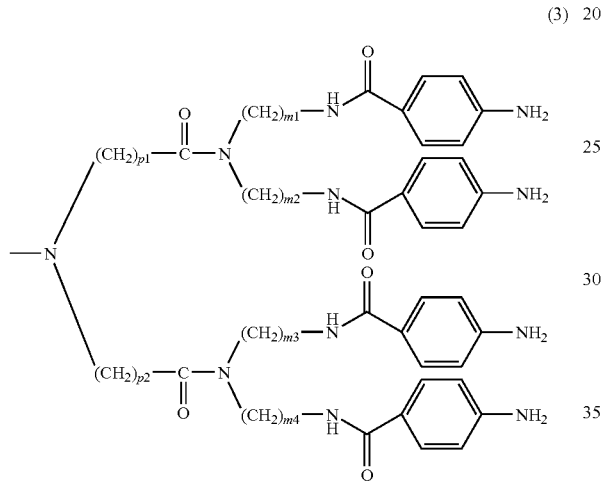

(3)

and m1, m2, m3, m4, p1 and p2 are independently an integer of 1 to 6.

10. The linker compound according to claim 8 or 9, wherein the group of general formula (1) is a group of formula (2):

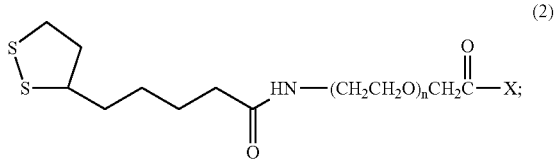

(2)

where n is an integer of 1 to 6.

* * * * *